(12) United States Patent
Plachetka

(10) Patent No.: US 10,603,283 B2
(45) Date of Patent: *Mar. 31, 2020

(54) COMPOSITIONS AND METHODS FOR DELIVERY OF OMEPRAZOLE PLUS ACETYLSALICYLIC ACID

(71) Applicant: GENUS LIFESCIENCES INC., Allentown, PA (US)

(72) Inventor: John R. Plachetka, Chapel Hill, NC (US)

(73) Assignee: GENUS LIFESCIENCES, INC., Allentown, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/996,701

(22) Filed: Jun. 4, 2018

(65) Prior Publication Data

US 2019/0070118 A1 Mar. 7, 2019

Related U.S. Application Data

(63) Continuation of application No. 15/338,825, filed on Oct. 31, 2016, now Pat. No. 9,987,231, which is a continuation of application No. 14/367,972, filed as application No. PCT/US2012/071759 on Dec. 27, 2012, now Pat. No. 9,539,214.

(60) Provisional application No. 61/585,432, filed on Jan. 11, 2012, provisional application No. 61/580,861, filed on Dec. 28, 2011.

(51) Int. Cl.
*A61K 9/24* (2006.01)
*A61K 31/4439* (2006.01)
*A61K 31/616* (2006.01)

(52) U.S. Cl.
CPC .......... *A61K 9/209* (2013.01); *A61K 31/4439* (2013.01); *A61K 31/616* (2013.01)

(58) Field of Classification Search
CPC ... A61K 9/209; A61K 31/616; A61K 31/4439
See application file for complete search history.

(56) References Cited

U.S. PATENT DOCUMENTS

| | | | |
|---|---|---|---|
| 4,198,390 A | 4/1980 | Rider | |
| 4,255,431 A | 3/1981 | Junggren et al. | |
| 4,344,929 A | 8/1982 | Bonsen et al. | |
| 4,508,905 A | 4/1985 | Junggren et al. | |
| 4,554,276 A | 11/1985 | LaMattina | |
| 4,562,261 A | 12/1985 | Hirata et al. | |
| 4,619,934 A | 10/1986 | Sunshine et al. | |
| 4,676,984 A | 6/1987 | Wu et al. | |
| 4,704,278 A | 11/1987 | Wu et al. | |
| 4,726,951 A | 2/1988 | Panoz et al. | |
| 4,738,974 A | 4/1988 | Brandstrom | |
| 4,757,060 A | 7/1988 | Lukacsko et al. | |
| 4,758,579 A | 7/1988 | Kohl et al. | |
| 4,766,117 A | 8/1988 | Crawford et al. | |
| 4,786,505 A | 11/1988 | Lovgren et al. | |
| 4,853,230 A | 8/1989 | Lovgren et al. | |
| 4,865,847 A | 9/1989 | Gosswein | |
| 4,948,581 A | 8/1990 | Sawayangi et al. | |
| 4,965,065 A | 10/1990 | Lukacsko et al. | |
| 5,026,560 A | 6/1991 | Makino et al. | |
| 5,035,899 A | 7/1991 | Saeki et al. | |
| 5,037,815 A | 8/1991 | Lukacsko et al. | |
| 5,043,358 A | 8/1991 | Lukacsko et al. | |
| 5,051,262 A | 9/1991 | Panoz et al. | |
| 5,093,132 A | 3/1992 | Makino et al. | |
| 5,204,118 A | 4/1993 | Goldman et al. | |
| 5,204,188 A | 4/1993 | Nitta et al. | |
| 5,260,333 A | 11/1993 | Lukacsko et al. | |
| 5,288,497 A | 2/1994 | Stanley et al. | |
| 5,364,616 A | 11/1994 | Singer et al. | |
| 5,373,022 A | 12/1994 | Fawzi et al. | |
| 5,409,709 A | 4/1995 | Ozawa et al. | |
| 5,417,980 A | 5/1995 | Goldman et al. | |
| 5,466,436 A | 11/1995 | Stables | |
| 5,514,663 A | 5/1996 | Mandel | |
| 5,601,843 A | 2/1997 | Gimet | |
| 5,631,022 A | 5/1997 | Mandel et al. | |
| 5,643,960 A | 7/1997 | Breitner et al. | |
| 5,667,802 A | 9/1997 | Grimberg | |
| 5,679,376 A | 10/1997 | Stevens et al. | |
| 5,686,105 A | 11/1997 | Kelm et al. | |
| 5,690,960 A | 11/1997 | Bengtsson et al. | |

(Continued)

FOREIGN PATENT DOCUMENTS

| | | |
|---|---|---|
| AU | 2006235929 | 11/2006 |
| CA | 2139653 | 7/2001 |

(Continued)

OTHER PUBLICATIONS

"A 12 month, phase 3, open-label, multi-center study to evaluate the long-term safety of PN 400," *ClinicalTrials.gov*, Sep. 11, 2007, accessed from <http://clinicaltrials.gov/ct2/show/NCT00527904> on Sep. 6, 2012.

"Arthrotec," medication guide distributed by G.D. Searle LLC, revised Aug. 2009.

"*Astrazeneca AB, Astrazeneca LP, KBI-E Inc., and Pozen, Inc.* v *Dr. Reddy's Laboratories Inc. and Dr. Reddy's Laboratories Ltd.*: Dr. Reddy's Laboratories Inc. and Dr. Reddy's Laboratories Ltd's. Invalidity contentions pursuant to L. Pat. R. 3.6(c)," dated Nov. 23, 2011.

"*Astrazeneca AB, Astrazeneca LP, KBI-E Inc., and Pozen, Inc.* v *Lupin Ltd. and Lupin Pharmaceuticals, Inc.*: Defendants Lupin Ltd. and Lupin Pharmaceuticals, Inc's Amended Invalidity Contentions Pursuant to L. PAT. R. 3.3 and 3.6(c)," dated Apr. 20, 2012.

(Continued)

*Primary Examiner* — Snigdha Maewall
(74) *Attorney, Agent, or Firm* — K&L Gates LLP

(57) ABSTRACT

The present disclosure is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof.

27 Claims, 4 Drawing Sheets

(56) References Cited

U.S. PATENT DOCUMENTS

| | | |
|---|---|---|
| 5,702,723 A | 12/1997 | Griffin |
| 5,714,504 A | 2/1998 | Lindberg et al. |
| 5,716,648 A | 2/1998 | Halskov et al. |
| 5,750,531 A | 5/1998 | Lee et al. |
| 5,817,338 A | 10/1998 | Bergstrand et al. |
| 5,817,340 A | 10/1998 | Roche et al. |
| 5,840,737 A | 11/1998 | Phillips |
| 5,872,145 A | 2/1999 | Plachetka |
| 5,877,192 A | 3/1999 | Lindberg et al. |
| 5,900,424 A | 5/1999 | Kallstrom et al. |
| 5,925,181 A | 7/1999 | Cook et al. |
| 5,955,451 A | 9/1999 | Lichtenberger et al. |
| 6,013,281 A | 1/2000 | Lundberg et al. |
| 6,025,395 A | 2/2000 | Breitner et al. |
| 6,040,315 A | 3/2000 | Day |
| 6,060,499 A | 5/2000 | Plachetka |
| 6,093,734 A | 7/2000 | Garst et al. |
| 6,132,768 A | 10/2000 | Sachs et al. |
| 6,132,771 A | 10/2000 | Depui et al. |
| 6,136,344 A | 10/2000 | Depui et al. |
| 6,162,816 A | 10/2000 | Bohlin et al. |
| 6,160,020 A | 12/2000 | Ohannesian et al. |
| 6,183,776 B1 | 2/2001 | Depui et al. |
| 6,183,779 B1 | 2/2001 | Ouali et al. |
| 6,207,188 B1 | 3/2001 | Gustavsson et al. |
| 6,231,888 B1 | 5/2001 | Lerner et al. |
| 6,287,600 B1 | 9/2001 | Ouali et al. |
| 6,365,184 B1 | 4/2002 | Depui et al. |
| 6,369,085 B1 | 4/2002 | Cotton et al. |
| 6,372,255 B1 | 4/2002 | Saslawski |
| 6,387,410 B1 | 5/2002 | Woolfe |
| 6,395,298 B1 | 5/2002 | Flanagan et al. |
| 6,428,810 B1 | 8/2002 | Bergstrand et al. |
| 6,485,747 B1 | 11/2002 | Flanagan et al. |
| 6,489,346 B1 | 12/2002 | Phillips |
| 6,544,556 B1 | 4/2003 | Chen et al. |
| 6,551,621 B1 | 4/2003 | Debregeas et al. |
| 6,599,529 B1 | 7/2003 | Skinhoj et al. |
| 6,610,323 B1 | 8/2003 | Lundberg et al. |
| 6,613,354 B2 | 9/2003 | Depui et al. |
| 6,632,451 B2 | 10/2003 | Penhasi et al. |
| 6,641,838 B2 | 11/2003 | Pather et al. |
| 6,645,988 B2 | 11/2003 | Phillips |
| 6,673,819 B2 | 1/2004 | Bergman et al. |
| 6,685,964 B1 | 2/2004 | Bartholomaeus et al. |
| 6,699,885 B2 | 3/2004 | Phillips |
| 6,713,089 B1 | 3/2004 | Bertelsen et al. |
| 6,749,867 B2 | 6/2004 | Robinson et al. |
| 6,780,882 B2 | 8/2004 | Phillips |
| 6,787,164 B2 | 9/2004 | Gelber et al. |
| 6,797,283 B1 | 9/2004 | Edgren et al. |
| 6,869,615 B2 | 3/2005 | Chen |
| 6,875,872 B1 | 4/2005 | Lindberg |
| 6,926,907 B2 | 8/2005 | Plachetka |
| 7,029,701 B2 | 4/2006 | Chen |
| 7,030,162 B2 | 4/2006 | Plachetka et al. |
| 7,060,694 B2 | 6/2006 | Plachetka et al. |
| 7,094,425 B2 | 8/2006 | Scott et al. |
| 7,332,183 B2 | 2/2008 | Plachetka et al. |
| 7,399,772 B2 | 7/2008 | Phillips |
| 7,411,070 B2 | 8/2008 | Cotton et al. |
| 7,488,497 B2 | 2/2009 | Depui et al. |
| 7,745,466 B2 | 6/2010 | Cotton et al. |
| 7,785,626 B2 | 8/2010 | Pettersson et al. |
| 7,846,914 B2 | 12/2010 | Petrus |
| 8,206,741 B2 | 6/2012 | Plachetka et al. |
| 2001/0025107 A1 | 9/2001 | Barberich et al. |
| 2001/0036473 A1 | 11/2001 | Scott et al. |
| 2001/0044410 A1 | 11/2001 | Gelber et al. |
| 2002/0012676 A1 | 1/2002 | Lundberg et al. |
| 2002/0042433 A1 | 4/2002 | Yelle et al. |
| 2002/0044962 A1 | 4/2002 | Cherukuri et al. |
| 2002/0045184 A1 | 4/2002 | Chen |
| 2002/0086029 A1 | 7/2002 | Lundberg et al. |
| 2002/0090395 A1 | 7/2002 | Woolfe et al. |
| 2002/0111370 A1 | 8/2002 | Bergman et al. |
| 2002/0155153 A1 | 10/2002 | Depui et al. |
| 2002/0160046 A1 | 10/2002 | Robinson et al. |
| 2003/0008903 A1 | 1/2003 | Barberich et al. |
| 2003/0040537 A1 | 2/2003 | Plachetka et al. |
| 2003/0113375 A1 | 6/2003 | Lundberg et al. |
| 2003/0129235 A1 | 7/2003 | Chen et al. |
| 2003/0215527 A1 | 11/2003 | Phillips |
| 2003/0232080 A1 | 12/2003 | Pather et al. |
| 2003/0232876 A1 | 12/2003 | Plachetka |
| 2004/0022846 A1 | 2/2004 | Depui et al. |
| 2004/0048896 A1 | 3/2004 | Phillips |
| 2004/0121004 A1 | 6/2004 | Taneja |
| 2004/0131676 A1 | 7/2004 | Taneja |
| 2004/0171646 A1 | 9/2004 | Phillips |
| 2004/0180089 A1 | 9/2004 | Plachetka et al. |
| 2005/0004171 A1 | 1/2005 | Phillips |
| 2005/0042304 A1 | 2/2005 | Phillips |
| 2005/0054682 A1 | 3/2005 | Phillips |
| 2005/0147668 A1 | 7/2005 | Bertelsen et al. |
| 2005/0163847 A1 | 7/2005 | Cheng et al. |
| 2005/0227949 A1 | 10/2005 | Edalatpour et al. |
| 2005/0249806 A1 | 11/2005 | Proehl et al. |
| 2005/0249811 A1 | 11/2005 | Plachetka |
| 2006/0165797 A1 | 7/2006 | Plachetka |
| 2006/0177504 A1 | 8/2006 | Sudharadas |
| 2006/0178348 A1 | 8/2006 | Plachetka |
| 2006/0178349 A1 | 8/2006 | Plachetka |
| 2006/0287284 A1 | 12/2006 | Schutze et al. |
| 2007/0122470 A1 | 5/2007 | Johansson et al. |
| 2007/0154542 A1 | 7/2007 | Tananbaum et al. |
| 2007/0184078 A1 | 8/2007 | Chen |
| 2007/0207200 A1 | 9/2007 | Plachetka et al. |
| 2007/0237820 A1 | 10/2007 | Cheng et al. |
| 2007/0243251 A1 | 10/2007 | Taneja |
| 2008/0031941 A1 | 2/2008 | Pettersson |
| 2008/0031950 A1 | 2/2008 | Sesha |
| 2008/0103169 A1 | 5/2008 | Phillips |
| 2009/0074863 A1 | 3/2009 | Taneja |
| 2009/0075950 A1 | 3/2009 | Taneja |
| 2009/0297594 A1 | 12/2009 | Depui et al. |
| 2010/0062064 A1 | 3/2010 | Ault et al. |
| 2010/0172983 A1 | 7/2010 | Plachetka |
| 2010/0178334 A1 | 7/2010 | Johansson et al. |
| 2010/0330179 A1 | 12/2010 | Ault et al. |
| 2011/0008432 A1 | 1/2011 | Plachetka |

FOREIGN PATENT DOCUMENTS

| | | |
|---|---|---|
| DE | 40 35 455 | 5/1992 |
| DE | 198 01 811 | 7/1999 |
| EP | 0 005 129 A1 | 10/1979 |
| EP | 0 005 129 B1 | 4/1981 |
| EP | 0 124 495 A2 | 11/1984 |
| EP | 0 166 287 A1 | 1/1986 |
| EP | 0 167 958 A2 | 1/1986 |
| EP | 0 174 726 A1 | 3/1986 |
| EP | 0 244 380 A2 | 11/1987 |
| EP | 0 174 726 B1 | 4/1989 |
| EP | 0 320 550 A1 | 6/1989 |
| EP | 0 320 551 A1 | 6/1989 |
| EP | 0 426 479 A1 | 5/1991 |
| EP | 0 244 380 B1 | 1/1993 |
| EP | 0 550 083 A1 | 7/1993 |
| EP | 0 426 479 B1 | 2/1994 |
| EP | 0 550 083 B1 | 3/1999 |
| EP | 1 020 461 A2 | 7/2000 |
| EP | 1 068 867 A2 | 1/2001 |
| EP | 1 726 300 A1 | 11/2006 |
| EP | 1 726 301 A1 | 11/2006 |
| GB | 2 105 193 | 3/1983 |
| GB | 2 163 747 | 5/1986 |
| GB | 2 216 413 | 10/1989 |
| JP | 2005-145894 | 6/2005 |
| WO | WO 1985/003443 | 8/1985 |
| WO | WO 1990/006925 | 6/1990 |
| WO | WO 1991/016886 | 11/1991 |
| WO | WO 1991/016895 | 11/1991 |
| WO | WO 1991/016896 | 11/1991 |

(56) References Cited

FOREIGN PATENT DOCUMENTS

| | | |
|---|---|---|
| WO | WO 1991/019711 | 12/1991 |
| WO | WO 1991/019712 | 12/1991 |
| WO | WO 1993/011750 | 6/1993 |
| WO | WO 1993/012817 | 7/1993 |
| WO | WO 1994/007541 | 4/1994 |
| WO | WO 1994/027988 | 12/1994 |
| WO | WO 1995/001977 | 1/1995 |
| WO | WO 1995/032959 | 12/1995 |
| WO | WO 1996/005177 | 2/1996 |
| WO | WO 1996/005199 | 2/1996 |
| WO | WO 1996/014839 | 5/1996 |
| WO | WO 1996/022780 | 8/1996 |
| WO | WO 1997/011701 | 4/1997 |
| WO | WO 1997/025064 | 7/1997 |
| WO | WO 1998/054171 | 3/1998 |
| WO | WO 1998/013073 | 4/1998 |
| WO | WO 1998/022117 | 5/1998 |
| WO | WO 1998/022118 | 5/1998 |
| WO | WO 1999/012524 | 3/1999 |
| WO | WO 1999/029320 | 6/1999 |
| WO | WO 1999/000380 | 7/1999 |
| WO | WO 1999/066919 | 12/1999 |
| WO | WO 2000/001368 | 1/2000 |
| WO | WO 2000/015195 | 3/2000 |
| WO | WO 2000/056339 | 9/2000 |
| WO | WO 2000/071122 | 11/2000 |
| WO | WO 2000/072838 | 12/2000 |
| WO | WO 2000/078293 | 12/2000 |
| WO | WO 2001/024777 | 4/2001 |
| WO | WO 2001/066088 | 9/2001 |
| WO | WO 2002/022108 | 3/2002 |
| WO | WO 2002/066002 | 8/2002 |
| WO | WO 2002/098352 | 12/2002 |
| WO | WO 2003/017980 | 3/2003 |
| WO | WO 2004/062552 | 7/2004 |
| WO | WO 2004/064815 | 8/2004 |
| WO | WO 2004/106381 | 12/2004 |
| WO | WO 2005/074536 | 8/2005 |
| WO | WO 2005/074930 | 8/2005 |
| WO | WO 2006/044202 | 4/2006 |
| WO | WO 2007/064274 | 6/2007 |
| WO | WO 2007/078874 | 7/2007 |
| WO | WO 2008/101060 | 8/2008 |
| WO | WO 2009/012393 | 1/2009 |
| WO | WO 2009/145905 | 12/2009 |
| WO | WO 2010/151697 | 12/2010 |

OTHER PUBLICATIONS

"Astrazeneca AB, Astrazeneca LP, KBI-E Inc., and Pozen, Inc. v Lupin Ltd. and Lupin Pharmaceuticals Inc.,: Defendants Lupin Ltd. and Lupin Pharmaceuticals, Inc.'s Invalidity Contentions Pursuant to L. Pat. R. 3.3 and 3.6(c)," dated Nov. 23, 2011.
"Astrazeneca AB, Astrazeneca LP, KBI-E Inc., and Pozen, Inc. v. Anchen Pharmaceuticals, Inc.: Anchen's Initial Invalidity Contentions," dated May 11, 2012.
"Astrazeneca AB, Astrazeneca LP, KBI-E Inc., and Pozen, Inc. v. Dr. Reddy's Laboratories Inc. and Dr. Reddy's Laboratoriese Ltd.: Plaintiffs' Response to DRL's First Set of Interrogatories to Plaintiffs (Nos. 1-5)," dated Mar. 5, 2012.
"Astrazeneca submits marketing authorisation application to European union for vimovo," Astrazeneca, Oct. 16, 2009.
"Detailed Factual that the Claims of and Legal Bases for Teva Pharmaceuticals USA's Paragraph IV Certification the the Claims of U.S. Pat. Nos. 6,926,907, 8,206,741, and 9,364,439 are Invalid, Unenforceable, and/or Not Infringed," Teva Pharmaceuticals USA, Dec. 9, 2016.
"Histamine H2 antagonist," accessed from <drugs.com> on Sep. 6, 2012.
Notice of Paragraph IV Certification Re: Dr. Reddy's Laboratories, Ltd.'s and Dr. Reddy's Laboratories, Inc.'s Naproxen and Esomeprazole Magnesium Delayed Release Tablets; U.S. Pat. No. 6,926,907, from Dr. Reddy's Laboratories, Ltd./Dr. Reddy's Laboratories, Inc., dated Mar. 11, 2011.

"PK Study to evaluate esomeprazole plasma levels following the administration of PN 400," ClinicalTrials.gov, Jan. 11, 2008, accessed from, <http://clinicaltrials.gov/ct2/show/NCT00599404> on Sep. 6, 2012.
"Study evaluating the bioavailability of Naproxen 500 mg in three formulations," ClinicalTrials.gov, Apr. 23, 2008, accessed from , <http://clinicaltrials.gov/ct2/show/NCT00665743>, on Sep. 6, 2012.
Abelo et al., "Pharmacodynamic modelling of reversible gastric acid pump inhibition in dog and man," Eur J Pharm Sci, 14(4):339-346, 2001.
Abraham et al., "ACCF/ACG/AHA 2010 expert consensus document on the concomitant use of proton pump inhibitors and thienopyridines: a focused update of the ACCF/ACG/AHA 2008 expert consensus document on reducing the gastrointestinal risks of antiplatelet therapy and NSAID use," Journal of the American College of Cardiology, 56(24):2051-66, 2010.
Alberts et al., "Efficacy and safety of PA, a novel combination of enteric-coated acetylsalicylic acid and immediate-release omeprazole," Abstract P507, Stroke, 40:e104-276, 2009.
Alexander et al., "Pilot evaluation of a novel combination table (PN 400) containing a proton pump inhibitor and a nonsteroidal anti-inflammatory drug in prevention of upper gastrointestinal mucosal injury," American Jounral of Gastroenterology, 100(9), S68, 135, 2005
Andersson, "Pharmacokinetics, metabolism and interactions of acid pump inhibitors," Clin. Pharmacokinet., 31(1):9-28, 1996.
Awtry et al., "Aspirin," Circulation, 101:1206-1218, 2000.
Bajbouj et al., "A prospective multicenter clinical and endoscopic follow-up study of patients with gastroesophageal reflux disease," Z. Gastroenterol., 43:1303-1307, 2005.
Ballinger et al., "COX-2 inhibitors versus NSAIDs in gastrointestinal damage and prevention," Exp. Opin. Pharmacother., 2(1):31-40, 2001.
Barnett et al., "Effects of SCH 32651 on resting and stimulated acid secretion in guinea-pig isolated fundic mucosa," Br. J. Pharmac., 83:075-082, 1984.
Berardi et al,. "Elevation of gastric pH with rantidine does not affect the release characteristics of sustained release ibuprofen tablets," Biopharmaceutics & Drug Disposition, 9:337-347, 1998.
Bergman et al., "Protection against aspirin-induced gastric lesions by lansoprazole: simultaneous evaluation of function and morphologic responses," Clin Pharmacol Ther., 52(4):413-416, 1992.
Bianchi Porro et al., "Pantoprazole versus placebo in prevention of NSAID-induced ulcers," Gastroenterology, 114(4):A74, 1998.
Bianchi Porro et al., "Prevention of gastroduodenal damage with omeprazole in patients receiving continuous NSAIDs treatment. A double blind placebo controlled study," Ital. J. Gastroenterol. Hepatol., 30:43-47, 1998.
Bianchi Porro et al., "Why are non-steroidal anti-inflammatory drugs important in peptic ulcers?" Aliment. Pharmacol. Therap., 1:540S-547S, 1987.
Bigard et al., "Complete prevention by omeprazole of aspirin induced gastric lesions in healthy subjects," GUT, 29(5): A712, T49, 1988.
Bigard et al., "Effet protecteur de l'omeprazole sur les lesions gastriques induites par une prise unique d'aspirine chez l'homme," Gastroenterol. Clin. Biol., 12:770-771, 1998. (English Translation included).
Bombardier et al., "Comparison of upper gastrointestinal toxicity of rofecoxib and naproxen in patients with rheumatoid arthritis," N. Engl. J. Med., 343:1520-1528, 2000.
Brown et al., "Aspirin- and indomethacin-induced ulcers and their antagonism by antihistamines," Euro. J. Pharm., 51:275-283, 1978.
Brown et al., "Prevention of gastrointestinal adverse effects of nonsteroidal anti-inflammatory drugs," Pract. Drug Safety, 21: 503-512, 1999.
Byrn et al., "Pharmaceutical solids: A strategic approach to regulatory considerations," Pharm. Res., 12(7): 945-954, 1995.
Carrasco-Portugal et al., "Bioavailability of a formulation containing a diclofenac-rantidine combination," Proc. West. Pharmacol. Soc., 45:8-10, 2002.
Cederberg et al., "Omeprazole: Pharmacokinetics and metabolism in man," Scand. J. Gastroenterol., 24(S166):33-40, 1989.

(56) References Cited

OTHER PUBLICATIONS

Chan et al.,"Clopidogrel versus Aspirin and Esomeprazole to prevent recurrent ulcer bleeding," *New Eng. J. Med.*, 352:238-244, 2005.

Chan et al., "Eradication of H. Pylori versus maintenance acid suppression to prevent recurrent ulcer hemorrhage in high risk NSAID users: A prospective randomized study," *Gastroenterology*, 114: A87, G0356, 1998.

Chandramouli and Tolman, "Prevention and management of NSAID-induced gastropathy," *Jounral of Pharmaceutical Care in Pain & Symptom Control*, 8(4): 27-40, 2000.

Chang et al., "Polymetharcrylates," Handbook of Pharmaceutical Excipients, Fifth Edition, Ed. Raymond C. Rowe, Paul J. Sheskey and Sian C. Owen, London: Pharmaceutical Press, 553-560, 2006.

Chen et al., "Esomeprazole tablet vs. omeprazole capsule in treating erosive esophagitis," *World Journal of Gastroenterology*, 11(20):3112-3117, 2005.

ClinicialTrials Identifier: NCT00961350, "A 6-Month, Phase 3, Randomized, Double-Blind, Parallel-Group, Controlled, Multi-Center Study to Evaluate the Incidence of Gastric Ulcers Following Administration of Either PA32540 or Enteric Coated Aspirin 325 mg in Subjects Who Are at Risk for Developing Aspirin-Associated Ulcers," study sponsored by POZEN, Apr. 21, 2010.

Cullen et al., "Primary gastroduodenal prophylaxis with omeprazole for no-steroidal anti-inflammatory drug users," *Aliment. Pharmacol. Ther.*, 12:135-140, 1998.

Dajani, "Perspective on the gastric antisecretory effects of misoprostol in man," *Prostaglandins*, 33:68-77, 1987.

Daneshmend et al., "Abolition by omeprazole of aspirin induced gastric mucosal injury in man," *Gut*, 34:514-517, 1990.

Daneshmend et al., "Use of microbleeding and an ultrathin endoscope to assess gastric mucosal protection by famotidine," *Gastroenterology*, 97:944-9, 1989.

Dent, "Why protein pump inhibition should heal and protect against nonsteroidal anti-inflammatory drug ulcers," *Am. J. Med.*, 104:52S-55S, 1998.

Dent, "Why proton pump inhibition should heal and protect against nonsteroidal anti-inflammatory drug ulcers," *Am. J. Med.*, 104(3A):52S-55S, Discussion 79S-80S, 1998.

Du et al., "Pharmacokinetics and bioavailability of aspirin enteric-coating tablet and controlled-release capsule in man," *China Pharmacy*, 1998. Available online at http://en.cnki.com.cn/Article_en/CJFDTOTAL-ZGYA199802015.htm. (English abstract of Chinese publication).

Eccles et al., "North of England evidence based guideline development project: guideline on the use of aspirin as secondary prophylaxis for vascular disease in primary care. North of England Aspirin Guideline Development Group," *Brit. Med. J.*, 316(7140):1303-1309, 1998.

Ehsanullah et al., "Prevention of gastroduodenal damage induced by non-steroidal anti-inflammatory drugs: controlled trial of ranitidine," *BMJ*, 297:1017-1021, 1988.

Ekstrom et al., "Prevention of peptic ulcer and dyspeptic symptoms with omeprazole in pateitns receiving continuous non-steroidal anti-inflammatory drug therapy," *Scand. J. Gastroenterol.*, 31:753-758, 1996.

Ene et al., "A study of the inhibitory effects of SCH 28080 on gastric secretion in man," *Br. J. Pharmac.*, 76:389-391, 1982.

Erlandsson et al., "Resolution of the enantiomers of omeprazole and some of its analogues by liquid chromatography on a trisphenycarbamoylcellulose-based stationary phase,"*J. Chromatog.*, 532:305-319, 1990.

European Search Report issued in European Patent Application No. 09178773, dated Feb. 11, 2010.

Extended European Search Report issued in European Patent Application No. 12861429.4, dated Aug. 18, 2015.

Fass, "Erosive Esophagitis and Nonerosive Reflux Disease (NERD): Comparison of Epidemiologic, Physiologic, and Therapeutic Characteristics," *J. Clin. Gastroenterol.*, 41(2):131-137, 2007.

Feldman and Carlstedt, "Effect of antacid on absorption of enteric-coated aspirin," *JAMA*,.227(6):660-1, 1974.

Florence and Jani, "Novel oral drug formulations their potential in modulating adverse effects," *Drug Safety*, 10(3):233-66, 1994.

Fort et al., "PA, a novel combination of delayed release (DR) acetylsalicylic acid (ASA) and immediate-release (IR) omeprazole, is associated with a decreased risk of gastroduodenal mucosal injury: pooled data from three phase 1, 4-week endoscopic studies" Abstract 1246, *Am J Gastroenterol.*, 103:S487-S488, 2008.

Frank et al., "Reduction of indomerthacin induced gastrduodenal muclosal injury and gastrointestinal symptoms with cimetidine in normal subjects," *J. Rheum.*, 16:1249-1252, 1989.

Gengo et al., "Prevalence of platelet nonresponsiveness to aspirin in patients treated for secondary stroke prophylaxis and in patients with recurrent isochemic events," *J. Clin. Pharmacol.*, 48:335-343, 2008.

Goldstein et al, "PN400 significantly reduces the incidence of gastric ulcers compared with enteric-coated naproxen in patients requiring chronic NSAID therapy regardless of low-dose aspirin use: Results from two prospective, randomized controlled trials," POZEN Inc. sponsored study, 2009. (Document D16 from Letter to European Patent Office for counterpart European Application No. 02 734 602.2, regarding Oral Proceedings dated Dec. 18, 2009).

Goldstein et al., "116 A single table multilayer formulation of enteric-coated naproxen coupled with no-enteric-coated omeprazole is associated with a significantly reduced incidence of gastric ulcers vs. enteric-coated naproxen: A prospective, randomized double-blind study," 134(4), Supplement 1, A-19, 2008.

Goldstein et al., "PA32540 (Enteric-coated aspirin 325 mg + immediate-release omeprazole 40mg) is associated with significantly fewer gastric ulcers and significantly less endoscopic erosive esophagitis than enteric-coated aspirin (EC-ASA) alone: Results of two phase 3 studies," *The American Journal of Gastroenterology*, vol. 107, Suppl. 1, pp. S53-S54, 2012.

Goldstein et al., "PN400 significantly improves upper gastrointestinal tolerability compared with enteric-coated naproxen alone in patients requiring chronic NSAID therapy: Results from Two Prospective, Randomized, Controlled Trials," POZEN Inc. sponsored study, 2009. (Document D15 from Letter to European Patent Office for counterpart European Application No. 02 734 602.2, regarding Oral Proceedings dated Dec. 18, 2009).

Graham et al., "Duodenal and gastric ulcer prevention with misoprostol in arthritis pateitns taking NSAIDs," *Ann. Intern. Med.*, 119(4):257-262, 1993.

Grosser et al., "Thromboxane generation," In Platelets, Alan Michelson Ed., pp. 565-574, Elseiver Science, 2007.

Gurbel et al., "PA32520 (single-tablet of enteric-coated acetylsalicylic acid 325 mg + immediate-release omeprazole 20 mg): acetylsalicylic acid therapy combining greater thromboxane suppression and lower upper gastrointestinal damage," Abstract 4267, *Circulatio*, 118:S855, 2008.

Gurbel et al., "Pharmacodynamic Evaluation of Clopidogrel Plus PA32540: The Spaced PA32540 with Clopidogrel Interaction Gauging (SPACING) Study," *Clinical Pharmacology & Therapeutics*, 90(6):860-866, 2011.

Hart et al., "Aspirin dosage and thromboxane synthesis in patients with vascular disease," *Pharmacotherapy*, 23(5):579-584, 2003.

Hassan-Alin et al., "Lack of drug-drug interaction between esomeprazole and naproxen in healthy subjects," *Gastroenterology*, 124(4), Supp. 1, A541, 2003.

Hawkey et al, "Omeaprazole compared with misoprostol for ulcers associated with nonsteroidal anti-inflammatory drugs," *N. Engl. J. Med.*, 338:727-734, 1998.

Hawkey et al., "Prophylaxis of aspirin-induced gasf ric mucosal bleeding with ranitidine," *Aliment. Pharmacol. Therap.*, 2:245-252, 1988.

Hawkey et al., "Strategies for preventing aspirin-induced gastric bleeding," *Scand J Gastroenterol Suppl.*, 125:170-173, 1986.

Hawkey, "Non-steroidal anti-inflammatory drug gastropathy: causes and treatment," *Scan. J. Gastroenterol.*, 31 Suppl. 220:124-7, 1996.

Hawkey, "Progress in prophylaxis against nonsteroidal anti-inflammatory drug-associated ulcers and erosions," *Am J. Med.*, 104:67S-74S, 1998.

(56) References Cited

OTHER PUBLICATIONS

Hawkins et al., "The Gastroduodenal Toxicity of Nonsteroidal Anti-Inflammatory Drugs. A Review of the Literature," *J. Pain and Symptom Management*, 20(2):140-151, 2000.
Helander et al., "Structure and function of rat parietal cells during treatment with omeprazole, SCH 28080, SCH 32651, or ranitidine," *Scand J Gastroenterol.*, 25(8): 799-809, 1990.
Hogan et al., "Prescription of nonsteroidal anti-inflammatory drugs for elderly people in Alberta," *Can. Med. Assoc.*, 151(3):315-322, 1994.
Horn and Howden, "Review article: Similarities and differences among delayed-release proton-pump inhibitor formulations," *Aliment Pharmacol Ther.*, 22 Suppl 3:20-24, 2005.
Howden, "Clinical pharmacology of omeprazole," *Clin. Pharmacokinet.*, 20:38-49, 1991.
Howden, "Review article: immediate-release proton-pump inhibitor therapy—potential advantages," *Aliment Pharmacol Ther.*, 22 Suppl 3:25-30, 2005.
Ife et al., "Reversible inhibitors of the Gastric (H+/K+)-ATPase. 3. 3-substituted-4-(phenylamino) quinolines," *J. Med. Chem.*, 35:3413-3422, 1992.
Jacques et al., "Final purification, enrichment, of partially resolved enantiomer mixtures," In Enantiomers, Racemates, and Resolutions, 423-434, 1981.
Jiranek et al., "Misoprostol reduces gastroduodenal injury from one week of aspirin: An endoscopic study," *Gastroenterology*, 96:656-661, 1989.
Johnson et al., "Esomeprazole once daily for 6 months is effective therapy for maintaining healed erosive esophagitis and for controlling gastroesophageal reflux disease symptoms: A randomized, double-blind, placebo-controlled study of efficacy and safety," *The American Journal of Gastroenterology*, 96(1):27-34, 2001.
Katz et al., "Gastric acidity and acid breakthrough with twice-daily omeprazole or lansoprazole," *Aliment. Pharmacol. Ther.*, 14:709-714, 2000.
Keeling et al., "SK&F 96067 is a reversible, lumenally acting inhibitor of the gastric (H++K+)-ATPase," *Biochem Pharmacol.*, 42(1): 123-130, 1991.
Kephart et al., "Coprescribing of nonsteroidal anti-inflammatory drugs and cytoprotective and antiulcer drugs in Nova Scotia's senior population," *Clin. Ther.* 17:1159-1173, 1995.
Kimmey et al., "Role of H$_2$-receptor blockers in the prevention of gastric injury resulting from nonsteroidal anti-inflammatory agents," *Am. J. Med.*, 84:49-52, 1988.
Kitchingman et al., "Enhanced gastric mucosal bleeding with doses of aspirin used for prophylaxis and its reduction by rantidine," *Br. J. Clin. Pharmac.*, 28:581-585, 1989.
Konturek et al., "Effects of omeprazole, a substituted benzimidazole, on gastrointestinal secretions, serum gastrin, and gastric mucosal blood flow in dogs," *Gastroenterology*, 86(1):71-77, 1984.
Labenz et al., "Risk factors for erosive esophagitis: A multivariate analysis based on the proGERD study initiative," *American Journal of Gastroenterology*, 99:1652-1656, 2004.
Lad et al., "Management of nonsteroidal anti-inflammatory drug-induced gastroduodenal disease by acid suppression," *Can. J. Gastroenterol.*, 13:135-142, 1999.
Lanas, "Prevention of aspirin-induced gastroduodenal damage: H. Pylori infection eradication versus proton pump inhibitors of both," *Digestive and Liver Disease*, 36:655-657, 2004.
Lanza et al., "A double-blind placebo-controlled comparison of the efficacy and safety of 50, 100, and 200 μg of misoprostol QID in the prevention of ibuprofen-induced gastric and duodenal mucosal lesions and symptoms," *Am. J. Gastroenterol.*, 84(6):633-636, 1989.
Lanza et al., "Double-blind, placebo-controlled endoscopic comparison of the mucosal protective effects of misoprostol versus cimetidine on tolmetin-induced injury to the stomach and duodenum," *Gastroenterology*, 95:289-294, 1988.
Larsson et al., "Animal pharmacodynamics of omeprazole. A survey of its pharmacological properties in vivo," *Scand J Gastroenterol Suppl.*, 108:23-35, 1985.
Lee et al., "Omeprazole prevents indomethacin-induced gastric ulcers in rabbits" *Aliment. Pharmacol. Ther.*, 10:571-576, 1996.
Leese et al., "Effects of celecoxib, a novel cyclooxygenase-2 inhibitor, on platelet function in healthy Adults: A randomized, controlled trial," *J. Clin. Pharmacol.*, 40:124-132, 2000.
Leonards and Levy, "Reduction or prevention of aspirin-induced occult gastrointestinal blood loss in man," *Clinical Pharmacology and Therapeutics*, 10(4):571-5, 1969.
Letter to European Patent Office for European Application No. 02 734 602.2, regarding Oral Proceedings dated Dec. 18, 2009.
Lichtenberger et al., "Nonsteroidal anti-inflammatory drug and phospholipid prodrugs: combination therapy with antisecretory agents in rats," *Gastroentereology*, 111:990-995, 1996.
Lin and Lu, "Role of pharmacokinetics and metabolism in drug discovery and development," *Pharmacological Reviews*, 49(4):403-449, 1997.
Maggi et al., "Press-coated tablets for the sequential pulsed administration of two different drugs," *Int. J. Pharm.*, 99:173-179, 1993.
Mason and Winer, "Kinetics of aspirin, salicylic acid, and salicyclic acid, and salicyluric acid following oral administration of aspirin as a tablet and two buffered solutions," *Journal of Pharmaceutical Sciences*, 70(3):262-5, 1981.
Mattsson et al., "Omeprazole provides protection agains experimentally induced gastric mucosal lesions," *Eur. J. Pharmacol.*, 91:111-114, 1983.
McKeage et al., "Esomeprazole: a review of its use in the management of gastric acid-related diseases in adults," *Drugs*, 68(11):1571-15607, 2008.
Miner et al., "Clinical trial: evaluation of gastric acid suppression with three doses of immediate-release esomeprazole in the fixed-dose combination of PN 400 (naproxen/esomeprazole magnesium) compared with naproxen 500 mg and enteric-coated esomeprazole 20 mg: a randomized, open-label, Phase I study in healthy volunteers," *Aliment. Pharmacol. Ther.*, 32(3):414-424, 2010.
Miner et al., "PA32540, a tablet containing enteric-coated (EC) aspirin 325 mg and unbuffered immediate-release omeprazole 40 mg, provides percent time gastric pH >4 significantly less than EC omeprazole 40 mg, but faster onset and less exposure to omeprazole," *Gastroenterology*, vol. 142, Issue 5, Supplement 1, p. S-3, 2012.
Miner et al., "T1969 Gastric acid suppression with PN400, a single-tablet, multilayer, fixed dose formulation combining an immediate-release esomeprazole layer and an enteric-coated (EC) naproxen core," *Gastroenterology*, 136(5), Suppl. 1, A-611, 2009.
Miner et al., "T1972 Pharmacokinetics of naproxen and esomeprazole in pn400, a single-tablet, multilayer formulation of enteric-coated naproxen coupled with immediate-release esomeprazole," *Gastroenterology*, 136(5), Suppl. 1, A-612, 2009.
Morgner et al., "Esomeprazole: prevention and treatment of NSAID-induced symptoms and ulcers," *Expert Opin Pharmacother.*, 8(7):975-988, 2007.
Morris et al., "Gastric cytoprotection is secondary to increased mucosal fluid secretion: A study of six cytoprotective agents in the rat," *J. Clin. Gastroenterol.*, 27(Suppl. 1):S53-63, 1998.
Morrison et al., "The optimal analgesic dose of rofecixib," *JADA*, 131(12): 1729-1737, 2000.
Muir et al., "Comparative bioavailability of aspirin and paracetamol following single dose administration of soluble and plain tablets," *Current Medical Research and Opinion*, 13(9):491-500, 1997.
Muller et al., "Untersuchungen zur schutzwirkung von lansoprazol auf die menschliche magenschleimhaut gegenuber niedrig dosierter acetylsalicylsaure," *Arzneimittel Forschung*, 47:758-760, 1997. (English translation enclosed).
Muller et al., "Velbesserung der gastroduodenalen vertraglichkeit von azetylsalizylsaure durch ranitidine," *Arzneimittel-Forschung/Drug Res.*, 41(1):638-639, 1991. (English translation enclosed).
Naesdal and Wilson, "Gastro-duodenal protection in and era of cyclo-oxygenase-2-selective nonsteroidal anti-inflammatory drugs," *Eur. J. Gastroenterol.*, 13(12): 1401-1406, 2001.
Needs et al., "Clinical pharmacokinetics of the salicylates," *Clinical Pharmacokinetics*, 10:164-177, 1985.
Nefesoglu et al., "Interaction of omeprazole with enteric-coated Salicylate tablets," *International Journal of Clinical Pharmacology and Therapeutics*, 36(10):549-553, 1998.

(56) References Cited

OTHER PUBLICATIONS

Neuvonen and Kivisto, "Enhancement of drug absorption by antacids," *Clin. Pharmacokinet.*, 27(2):120-8, 1994.
Notice of Opposition to a European Patent, submitted against European Patent application No. EP 1 411 900 on Apr. 15, 2011.
Notice of Opposition to a European Patent, submitted against European Patent application No. EP 1 411 900 on Apr. 21, 2011.
Oddsson et al., "Comparison between ranitidine and omeprazole for protection against gastroduodenal damage caused by naproxen," *Scand. J. Gastroenterol.*, 27:1045-1048, 1992.
Oddsson et al., "Endoscopic findings in the stomach and duodenum after treatment with enteric-coated and plain naproxen tablets in healthy subjects," *Scand. J. Gastroenterol.*, 25:231-234, 1990.
Office Communication issued in Chinese Patent Application No. 201280065623.6, dated Mar. 4, 2016. (English translation of Chinese text).
Office Communication issued in Egyptian Patent Application No. 2121/2011, dated Apr. 13, 2013. (English summary of Arabic text).
Office Communication issued in United Arab Emirates Patent Application No. 0693/2014, dated Jan. 10, 2017.
Office Communication issued in Eurasian Patent Application No. 201491285, dated Jul. 7, 2016. (English translation of Russian text).
Office Communication issued in Eurasian Patent Application No. 201491285, dated Nov. 20, 2015. (English translation of Russian text).
Office Communication issued in European Patent Application 10177150.9, dated Nov. 12, 2010.
Office Communication issued in European Patent Application No. 02734602.2, dated Feb. 22, 2010.
Office Communication issued in European Patent Application No. 02734602.2, dated Apr. 29, 2010.
Office Communication issued in European Patent Application No. 0273602.2, dated Jun. 21, 2010.
Office Communication issued in U.S. Appl. No. 15/338,825, dated Jul. 3, 2017.
Office Communication issued in Ukrainian Patent Application No. a 2014 08511, dated Nov. 18, 2016. (English translation of Russian text).
Office Communication issued in U.S. Appl. No. 14/367,972, dated Feb. 25, 2016.
Okabe et al., "Antisecretory effect of leminoprazole on histamine-stimulated gastric acid secretion in dogs: potent local effect," *Jpn. J. Pharmacol.*, 96:91-100, 1995.
Okabe et al., "Pharmacological regulation of gastric acid secretion in the apical membrane of parietal cells; a new target for antisecretory drugs," Journal of Physiology and Pharmacology, 52(4):639-656, 2001.
Panara et al., "Effects of novel anti-inflammatory compounds, N-[2-(cyclohexyloxy)-4-nitrophenyl] methanesulphonamide (NS-398) and 5-methanesulphonamido-6-(2,4-difluorothio-phenyl)-1-inda none (L-745,337), on the cyclo-oxygenase activity of human blood prostaglandin endoperoxide synthases," *Br J Pharmacol.*, 116(5): 2429-2434, 1995.
Pang et al., "Modeling of intestinal drug absorption: roles of transporters and metabolic enzymes (for the Gillette review series)" *Drug Metabolism and Disposition*, 31(12): 1507-1519, 2003.
Patrono et al., "Low-dose aspirin for the prevention of Atherothrombosis," *New Eng. J. Med.*, 353:2373-2383, 2005.
PCT International Preliminary Report on Patentability issued in International Patent Application No. PCT/US2009/003281, dated Nov. 30, 2010.
PCT International Search Report and Written Opinion issued in International Patent Application No. PCT/US2012/071759, dated Mar. 5, 2013.
PCT International Search Report and Written Opinion issued in International Patent Application No. PCT/US2010/39864, dated Aug. 30, 2010.
PCT International Search Report issued in International Patent Application No. PCT/US2002/17105, dated Mar. 14, 2003.
Peterson, "Doubts are raised on the safety of 2 popular arthritis drugs," New York Times, May 22, 2001.
Pilbrant et al., "Development of an oral formulation of omeprazole," *Scan. J. Gastroenterol.* 20(Suppl. 108): 113-120, 1985.
Pirmohamed et al., "Adverse drug reactions as cause of admission to hospital: prospective analysis of 18,820 patients," *Br. Med. J.*, 329:15-19, 2004.
Porter S.C., "Coating of Pharmaceutical Dosage Forms," in: A. Gennaro (Ed.), *Remington: The Science and Practice of Pharmacy*, 19th edition. pp. POZNP0024US_REFC1650-1651, 1995.
Qureshi et al., "Pharmacokinetixs of two enteric-coated ketoprofen products in humans with or without coadministration of omeprazole and comparison with dissolution findings," *Pharm. Res.*, 11(11): 1669-1672, 1994.
Ramage et al., "Inhibition of food stimulated acid secretion by misoprostol, an orally active synthetic E1 analogue prostaglandin," *Br. J. Clin Pharmac.*, 19:9-12, 1985.
Raskin et al., "Misroprostol dosage in the prevention of nonsteroidal anti-inflammatory drug-induced gastric and duodenal ulcers: a comparison of three regimens," *Ann. Intern. Med.*, 123(5):344-350, 1995.
*Remington's Pharmaceutical Sciences*, 17th ed., University of Sciences in Philadelphia, 1985.
Response to Office Communication filed in European Patent Application No. 02734602.2, dated May 10, 2010.
Richardson et al., "Proton pump inhibitors, pharmacology and rationale for use in gastrointestinal disorders," *Drugs*, 56(3):307-335, 1998.
Robinson et al., "Effects of ranitidine gastroduodenal mucosal damage induced by nonsteroidal anti-inflammatory drugs," *Dig. Disc. Sci.*, 34(3):424-428, 1989.
Roche Naprosyn, EC label, copyright 1999.
Roth et al., "Cimetidine therapy in nonsteroidal anti-inflammatory drug gastropathy: double-blind long-term evaluation," *Arch. Intern. Med.*, 147:1798-1801, 1987.
Rubinstein, "Gastrointestinal anatomy physiology and permeation pathways," *Enhancement in Drug Discovery*, CRC Press, 3-35, 2007.
Sangiah et al., "Effects of misoprostol and omeprazole on basal gastric pH and free acid content in horses," *Res. Vet. Sci.*, 47(3):350-354, 1989.
Savarino et al., "Effect of one-month treatment with nonsteroidal anti-inflammatory drugs (NSAIDs) on gastric pH of rheumatoid arthritis patients," *Digestive Diseases and Sciences*, 43:459-463, 1998.
Scarpignato et al., "Prevention and treatment of non-steroidal anti-inflammatory drug-induced gastro-duodenal damage: Rationale for the use of antisecretory compounds," *Ital. J. Gastroenterol. Hepatol.*, 31(Supp. 1):S63-72, 1999.
Scarpignato et al., "Towards a GI safer anti-inflammatory therapy," *Gastroenterology International*, 186-215, 1999.
Scheiman et al., "Omeprazole ameliorates aspirin-induced gastroduodenal injury," *Dig. Dis.*, 39:97-103, 1994.
Scheiman, "NSAID-Induced peptic ulcer disease: a critical review of pathogenesis and management," *Dig Dis.*, 12:210-222, 1994.
Scheiman, "Pathogenesis of gastroduodenal injury due to nonsteroidal and anti-inflammatory drug: Implications for prevetion and therapy," *Seminars in Arthrisits and Rheumatism*, 21(4):201-210, 1992.
Schepp, "Proton pump inhibitory therapy: Then and Now," *Yale J. Biology and Medicine*, 69:175-186, 1996.
Scott and Sundel, "Inhibition of H+ K+ ATPase BY SCH 28080 and SCH 32651," *Eur J Pharmacol.*, 112:268-270, 1985.
Seitz et al., "Tablet Coating," *Theory and Practice of Industrial Pharmacy*, Ed. Leon Lachman et al., Philadelphia, 346-373, 1986.
Selway, "Potential hazards of long-term acid suppression ," *Scand. J. Gastroenterol.*, 25(Supp 178): 85-92, 1990.
Sharma, "Comparison of 24-hour intragastic pH using four liquid formulations of lanzsopmzole and omeprazole," *Am. J. Health-Syst. Pharm.*, 56(Supp. 4): S18-S21, 1999.
Silverman, *The Organic Chemistry of Drug Design and Drug Action*, 2nd Edition, Academic Press, p. 102 & p. 527, 2004.

(56) References Cited

OTHER PUBLICATIONS

Silverstein et al., "Gastrointestinal toxicity with celecoxib vs nonsteroidal anti-inflammatory drugs for osteoarthritis and rheumatoid arthritis; the CLASS study: a randomized controlled trial," *JAMA*, 284:1247-1255, 2000.

Silverstein et al., "Misoprostol reduces serious gastrointestinal complications in paetints with rheumatoid arthritis receiving nonsteroidal anti-inflammatory drugs," *Ann. Intern. Med.*, 123(4):241-249, 1995.

Simon et al.,"Schutzwirkung von omeprazol genguber niedrig dosierter acetylsalicylsaure," *Arzneimittel Forschung*, 45:701-703, 1995. (English Translation enclosed).

Sung, "Management of nonsteroidal anti-imflammatory drug-related peptic ulcer bleeding," *Am. J. Med.*, 110(1A): 29S-32S, 2001.

Taha et al., "Famotidine for the prevention of peptic ulcers and oesophagitis in patients taking low-dose aspirin (FAMOUS): a phase III, randomized, double-blind, placebo-controlled trial," *Lancet*, 374:119-25, 2009.

Takeuchi et al., "Effects of topical application of acidified omeprazole on acid secretion and transmucosal potential difference in anesthetized rat stomachs," *Japan J. Pharmacol.*, 47:397-1988.

Tronstad et al., "Gastroscopic finding after treatment with enteric-coated and plain naproxen tablets in healthy subjects," *Scand. J. Gastroenterol.*, 20:239-242, 1985.

Vane et al., "The future of NSAID therapy: selective COX-2 inhibitors," *IJCP*, 54(1):7-9, Jan./Feb. 2000.

Vaz-da-Silva et al., "Relative bioavailability of two enteric-coated formulations of omeprazole following repeated doses in healthy volunteers," *Clinical Drug Investigation*, 21(3):201-210, 2001. (Abstract).

von Unge et al., "Stereochemical assignment of the enantiomers of omeprazole from X-ray anaylysis of a fenchyloxymethyl derivative of (+)-(R)- omeprazole," *Tetrahedron*, 8(12):1967-1970, 1997.

Wagner et al., "Effects of nonsteroidal anti-inflammatory drugs on ulcerogensis and gastric secretion in pylorus-ligated rat," *Digestive Diseases and Sciences*, 40:134-140, 1995.

Wakatini et al., "Profile of JTE-522 as a human cyclooxygenase -2 inhibitor," *Jpn J Pharmacol.*, 78:365-371, 1998.

Wallmark et al., "The relationship between gastric acid secretion and gastric $H^+$, $K^+$-ATPase activity," *J. Biol. Chem..*, 260(25): 13681-13684, 1985

Warner et al., "Nonsteroidal drug selectives for cyclo-oxygenase-1 rather than cyclo-oxygenase-2 are associated with human gastrointestinal toxicity: a full in vitro analysis," *Proc. Natl. Acad. Sci. USA*, 96:7563-7568, 1999.

Weil et al, "Prophylactic aspirin and risk of peptic ulcer bleeding," *BMJ*, 310: 827-830, 1995.

Weksler et al., "Effects of low dose aspirin on platelet function in patients with recent cerebral ischemia," *Storke*, 16(1):5-9, 1985.

Wilson et al., "Effects of misoprostol on gastric acid and mucus secretion in man," *Digestive Diseases and Sciences*, 31(2): 126S-129S, 1986.

Wolfe et al., "Acid suppression: optimizing therapy for gastroduodenal ulcer healing, gastroesophageal reflux disease, and stress related erosive syndrome," *Gastroenterology*, 18(2):S9-S31, 2000.

Wolfe et al., "Gastrointestinal toxicity of nonsteroidal anti-inflammatory drugs," *N. Engl. J. Med.*, 340:1888-1899, 1999.

Yeomans et al., "A clinical approach to management of patients with non-steroidal anti-inflammatory gastropathy," *Ital. J. Gastroenterol. Hepatol.*, 31(Suppl. 1):S89-92, 1999.

Yeomans et al., "A comparison of omeprazole with ranitidine for ulcers associated with non steroidal anti-inflammatory drugs," *N. Engl. J. Med.*, 338:719-726, 1998.

Yeomans et al., "Efficacy of esomeprazole (20 mg once daily) for reducing the risk of gastroduodenal ulcers associated with continuous use of low-dose aspirin," *American Journal of Gastroenterology*, 103:1-9, 2008.

Yeomans et al., "New data on healing of nonsteroidal anti-inflammatory drug-associated ulcers and erosions," *Am. J. Med.*, 104:56S-61S, 1998.

COMPOSITIONS AND METHODS FOR DELIVERY OF OMEPRAZOLE PLUS ACETYLSALICYLIC ACID

This application is a continuation of U.S. patent application Ser. No. 15/338,825, filed Oct. 31, 2016, which is a continuation of U.S. patent application Ser. No. 14/367,972, filed Jun. 23, 2014, now U.S. Pat. No. 9,539,214, which is a national phase application under 35 U.S.C. § 371 of International Application No. PCT/US2012/071759, filed Dec. 27, 2012, which claims benefit of priority to U.S. Provisional Application Ser. No. 61/580,861, filed Dec. 28, 2011, and U.S. Provisional Application Ser. No. 61/585,432, filed Jan. 11, 2012. The entire contents of each of the above referenced disclosures are specifically incorporated herein by reference.

BACKGROUND OF THE INVENTION

1. Field of the Invention

The present invention relates generally to the fields of medicine, pharmacology and pharmaceuticals. In particular, compositions and methods are provided for the delivery of pharmaceuticals to a patient in need thereof. The pharmaceutical composition is in unit dose form comprising acetylsalicylic acid, or pharmaceutically acceptable salt thereof, and omeprazole, or pharmaceutically acceptable salt thereof.

2. Background of the Invention

Over 15 million Americans take nonsteroidal anti-inflammatory drugs (NSAIDs) each day as a treatment for pain or inflammation. Unfortunately, many of these NSAIDs are associated with a high incidence of gastrointestinal complications, including gastritis, dyspepsia, gastroduodenal ulcers, perforations, and bleeding. A major factor contributing to the development of gastrointestinal lesions appears to be the presence of acid in the stomach and upper small intestines.

During recent years, attempts have been made to reduce the gastrointestinal risk associated with taking NSAIDs by administering agents that inhibit stomach acid secretion, such as, for example, proton pump inhibitors with the NSAID. For example, U.S. Pat. No. 6,926,907 is directed to at least one drug dosage form comprising a proton pump inhibitor that raises the pH of a patient's gastrointestinal tract, followed by an NSAID. This, and similar, formulations can be effective in improving NSAID tolerability through dosages of omeprazole and acetylsalicylic acid that produce the desired pharmacodynamic response and pharmacokinetic values. Parameters that may influence the desired pharmacodynamic response and pharmacokinetic values include, but are not limited to, for example, the dosage of each; extent of drug absorption; extent of drug distribution, and the duration of drug administration.

There is a need for a clinically effective therapy that delivers to a patient in need thereof a pharmaceutical composition in a unit dose form comprising acetylsalicylic acid, or pharmaceutically acceptable salt thereof, and omeprazole, or pharmaceutically acceptable salt thereof, for a duration sufficient to achieve an intragastric pH of about 4 or greater and a plasma level of acetylsalicylic acid that is efficacious.

SUMMARY OF THE INVENTION

The present invention is redirected to a method for delivering a pharmaceutical composition to a patient in need thereof, comprising administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater, wherein one unit dose form is administered to target:
  i) a pharmacokinetic (pk) profile for acetylsalicylic acid where:
   a) the dose has a acetylsalicylic acid mean $C_{max}$ of about 2.0 to about 3.0 µg/mL and a median time to maximum concentration ($T_{max}$) of from about 3.0 to about 3.5 hours, and/or
   b) the dose has a salicylic acid mean $C_{max}$ of about 15 to about 16.5 µg/mL and a median time to maximum concentration ($T_{max}$) of from about 3.0 to about 3.5 hours,
  ii) a pharmacokinetic (pk) profile for omeprazole where the dose has a mean area under the plasma concentration-time curve from time zero when the dose is administered to about 12 hours after the dose is administered ($AUC_{0-12}$) of about 0.8 to about 2.5 hr*µg/mL.

The patient in need thereof is being treated for a disease or disorder selected from pain and inflammation, such as cardiovascular disease, osteoarthritis, rheumatoid arthritis, ankylosing spondylitis, or a combination thereof.

The pharmaceutical composition may further target a mean % time at which intragastric pH remains at about 4.0 or greater for about a 24 hour period after reaching steady state of at least about 50%, for example, greater than 60%, such as greater than 70%. The pk profile for acetylsalicylic acid may have a mean acetylsalicylic acid $C_{max}$ of at least 2.36 µg/ml and a mean salicylic acid $C_{max}$ of at least 15.3 µg/ml. The pk profile for acetylsalicylic acid may have a mean acetylsalicylic acid $C_{max}$ of 2.5 to 3 µg/ml, for example, about 2.91 µg/ml and a mean salicylic acid $C_{max}$ of at least 16.2 µg/ml. The % coefficient of variation for acetylsalicylic acid may be 50% to 60%, for example, about 54%, and the coefficient of variation for salicylic acid may be 25% to, for example, greater than 35%, for example, about 29%. The omeprazole mean area under the plasma concentration-time curve from time zero when the dose is administered to about 12 hours after the dose is administered ($AUC_{0-12}$) is 1.9 hr*µg/mL to 2.3 hr*µg/mL, for example, about 2.174 hr*µg/mL. The % coefficient of variation for the omeprazole mean area under the plasma concentration-time curve from time zero when the dose is administered to about 12 hours after the dose is administered ($AUC_{0-12}$) is 80% to 90%, for example, about 88%. The omeprazole mean area under the plasma concentration-time curve from time zero when the dose is administered to about 24 hours after the dose is administered ($AUC_{0-24}$) is 1.9 hr*µg/mL to 2.3 hr*µg/mL, for example, about 2.187 hr*µg/mL. The % coefficient of variation for the omeprazole mean area under the plasma concentration-time curve from time zero when the dose is administered to about 24 hours after the dose is administered ($AUC_{0-24}$) is 80% to 90%, for example, about 88%.

The pharmaceutical composition which is capable of targeting the above-mentioned pharmacokinetic (pk) profile in unit dose form may comprise about 325 mg of said acetylsalicylic acid and about 40 mg of said omeprazole. The unit dose form may be administered for a period of at least about 3, 5 or 7 days. The unit dose form may be administered for a period of at least about 14 days. The unit dose form may be a multilayer tablet comprising at least one core and at least a first layer and a second layer, wherein:
  i) said core comprises acetylsalicylic acid, or pharmaceutically acceptable salt thereof;
  ii) said first layer is a coating that at least begins to dissolve when the pH of the surrounding medium is about 3.5 or greater; and
  iii) said second layer comprises omeprazole, wherein said omeprazole is released at a pH of from about 0 or greater,
optionally where the omeprazole is released at a pH of from about 0 to about 2.

In one aspect, the disclosure is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater to target a mean % time at which intragastric pH remains at about 4.0 or greater for about a 24-hour period after reaching steady state of at least about 50, for example, greater than 60%, such as greater than 70%.

In another aspect, the disclosure is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater, to target:
  i) a pk profile for acetylsalicylic acid where the dose has a mean $C_{max}$ of about 2.91 µg/mL and a median time to maximum concentration ($T_{max}$) of from about 3.0 to about 3.5 hours, and
  ii) a pk profile for omeprazole where the dose has a mean area under the plasma concentration-time curve from time zero when the dose is administered to about 12 hours after the dose is administered ($AUC_{0-12}$) is about 2.174 hr*µg/mL.

Yet another aspect is directed to delivering a pharmaceutical composition in unit dose form that provides the pharmacodynamic response and/or pharmacokinetic values disclosed herein to a patient being treated for a disease or disorder selected from pain and inflammation.

A further aspect is directed to delivering a pharmaceutical composition in unit dose form that provides the pharmacodynamic response and/or pharmacokinetic values disclosed herein to a patient being treated for osteoarthritis, rheumatoid arthritis, ankylosing spondylitis, or a combination thereof.

A still further aspect is directed to delivering a pharmaceutical composition in unit dose form that provides the pharmacodynamic response and/or pharmacokinetic values disclosed herein to an at risk patient.

Another aspect is directed to delivering a pharmaceutical composition in unit dose form that provides the pharmacodynamic response and/or pharmacokinetic values disclosed herein to an at risk patient being treated for a disease or disorder selected from pain and inflammation.

A further aspect is directed to delivering a pharmaceutical composition in unit dose form that provides the pharmacodynamic response and/or pharmacokinetic values disclosed herein to an at risk patient being treated for osteoarthritis, rheumatoid arthritis, ankylosing spondylitis, or a combination thereof.

Yet another aspect is directed to delivering a pharmaceutical composition in unit dosage form that provides the pharmacodynamic response and/or pharmacokinetic values disclosed herein via a multilayer tablet comprising at least one core and at least a first layer and a second layer, wherein:
  i) said core comprises acetylsalicylic acid, or pharmaceutically acceptable salt thereof;
  ii) said first layer is a coating that at least begins to release the acetylsalicylic acid, or pharmaceutically acceptable salt thereof, when the pH of the surrounding medium is at about 3.5 or greater; and
  iii) said second layer is omeprazole, or pharmaceutically acceptable salt thereof, wherein said omeprazole, or pharmaceutically acceptable salt thereof, is released at a pH of from about 0 or greater.

Another embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater to target: a mean % time at which intragastric pH remains at about 4.0 or greater for about a 24 hour period after reaching steady state of at least about 50% and a pharmacokinetic (pk) profile having a mean maximum plasma concentration ($C_{max}$) for acetylsalicylic acid of at least 2.91 µg/mL, optionally with a % coefficient of variation of 54%.

Yet another embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from 0 or greater to target: a mean % time at which intragastric pH remains at about 4.0 or greater for about a 24 hour period after reaching steady state of at least about 50% and a pharmacokinetic (pk) profile having a mean area under the plasma concentration-time curve from time zero when first dose is administered to about 24 hours after the first dose is administered ($AUC_{0-24}$) for omeprazole of at least 0.880 hr*µg/mL, optionally with a % coefficient of variation of 109%.

Still yet another embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater to target: a mean % time at which intragastric pH remains at about 4.0 or greater for about a 24 hour period after reaching steady state of at least about 50%; and a pharmacokinetic (pk) profile having a mean maximum plasma concentration ($C_{max}$) for acetylsalicylic acid of at least 2.91 µg/mL, optionally with a % coefficient of variation of 54% and a mean area under the plasma concentration-time curve from time zero when first dose is administered to about 24 hours after the first dose is administered ($AUC_{0-24}$)

for omeprazole of at least 0.880 hr*μg/mL, optionally with a % coefficient of variation of 55%.

Still even yet another embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater to target: a mean % time at which intragastric pH remains at about 4.0 or greater for about a 24 hour period after reaching steady state of at least about 50%; and a pharmacokinetic (pk) profile having a mean maximum plasma concentration ($C_{max}$) for acetylsalicylic acid of about 2.91 μg/mL and a mean area under the plasma concentration-time curve from time zero when first dose is administered to about 24 hours after the first dose is administered ($AUC_{0-24}$) for omeprazole of about 0.880 hr*μg/mL.

A still even further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater to target: a pharmacokinetic (pk) profile having a mean maximum plasma concentration ($C_{max}$) for acetylsalicylic acid of at least 2.91 μg/mL, optionally with a % coefficient of variation of 54%.

A yet still further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater to target: and a pharmacokinetic (pk) profile having mean area under the plasma concentration-time curve from time zero when first dose is administered to about 24 hours after the first dose is administered ($AUC_{0-24}$) for omeprazole of at least 0.880 hr*μg/mL with a % coefficient of variation of 109%.

A yet even further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater to target: and a pharmacokinetic (pk) profile having mean area under the plasma concentration-time curve from time zero when first dose is administered to about 24 hours after the first dose is administered ($AUC_{0-24}$) for omeprazole of about 0.880 hr*μg/mL.

A further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater to target:
  i) a pk profile for acetylsalicylic acid where the dose has a mean $C_{max}$ of at least 2.91 μg/mL with a % coefficient of variation 54% and a median time to maximum concentration ($T_{max}$) of from about 3.0 to about 3.5 hours, and
  ii) a pk profile for omeprazole where the dose has a mean area under the plasma concentration-time curve from time zero when the dose is administered to about 12 hours after the dose is administered ($AUC_{0-12}$) of at least 2.174 hr*μg/mL, optionally with a % coefficient of variation of 88%.

A still further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater to target:
  a pk profile for acetylsalicylic acid where the dose has a mean $C_{max}$ of at least 2.91 μg/mL, optionally with a % coefficient of variation of 54% and a median time to maximum concentration ($T_{max}$) of from about 3.0 to about 3.5 hours.

A yet even still further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater to target:
  a pk profile for omeprazole where the dose has a mean area under the plasma concentration-time curve from time zero when the dose is administered to about 12 hours after the dose is administered ($AUC_{0-12}$) is at least 2.174 hr*μg/mL, optionally with a % coefficient of variation of 88%.

A further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater, to target a pk profile for omeprazole where the dose has a mean area under the plasma concentration-time curve from time zero when the dose is administered to about 12 hours after the dose is administered ($AUC_{0-12}$) of at least 2.174 hr*μg/mL; optionally with a % coefficient of variation of 88%.

A yet still even further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater, to target:
  i) a pk profile for acetylsalicylic acid where the dose has a mean $C_{max}$ of at least 2.91 μg/mL with a % coefficient of variation of 54% and a median time to maximum concentration ($T_{max}$) of from about 3.0 to about 3.5 hours, and ii) a pk profile for omeprazole where the dose has a mean area under the plasma concentration-time curve from time zero when the dose is administered to about 12 hours after the dose is administered ($AUC_{0-12}$) is at least 2.174 hr*μg/mL, optionally with a % coefficient of variation of 88%, and iii) a mean % time at which intragastric pH remains at about 4.0 or greater for about a 24 hour period after reaching steady state of at least about 50%.

A still even further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater, to target:

i) a pk profile for acetylsalicylic acid where the dose has a mean $C_{max}$ of about least 2.91 μg/mL and a median time to maximum concentration ($T_{max}$) of from about 3.0 to about 3.5 hours, and ii) a pk profile for omeprazole where the dose has a mean area under the plasma concentration-time curve from time zero when the dose is administered to about 12 hours after the dose is administered ($AUC_{0-12}$) of about 2.174 hr*μg/mL, and iii) a mean % time at which intragastric pH remains at about 4.0 or greater for about a 24 hour period after reaching steady state of at least about 50%.

Still yet another embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater, to target:

i) a pk profile for acetylsalicylic acid where the dose has a mean $C_{max}$ of at least 2.91 μg/mL, optionally with a % coefficient of variation of 54% and a median time to maximum concentration ($T_{max}$) of from about 3.0 to about 3.5 hours, and ii) a mean % time at which intragastric pH remains at about 4.0 or greater for about a 24 hour period after reaching steady state of at least about 50%.

Even still yet a further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole is released from said unit dose form at a pH of from 0 or greater, to target:

i) a pk profile for omeprazole where the dose has a mean area under the plasma concentration-time curve from time zero when the dose is administered to about 12 hours after the dose is administered ($AUC_{0-12}$) is at least 2.174 hr*μg/mL, optionally with a % coefficient of variation of 88%, and ii) a mean % time at which intragastric pH remains at about 4.0 or greater for about a 24 hour after reaching steady state period of at least about 50%.

A yet still even further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater, to target:

i) a pk profile for acetylsalicylic acid where the dose has a mean $C_{max}$ of at least 2.91 μg/mL with a % coefficient of variation of 54% and a median time to maximum concentration ($T_{max}$) of from about 3.0 to about 3.5 hours, and ii) a pk profile for omeprazole where the dose has a mean area under the plasma concentration-time curve from time zero when the dose is administered to 12 hours after the dose is administered ($AUC_{0-12}$) is at least 2.174 hr*μg/mL, optionally with a % coefficient of variation of 88%, and iii) a mean % time at which intragastric pH remains at about 4.0 or greater for about a 24 hour period after reaching steady state of at least about 50%; and iv) a pharmacokinetic (pk) profile having a mean area under the plasma concentration-time curve from time zero when first dose is administered to about 24 hours after the first dose is administered ($AUC_{0-24}$) for omeprazole of at least 0.880 hr*μg/mL, optionally with a % coefficient of variation of 109%.

A further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater, to target:

i) a pk profile for acetylsalicylic acid where the dose has a mean $C_{max}$ of at least 2.91 μg/mL with a % coefficient of variation of 54% and a median time to maximum concentration ($T_{max}$) of from about 3.0 to about 3.5 hours, and ii) a pk profile for omeprazole where the dose has a mean area under the plasma concentration-time curve from time zero when the dose is administered to about 12 hours after the dose is administered ($AUC_{0-12}$) of at least 2.174 hr*μg/mL, optionally with a % coefficient of variation of 88%, and iii) a pharmacokinetic (pk) profile having a mean area under the plasma concentration-time curve from time zero when first dose is administered to about 24 hours after the first dose is administered ($AUC_{0-24}$) for omeprazole of at least 0.880 hr*μg/mL, optionally with a % coefficient of variation of 109%.

A still further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater, to target:

i) a pk profile for omeprazole where the dose has a mean area under the plasma concentration-time curve from time zero when the dose is administered to about 12 hours after the dose is administered ($AUC_{0-12}$) of at least 2.174 hr*µg/mL with a % coefficient of variation of 29%, and ii) a pharmacokinetic (pk) profile having a mean area under the plasma concentration-time curve from time zero when first dose is administered to about 24 hours after the first dose is administered ($AUC_{0-24}$) for omeprazole of at least 0.880 hr*µg/mL with a % coefficient of variation of 88%.

Still a further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater, to target:

i) a pk profile for omeprazole where the dose has a mean area under the plasma concentration-time curve from time zero when the dose is administered to about 12 hours after the dose is administered ($AUC_{0-10}$) of about 2.174 hr*µg/mL, and ii) a pharmacokinetic (pk) profile having a mean area under the plasma concentration-time curve from time zero when first dose is administered to about 24 hours after the first dose is administered ($AUC_{0-24}$) for omeprazole of about 0.880 hr*µg/mL.

Yet another embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater, to target:

i) a pk profile for acetylsalicylic acid where the dose has a mean $C_{max}$ of at least 2.91 µm/mL, optionally with a % coefficient of variation of 54% and a median time to maximum concentration ($T_{max}$) of from about 3.0 to about 3.5 hours, and ii) a pharmacokinetic (pk) profile having a mean area under the plasma concentration-time curve from time zero when first dose is administered to about 24 hours after the first dose is administered ($AUC_{0-24}$) for omeprazole is at least 0.880 hr*µg/mL, optionally with a % coefficient of variation of 109%.

Yet a further embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater, to target:

i) a pk profile for omeprazole where the dose has a mean area under the plasma concentration-time curve from time zero when the dose is administered to about 12 hours after the dose is administered ($AUC_{0-12}$) of at least 2.174 hr*µg/mL, optionally with a % coefficient of variation of 88%, and ii) a mean % time at which intragastric pH remains at about 4.0 or greater for about a 24 hour period after reaching steady state of at least about 50%; and iii) a pharmacokinetic (pk) profile having a mean area under the plasma concentration-time curve from time zero when first dose is administered to about 24 hours after the first dose is administered ($AUC_{0-24}$) for omeprazole is at least 0.880 hr*µg/mL, optionally with a % coefficient of variation of 109%.

Yet another embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater, to target:

i) a pk profile for acetylsalicylic acid where the dose has a mean $C_{max}$ of at least 2.91 µm/mL, optionally with a % coefficient of variation ranging of 54% and a median time to maximum concentration ($T_{max}$) of from about 3.0 to about 3.5 hours, and ii) a mean % time at which intragastric pH remains at about 3.0 or greater for about a 24 hour period after reaching steady state of at least about 50%; and iii) a pharmacokinetic (pk) profile having a mean area under the plasma concentration-time curve from time zero when first dose is administered to about 24 hours after the first dose is administered ($AUC_{0-24}$) for omeprazole is at least 0.880 hr*µg/mL, optionally with a % coefficient of variation of 109%.

In another embodiment, acetylsalicylic acid can be present as the free base in an amount of from about 75 mg, or in an amount of about 100 mg.

In yet another embodiment, acetylsalicylic acid can be present in equivalent amounts of pharmaceutically acceptable salts of acetylsalicylic acid, e.g., lysine acetylsalicylic acid.

In a further embodiment, omeprazole can be present as a sodium salt.

In an even further embodiment, omeprazole, or pharmaceutically acceptable salt thereof, can be present in an amount to provide from about 10 mg to about 50 mg of omeprazole.

In a further embodiment, omeprazole, or pharmaceutically acceptable salt thereof, can be present in an amount to provide about 15 mg of omeprazole.

In yet an even further embodiment, omeprazole, or pharmaceutically acceptable salt thereof, can be present in an amount to provide about 20 mg of omeprazole.

In still yet another embodiment, omeprazole, or pharmaceutically acceptable salt thereof, can be present in an amount to provide about 40 mg of omeprazole.

In still another embodiment, the mean % time at which intragastric pH remains at about 4.0 or greater for about a 24 hour period after reaching steady state is at least about 35% or at least about 40%.

In still yet an even further embodiment, the mean % time at which intragastric pH remains at about 4.0 or greater for about a 24 hour period after reaching steady state is at least about 45%.

In an even still further embodiment, the mean maximum plasma concentration ($C_{max}$) for acetylsalicylic acid is at least 15.5 µg/mL with a % coefficient of variation ranging of 28. In a further embodiment, the mean maximum plasma concentration ($C_{max}$) for acetylsalicylic acid is about 4 μg/mL.

In yet an even still further embodiment, the mean area under the plasma concentration-time curve from time zero when first dose is administered to about 24 hours after the first dose is administered ($AUC_{0-24}$) for omeprazole is 0.880 hr*μg/mL with a coefficient of variation of 109.

In another embodiment, the mean area under the plasma concentration-time curve from time zero when first dose is administered to about 24 hours after the first dose is administered ($AUC_{0-24}$) for omeprazole is about 0.4 hr*μg/mL.

In yet another embodiment, the mean area under the plasma concentration-time curve from time zero when first dose is administered to about 24 hours after the first dose is administered ($AUC_{0-24}$) for omeprazole is about 0.880 hr*μg/mL with a % coefficient of variation of 109.

In yet another embodiment, the mean area under the plasma concentration-time curve from time zero when first dose is administered to about 24 hours after the first dose is administered ($AUC_{0-24}$) for omeprazole is about 0.4 hr*μg/mL.

In still another embodiment, the mean area under the plasma concentration-time curve from time zero when first dose is administered to about 24 hours after the first dose is administered ($AUC_{0-24}$) for omeprazole is about 0.5 hr*μg/mL.

In a still further embodiment, the mean area under the plasma concentration-time curve from time zero when first dose is administered to about 24 hours after the first dose is administered ($AUC_{0-24}$) for omeprazole is 0.880 hr*μg/mL with a % coefficient of variation of 109.

In yet still a further embodiment, the mean area under the plasma concentration-time curve from time zero when the first dose is administered to about 24 hours after the first dose is administered ($AUC_{0-24}$) for omeprazole is about 0.880 hr*μg/mL.

In one embodiment, the pharmaceutical composition in unit dose form comprises about 325 mg of said acetylsalicylic acid, or pharmaceutically acceptable salt thereof, and about 40 mg of said omeprazole, or pharmaceutically acceptable salt thereof In another embodiment, the pharmaceutical composition in unit dose form comprises about 81 mg of said acetylsalicylic acid, or pharmaceutically acceptable salt thereof, and about 20 mg of said omeprazole, or pharmaceutically acceptable salt thereof.

In yet another embodiment, the unit dose form is administered once a day for at least 7 days. In still another embodiment, the unit dose form is administered once a day for at least 15 days.

In yet another embodiment, the mean $C_{max}$ for said dose of acetylsalicylic acid is 2.91 μg/mL with a % coefficient of variation of 109% and said median $T_{max}$ is about 3.5 hours.

In another embodiment, the mean $C_{max}$ for said dose of acetylsalicylic acid is about 2.36 μg/mL and said median $T_{max}$ is about 3.0 hours.

In still another embodiment, the mean $C_{max}$ for said dose of acetylsalicylic acid is 2.36 μg/mL with a % coefficient of variation of 56% and said median $T_{max}$ is about 3 hours.

In still yet another embodiment, the mean $C_{max}$ for said dose of acetylsalicylic acid is about 2.91 μg/mL with a % coefficient of variation of 54% and said median $T_{max}$ is about 3.5 hours.

In yet still another embodiment, the mean area under the plasma concentration-time curve from time zero when the dose is administered to about 12 hours after the dose is administered ($AUC_{0-12}$) for said dose of omeprazole is 2.174 hr*μg/mL, optionally with a % coefficient of variation of 88%.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Throughout the specification, unless it is made explicit that different embodiments of the invention are considered exclusive to other embodiments, all embodiments and features thereof may be combined.

The term "comprising" encompasses "including" as well as "consisting," e.g., a composition "comprising" X may consist exclusively of X or may include something additional, e.g., X+Y.

The word "substantially" does not exclude "completely" e.g. a composition which is "substantially free" from Y may be completely free from Y. Where necessary, the word "substantially" may be omitted from the definition of the invention.

As used herein, "treatment" includes prophylactic treatment. As used herein, a "patient" means an animal, e.g. a mammal, typically a human, in need of treatment.

In any of the above embodiments, the unit dose of the present invention may be given once or twice daily.

In any of the above embodiments, the unit dose of the present invention may be given for 1, 2, 3, 4, 5, 6, 7, 8, 9, 10 or more days of treatment, for example, may be given chronically for periods of greater than a month, for example, for periods of a year or more.

The pharmaceutical composition in unit dose form of the present invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids (e.g. aqueous solutions), emulsions or powders; lozenges (including liquid-filled); chews; gels; fast dispersing dosage forms; films; ovules; sprays; and buccal/mucoadhesive patches.

Formulations suitable for oral administration may also be designed to deliver the various components of the formulation in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the components of the present invention to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

It is contemplated that any method or composition described herein can be implemented with respect to any other method or composition described herein. Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
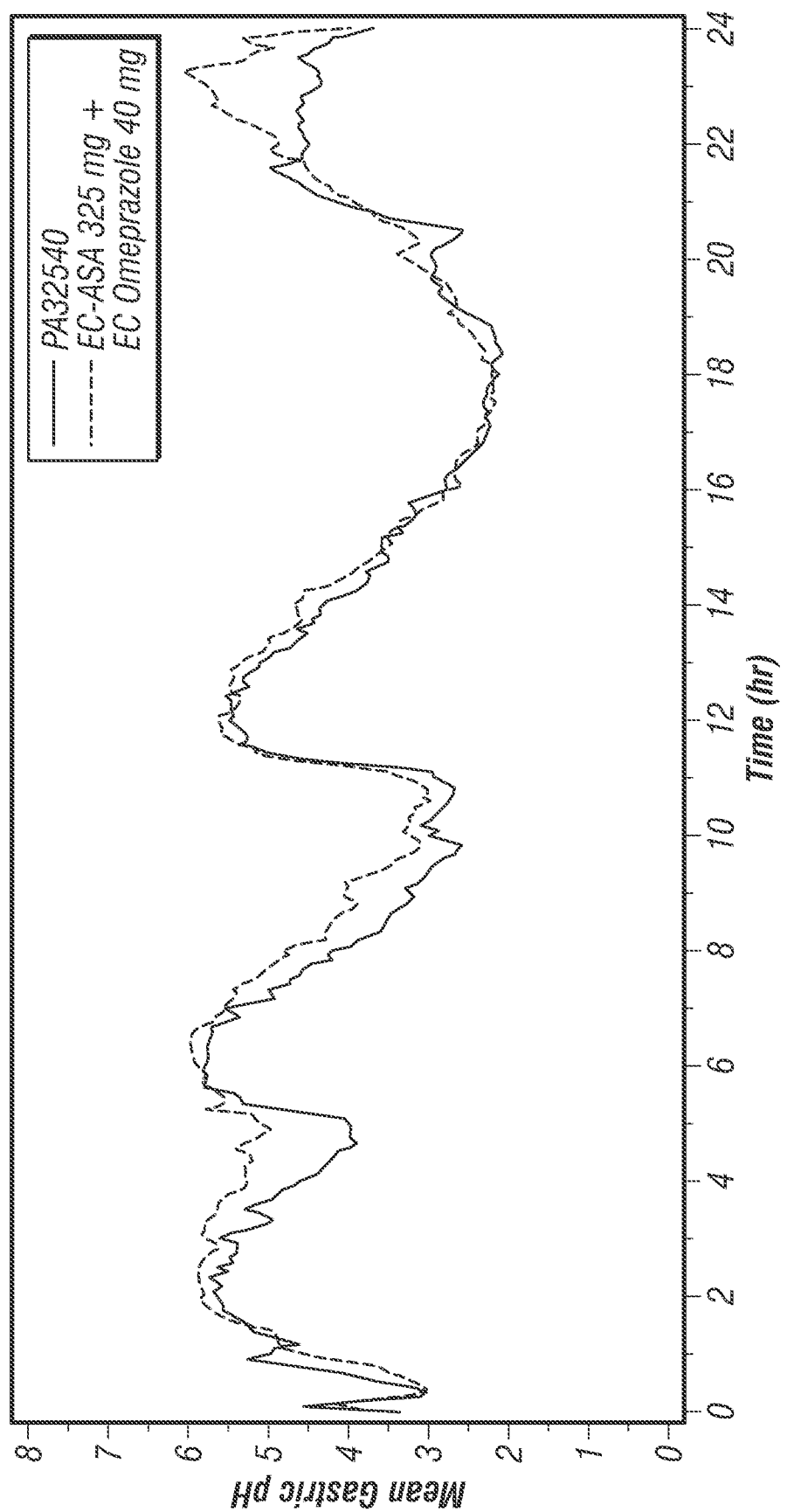
FIG. 1—Mean pH Data over 24 Hours on Day 7 (Per-Protocol Population).

The present disclosure is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof.

I. Definitions

The following table provides a list of commonly utilized abbreviations found throughout the application.

TABLE 1

Abbreviations and Special Terms

| Abbreviation | Explanation |
|---|---|
| ANOVA | analysis of variance |
| AUC | area under the plasma concentration-time curve |
| $AUC_{0-12}$ | AUC from time zero to 12 hours after the dose |
| $AUC_{0-24}$ | AUC from time zero to 24 hours after the dose |
| $AUC_{0-t}$ | AUC from time zero to the last time point with measurable drug concentration |
| Bid | twice daily |
| BQL | below the lower limit of quantification |
| CBC | complete blood count |
| CI | confidence interval |
| $C_{max}$ | maximum plasma concentration |
| CV | coefficient of variation |
| GCP | Good Clinical Practice |
| EC | enteric-coated |
| ECG | electrocardiogram |
| eCRF | electronic case report form |
| $E_{max}$ | maximal response or pharmacodynamic effect |
| GI | Gastrointestinal |
| GLSM | Geometric least-squares mean |

TABLE 1-continued

Abbreviations and Special Terms

| Abbreviation | Explanation |
|---|---|
| HPLC/MS/MS | high pressure liquid chromatography tandem mass spectrometry |
| ITT | intent-to-treat |
| LLOQ | lower limit of quantification |
| LS | least square |
| MedDRA | Medical Dictionary for Regulatoy Activities |
| MRM | multiple reaction monitoring |
| $\lambda_z$ | apparent first-order elimination rate constant |
| Ln | natural log |
| PD | pharmacodynamic(s) |
| PDS | Phoenix Data Systems |
| PK | pharmacokinetic(s) |
| PP | per protocol |
| PPD | Pharmaceutical Product Development |
| PPI | proton pump inhibitor |
| QC | quality control |
| SD | standard deviation |
| SE | standard error |
| SOC | system organ class |
| SPE | solid phase extraction |
| $t_{lag}$ | time to the first measurable plasma concentration following the AM dose ($t_{lag,am}$) |
| $t_{last}$ | last time point with measurable drug concentration |
| $T_{max}$ | time to maximum plasma concentration |
| $t_{1/2}$ | apparent plasma half-life |

The term "at risk patient" refers to patient(s) at risk for NSAID associated ulcer due to age or a documented history of gastric ulcers, or receiving concomitant LDA (low dose acetylsalicylic acid). In one embodiment, the at risk patient is a patient at risk for NSAID associated ulcer due to age greater than or equal to 50 years. In another embodiment, the at risk patient is a patient at risk for NSAID associated ulcer due to concomitant acetylsalicylic acid use. In yet another embodiment, the at risk patient is a patient at risk for NSAID associated ulcer due to history of upper gastrointestinal (UGI) ulcer or bleeding The term "pharmaceutically-acceptable", as employed herein, indicates the subject matter being identified as "pharmaceutically acceptable" is suitable and physiologically acceptable for administration to a patient/subject. For example, the term "pharmaceutically acceptable salt(s)" denotes suitable and physiologically acceptable salt(s).

The phrase "acetylsalicylic acid, or pharmaceutically acceptable salt thereof" refers to the free base of acetylsalicylic acid, pharmaceutically acceptable salt(s) of acetylsalicylic acid, and/or mixtures of the free base of acetylsalicylic acid and at least one pharmaceutically acceptable salt of acetylsalicylic acid.

The phrase "omeprazole, or pharmaceutically acceptable salt thereof" refers to the free base of omeprazole, pharmaceutically acceptable salt(s) of omeprazole, and/or mixtures of the free base of omeprazole and at least one pharmaceutically acceptable salt of omeprazole.

The term "unit dosage form" (or "unit dose form") as used herein refers to a single entity for drug administration. For example, a single tablet or capsule containing both omeprazole and acetylsalicylic acid is a unit dosage form. Unit dosage forms of the present disclosure provide for sequential drug release in a way that elevates gastric pH and reduces the deleterious effects of acetylsalicylic acid on the gastroduodenal mucosa, i.e., the omeprazole is released first and the release of acetylsalicylic acid is delayed until after the pH in the GI tract has risen to 3.5 or greater. A "unit dosage form" (or "unit dose form") may also be referred to as a "fixed dosage form" (or "fixed dose form") or fixed dosage combination (or fixed dose combination") and are otherwise interchangeable.

With regard to the pharmacokinetic and/or pharmacodynamic values provided herein, the degree of variation is reflected in SDs and % CV values. The % CV=SD/mean× 100; the SD=(% CV×mean) divided by 100. It can be expected that approximately 68% of patients will be within one SD of the mean and approximately 95% of patients will be within two SDs of the mean. The pharmacokinetic and pharmacodynamic values presented herein are average values, rounded to the nearest whole number, and are based upon results obtained from multiple individuals. As a result, the values presented herein may vary from one patient to another. This variation is reflected in the term "about."

With regard to the dosages of each of acetylsalicylic acid, or pharmaceutically acceptable salt thereof and/or omeprazole, or pharmaceutically acceptable salt thereof the term "about" is intended to reflect variations from the specifically identified dosages that are acceptable within the art.

With regard to the numerical % coefficient of variation values and/or ranges used herein, the term "about" is intended to reflect variations above and below the stated numerical value and/or range that that may achieve substantially the same results as the stated number.

With regard to the pH values and/or ranges recited herein, the term "about" is intended to capture variations above and below the stated number that may achieve substantially the same results as the stated number.

With regard to the term numerical values used in conjunction with the phrase "substantially free," the term is intended to capture variations above and below the stated number that may achieve substantially the same results as the stated number.

The phrase "substantially free" means from about 95% to about 99.99% free. In one embodiment, substantially free means about 95% free. In another embodiment, the term substantially free means about 96% free. In still another embodiment, the term substantially free means about 97% free. In yet another embodiment, the term substantially free means about 98% free. In a further embodiment, the term substantially free means about 99% free. In still a further embodiment, the term substantially free means about 99.99% free.

In the present disclosure, each of the variously stated ranges is intended to be continuous so as to include each numerical parameter between the stated minimum and maximum value of each range. For Example, a range of about 1 to about 4 includes about 1, 1, about 2, 2, about 3, 3, about 4, and 4.

II. Acetylsalicylic Acid, Omeprazole and PA32540

A. Acetylsalicylic Acid

Nonsteroidal anti-inflammatory drugs (NSAIDs) are drugs with analgesic and antipyretic (fever-reducing) effects and which have, in higher doses, anti-inflammatory effects. The term "nonsteroidal" is used to distinguish these drugs from steroids, which, among a broad range of other effects, have a similar eicosanoid-depressing, anti-inflammatory action. As analgesics, NSAIDs are unusual in that they are non-narcotic.

Most NSAIDs act as nonselective inhibitors of the enzyme cyclooxygenase (COX), inhibiting both the cyclooxygenase-1 (COX-1) and cyclooxygenase-2 (COX-2) isoenzymes. COX catalyzes the formation of prostaglandins and thromboxane from arachidonic acid (itself derived from the cellular phospholipid bilayer by phospholipase A2). Prostaglandins act (among other things) as messenger molecules in the process of inflammation. Many aspects of the mechanism of action of NSAIDs remain unexplained, and for this reason further COX pathways are hypothesized. The COX-3 pathway was believed to fill some of this gap but recent findings make it appear unlikely that it plays any significant role in humans and alternative explanation models are proposed.

The widespread use of NSAIDs has meant that the adverse effects of these drugs have become increasingly prevalent. The two main adverse drug reactions (ADRs) associated with NSAIDs relate to gastrointestinal (GI) effects and renal effects of the agents. These effects are dose-dependent, and in many cases severe enough to pose the risk of ulcer perforation, upper gastrointestinal bleeding, and death, limiting the use of NSAID therapy. An estimated 10-20% of NSAID patients experience dyspepsia, and NSAID-associated upper gastrointestinal adverse events are estimated to result in 103,000 hospitalizations and 16,500 deaths per year in the United States, and represent 43% of drug-related emergency visits. NSAIDs, like all drugs, may interact with other medications. For example, concurrent use of NSAIDs and quinolones may increase the risk of quinolones' adverse central nervous system effects, including seizure.

In people with known vascular disease, acetylsalicylic acid is additionally known to reduce the incidence of non-fatal myocardial infarction, non-fatal stroke and vascular death by about a quarter. Acetylsalicylic acid has been shown to result in a reduction of coronary events, and also reduces the risk of ischemic stroke. Acetylsalicylic acid not only reduces the re-occurrence of vascular catastrophes, but probably also resulted in lower death rates. Unfortunately, acetylsalicylic acid also increases the risk for GI ulcers. This effect is present in both primary and secondary prevention trials. Most cardiovascular risk patients receive not only acetylsalicylic acid for secondary prevention of vascular disease, but also other interventions such as blood pressure control medications and statins.

It is expected that a skilled pharmacologist may adjust the amount of acetylsalicylic acid in a pharmaceutical composition or administered to a patient based upon standard techniques well known in the art. However, acetylsalicylic acid will typically be present in tablets or capsules in an amount of between about 50 mg and 1000 mg, including 75 mg, 81.25 mg, 100 mg, 150 mg, 162.5 mg, 250 mg, 300 mg, 325 mg, 400 mg, 500 mg, 650 mg, 800 mg and 1000 mg. Typical daily dosages will be in an amount ranging from 500 mg to about 10 g for analgesia or inflammation, and in an amount ranging from 50 mg to 500 mg for secondary prevention of cardiovascular disease.

B. Salicylic Acid

Salicylic acid is a monohydroxybenzoic acid, a type of phenolic acid and a beta hydroxy acid. This colorless crystalline organic acid is widely used in organic synthesis and functions as a plant hormone. It is derived from the metabolism of salicin. In addition to being a compound that is chemically similar to but not identical to the active component of acetylsalicylic acid (acetylsalicylic acid), it is probably best known for its use in anti-acne treatments. The salts and esters of salicylic acid are known as salicylates.

Salicylic acid has the formula $C_6H_4(OH)COOH$, where the —OH group is ortho to the carboxyl group. It is also known as 2-hydroxybenzenecarboxylic acid. It is poorly soluble in water (0.2 g/100 ml $H_2O$ at 20° C.). Acetylsalicylic acid (acetylsalicylic acid or ASA) can be prepared by the esterification of the phenolic hydroxyl group of salicylic acid with the acetate ion from acetic anhydride or acetic chloride.

Salicylic acid is biosynthesized from the amino acid phenylalanine. In *Arabidopsis thaliana* it can also be synthesized via a phenylalanine-independent pathway. Sodium salicylate is commercially prepared by treating sodium phenolate (the sodium salt of phenol) with carbon dioxide at high pressure (100 atm) and high temperature (390K)—a method known as the Kolbe-Schmitt reaction. Acidification of the product with sulfuric acid gives salicylic acid. It can also be prepared by the hydrolysis of Acetylsalicylic acid (acetylsalicylic acid) or methyl salicylate (oil of wintergreen) with a strong acid or base.

Salicylic acid is known for its ability to ease aches and pains and reduce fevers. These medicinal properties, particularly fever relief, have been known since ancient times, and it was used as an anti-inflammatory drug. Some researchers believe that salicylate is an essential micronutrient in the human diet, potentially qualifying as a vitamin, namely Vitamin S. In modern medicine, salicylic acid and its derivatives are used as constituents of some rubefacient products. For example, methyl salicylate is used as a liniment to soothe joint and muscle pain, and choline salicylate is used topically to relieve the pain of aphthous ulcers.

Cotton pads soaked in salicylic acid can be used to chemically exfoliate skin. As with other beta hydroxy acids, salicylic acid is a key ingredient in many skin-care products for the treatment of acne, psoriasis, calluses, corns, keratosis pilaris, and warts. It works as a keratolytic, bacteriocide and comedolytic agent by causing the cells of the epidermis to shed more readily, opening clogged pores and neutralizing bacteria within, preventing pores from clogging up again by constricting pore diameter, and allowing room for new cell growth. Because of its effect on skin cells, salicylic acid is used in several shampoos used to treat dandruff. Use of concentrated solutions of salicylic acid may cause hyperpigmentation on unpretreated skin for those with darker skin types (Fitzpatrick phototypes IV, V, VI), as well as with the lack of use of a broad spectrum sunblock. Bismuth subsalicylate, a salt of bismuth and salicyclic acid, is the active ingredient in stomach relief aids such as Pepto-Bismol®. Bismuth subsalicylate helps control nausea, heartburn, indigestion, upset stomach, and diarrhea. It is also a very mild antibiotic.

C. Omeprazole

Omeprazole (INN) is a proton pump inhibitor used in the treatment of dyspepsia, peptic ulcer disease (PUD), gastroesophageal reflux disease (GORD/GERD), laryngopharyngeal reflux (LPR) and Zollinger-Ellison syndrome. Omeprazole is one of the most widely prescribed drugs internationally and is available over the counter in some countries. It can be combined with the antibiotics clarithromycin and amoxicillin (or metronidazole in penicillin-hypersensitive patients) in the 7-14 day eradication triple therapy for *Helicobacter pylori*.

Some of the most frequent side effects of omeprazole (experienced by over 1% of those taking the drug) are headache, diarrhea, abdominal pain, nausea, dizziness, trouble awakening and sleep deprivation, although in clinical trials the incidence of these effects with omeprazole was mostly comparable to that found with placebo. Other side effects may include iron and vitamin B12 deficiency, although there is very little evidence to support this.

Proton pump inhibitors may be associated with a greater risk of fractures and *Clostridium difficile*-associated diarrhea. Patients are frequently administered the drugs in intensive care as a protective measure against ulcers, but this use is also associated with a 30% increase in occurrence of pneumonia. The risk of community-acquired pneumonia may also be higher in people taking PPIs. Since their introduction, proton pump inhibitors (especially omeprazole) have been associated with several cases of acute tubulointerstitial nephritis, an inflammation of the kidneys that often occurs as an adverse drug reaction. PPI use has also been associated with fundic gland polyposis.

Omeprazole is a competitive inhibitor of the enzymes CYP2C19 and CYP2C9, and may therefore interact with drugs that depend on them for metabolism, such as diazepam, escitalopram, and warfarin; the concentrations of these drugs may increase if they are used concomitantly with omeprazole. Clopidogrel (Plavix®) is an inactive prodrug that partially depends on CYP2C19 for conversion to its active form; inhibition of CYP2C19 blocks the activation of clopidogrel, thus reducing its effects and potentially increasing the risk of stroke or heart attack in people taking clopidogrel to prevent these events. Omeprazole is also a competitive inhibitor of p-glycoprotein, as are other PPIs.

Drugs that depend on stomach pH for absorption may interact with omeprazole; drugs that depend on an acidic environment (such as ketoconazole or atazanavir) will be poorly absorbed, whereas acid-labile antibiotics (such as erythromycin) will be absorbed to a greater extent than normal due to the more alkaline environment of the stomach. St. John's wort (*Hypericum perforatum*) and *Gingko biloba* significantly reduce plasma concentrations of omeprazole through induction of CYP3A4 and CYP2C19.

The absorption of omeprazole takes place in the small intestine and is usually completed within 3-6 hours. The systemic bioavailability of omeprazole after repeated dose is about 60%. Omeprazole bioavailability is significantly impaired by the presence of food and, therefore, patients should be advised to take omeprazole with a glass of water on an empty stomach (i.e., fast for at least 60 minutes before taking omeprazole). Additionally, most sources recommend that after taking omeprazole at least 30 minutes should be allowed to elapse before eating (at least 60 minutes for immediate-release omeprazole plus sodium bicarbonate products, such as Zegerid®), though some sources say that with delayed-release forms of omeprazole it is not necessary to wait before eating after taking the medication. Plasma protein binding is about 95%.

Omeprazole is completely metabolized by the cytochrome P450 system, mainly in the liver. Identified metabolites are the sulfone, the sulfide and hydroxy-omeprazole, which exert no significant effect on acid secretion. About 80% of an orally given dose is excreted as metabolites in the urine and the remainder is found in the feces, primarily originating from bile secretion.

Omeprazole is a racemate. It contains a tricoordinated sulfur in a pyramidal structure and therefore can exist in equal amounts of both the (S)- and (R)-enantiomers. In the acidic conditions of the stomach, both are converted to achiral products, which reacts with a cysteine group in H+/K+ ATPase, thereby inhibiting the ability of the parietal cells to produce gastric acid. Omeprazole undergoes a chiral shift in vivo which converts the inactive (R)-enantiomer to the active (S)-enantiomer doubling the concentration of the active form. This chiral shift is accomplished by the CYP2C19 isozyme of cytochrome P450, which is not found equally in all human populations. Those who do not metabolize the drug effectively are called "poor metabolizers." The proportion of the poor metabolizer phenotype varies widely between populations, from 2-2.5% in African-Americans and white Americans to >20% in Asians; several pharmacogenomics studies have suggested that PPI treatment should be tailored according to CYP2C19 metabolism status.

Omeprazole is available as tablets and capsules (containing omeprazole or omeprazole magnesium) in strengths of 10 mg, 20 mg, 40 mg, and in some markets 80 mg; and as a powder (omeprazole sodium) for intravenous injection. Most oral omeprazole preparations are enteric-coated, due to the rapid degradation of the drug in the acidic conditions of the stomach. This is most commonly achieved by formulating enteric-coated granules within capsules, enteric-coated tablets, and the multiple-unit pellet system (MUPS).

It is also available for use in injectable form (I.V.) in Europe, but not in the U.S. The injection pack is a combination pack consisting of a vial and a separate ampule of reconstituting solution. Each 10 ml clear glass vial contains a white to off-white lyophilised powder consisting of omeprazole sodium 42.6 mg equivalent to 40 mg of omeprazole.

Omeprazole tablets manufactured by AstraZeneca (notably Losec/Prilosec) are formulated as a "multiple unit pellet system" (MUPS). Essentially, the tablet consists of extremely small enteric-coated granules (pellets) of the omeprazole formulation inside an outer shell. When the tablet is immersed in an aqueous solution, as happens when the tablet reaches the stomach, water enters the tablet by osmosis. The contents swell from water absorption causing the shell to burst, releasing the enteric-coated granules. For most patients, the multiple-unit pellet system is of no advantage over conventional enteric-coated preparations. Patients for which the formulation is of benefit include those requiring nasogastric tube feeding and those with difficulty swallowing (dysphagia) because the tablets can be mixed with water ahead of time, releasing the granules into a slurry form, which is easier to pass down the feeding tube or to swallow than the pill.

The granules are manufactured in a fluid air bed system. Sugar spheres in suspension are sequentially sprayed with aqueous suspensions of omeprazole, a protective layer, an enteric coating and an outer layer to reduce granule aggregation. The granules are mixed with other excipients and compressed into tablets. Finally, the tablets are film-coated to improve the stability and appearance of the preparation.

In June 2004 the FDA approved an immediate release preparation of omeprazole and sodium bicarbonate that does not require an enteric coating. This preparation employs sodium bicarbonate as a buffer to protect omeprazole from gastric acid degradation. This allows for the production of chewable tablets. This combination preparation is marketed in the United States by Santarus under the brand name Zegerid. Zegerid is marketed as capsules, chewable tablets, and powder for oral suspension. Zegerid is most useful for those patients who suffer from nocturnal acid breakthrough (NAB) or those patients who desire immediate relief. In India it is marketed by Dr. Reddy's Laboratories as powder formulation with the brand name OMEZ-INSTA. It is reported to have additional benefits with patients suffering from alcoholic gastritis and life-style associated gastritis.

D. PA32540

PA32540 (Pozen Inc., Chapel Hill N.C.) is a tablet containing 325 mg enteric coated (EC) acetylsalicylic acid and 40 mg omeprazole. It is designed to reduce acetylsalicylic acid-related gastrointestinal toxicity while delivering a bioequivalent dose of acetylsalicylic acid. This tablet is unique in that omeprazole is not EC (delayed release formulation) or buffered as it is in other PPI products (Grubel et al., 2009). Instead, omeprazole is contained in the outer layer of the PA32540 tablet in an immediate release form, available for rapid dissolution. Its therapeutic activity is rapid and occurs prior to the dissolution of the acetylsalicylic acid component contained within the core of the multi-layered tablet (Grubel et al., 2009). To further ensure the sequential delivery of the two components, the acetylsalicylic acid core is coated by polymers which prevent dissolution until the pH of the surrounding environment is >5.5. A bioequivalence study (PA32540-104) demonstrated that, with respect to salicylic acid pharmacokinetics, PA32540 is bioequivalent to commercially available 325 mg EC acetylsalicylic acid (Fort et al., 2008). Compared to 81 mg EC acetylsalicylic acid, PA32540 was associated with greater inhibition of in vivo thromboxane generation and no greater upper gastrointestinal damage by Lanza score (Grubel et al., 2009).

III. Disease States

NSAIDs find use in treating a variety of inflammatory diseases and for the control of pain. The following listing of diseases (or risk factors) that are amenable to treatment with acetylsalicylic acid are exemplary in nature and not meant to be limiting.

A. Ankylosing Spondylitis

AS is a disease subset within a broader disease classification of spondyloarthropathy. Patients affected with the various subsets of spondyloarthropathy have disease etiologies that are often very different, ranging from bacterial infections to inheritance. Yet, in all subgroups, the end result of the disease process is axial arthritis. Despite the early clinically differences seen in the various patient populations, many of them end up nearly identical after a disease course of ten-to-twenty years. Recent studies suggest the mean time to clinical diagnosis of ankylosing spondylitis from disease onset of disease is 7.5 years. (Khan, 1998). These same studies suggest that the spondyloarthropathies may have prevalence close to that of rheumatoid arthritis (Feldtkeller et al., 2003; Doran et al., 2003).

AS is a chronic systemic inflammatory rheumatic disorder of the axial skeleton with or without extraskeletal manifestations. Sacroiliac joints and the spine are primarily affected, but hip and shoulder joints, and less commonly peripheral joints or certain extra-articular structures such as the eye, vasculature, nervous system, and gastrointestinal system may also be involved. Its etiology is not yet fully understood. It is strongly associated with the major histocompatibility class I (MHC I) HLA-B27 allele. AS affects individuals in the prime of their life and is feared because of its potential to cause chronic pain and irreversible damage of tendons, ligaments, joints, and bones. AS may occur alone or in association with another form of spondyloarthropathy such as reactive arthritis, psoriasis, psoriatic arthritis, enthesitis, ulcerative colitis, irritable bowel disease, or Crohn's disease, in which case it is classified as secondary AS.

Typically, the affected sites include the discovertebral, apophyseal, costovertebral, and costotransverse joints of the spine, and the paravertebral ligamentous structures. Inflammation of the entheses, which are sites of musculotendinous and ligamentous attachment to bones, is also prominent in this disease. The site of enthesitis is known to be infiltrated by plasma cells, lymphocytes, and polymorphonuclear cells. The inflammatory process frequently results in gradual fibrous and bony ankylosis.

Delayed diagnosis is common because symptoms are often attributed to more common back problems. A dramatic loss of flexibility in the lumbar spine is an early sign of AS. Other common symptoms include chronic pain and stiffness in the lower back which usually starts where the lower spine is joined to the pelvis, or hip.

Although most symptoms begin in the lumbar and sacroiliac areas, they may involve the neck and upper back as well. Arthritis may also occur in the shoulder, hips and feet. Some patients have eye inflammation, and more severe cases must be observed for heart valve involvement. The most frequent presentation is back pain, but disease can begin atypically in peripheral joints, especially in children and women, and rarely with acute iritis (anterior uveitis). Additional early symptoms and signs are diminished chest expansion from diffuse costovertebral involvement, low-grade fever, fatigue, anorexia, weight loss, and anemia. Recurrent back pain—often nocturnal and of varying intensity—is an eventual complaint, as is morning stiffness typically relieved by activity. A flexed or bent-over posture eases back pain and paraspinal muscle spasm; thus, some degree of kyphosis is common in untreated patients.

Systemic manifestations occur in ⅓ of patients. Recurrent, usually self-limited, acute iritis (anterior uveitis) rarely is protracted and severe enough to impair vision. Neurologic signs can occasionally result from compression radiculitis or sciatica, vertebral fracture or subluxation, and cauda equina syndrome (which consists of impotence, nocturnal urinary incontinence, diminished bladder and rectal sensation, and absence of ankle jerks). Cardiovascular manifestations can include aortic insufficiency, angina, pericarditis, and ECG conduction abnormalities. A rare pulmonary finding is upper lobe fibrosis, occasionally with cavitation that may be mistaken for TB and can be complicated by infection with *Aspergillus*.

AS is characterized by mild or moderate flares of active spondylitis alternating with periods of almost or totally inactive inflammation. Proper treatment in most patients results in minimal or no disability and in full, productive lives despite back stiffness. Occasionally, the course is severe and progressive, resulting in pronounced incapacitating deformities. The prognosis is bleak for patients with refractory iritis and for the rare patient with secondary amyloidosis.

The ESR and other acute-phase reactants (e.g., C-reactive protein and serum Ig levels) are mildly elevated in most patients with active AS. Tests for IgM rheumatoid factor and antinuclear antibodies are negative. A positive test for HLA-B27 is usual but not invariable and not specific (a negative test is more useful in helping to exclude AS than a positive test is in diagnosing it). This test is not necessary in patients with typical disease.

Diagnosis must be confirmed by x-ray. The earliest abnormalities (pseudo-widening from subchondral erosions, sclerosis or later narrowing) occur in the sacroiliac joints. Early changes in the spine are upper lumbar vertebral squaring and demineralization, spotty ligamentous calcification, and one or two evolving syndesmophytes. The classic bamboo spine with prominent syndesmophytes and diffuse paraspinal ligamentous calcification is not useful for early diagnosis; these changes develop in a minority of patients over an average period of 10 years.

The severity of joint involvement and the degree of systemic symptoms vary greatly from one individual to another. Early, accurate diagnosis and therapy may minimize years of pain and disability. Joint discomfort may be relieved with drugs. Treatment plans usually address prevention, delay, or correction of the deformity and psychosocial and rehabilitation needs. For proper posture and joint motion, daily exercise and other supportive measures (e.g., postural training, therapeutic exercise) are vital to strengthen muscle groups that oppose the direction of potential deformities (i.e., strengthen the extensor rather than flexor muscle groups). Reading while lying prone and thus extending the neck may help keep the back flexible.

NSAIDs facilitate exercise and other supportive measures by suppressing articular inflammation, pain, and muscle spasm. Most NSAIDs are of proven value in AS, but tolerance and toxicity, rather than marginal differences in efficacy, dictate drug choice. Patients should be monitored and warned of potential adverse reactions. The daily dose of NSAIDs should be as low as possible, but maximum doses of a drug such as indomethacin may be needed with active disease. Drug withdrawal should be attempted only slowly, after systemic and articular signs of active disease have been suppressed for several months. Several new NSAIDs, referred to as COX-2 drugs because they inhibit cyclooxygenase-2, provide equal effectiveness to drugs that inhibit COX-1 with less chance of adverse effects on the gastric mucosa, and platelet aggregation.

B. Psoriatic Arthritis

Psoriasis is an inflammatory and proliferative skin disorder with a prevalence of 1.5-3%. Approximately 20% of patients with psoriasis develop a characteristic form of arthritis that has several patterns. Some individuals present with joint symptoms first but in the majority, skin psoriasis presents first. About one-third of patients have simultaneous exacerbations of their skin and joint disease and there is a topographic relationship between nail and distal interphalangeal joint disease. Although the inflammatory processes which link skin, nail and joint disease remain elusive, an immune-mediated pathology is implicated.

Psoriatic arthritis (PsA) is a chronic inflammatory arthropathy characterized by the association of arthritis and psoriasis and was recognized as a clinical entity distinct from rheumatoid arthritis (RA). Subsequent studies have revealed that PsA shares a number of genetic, pathogenic and clinical features with other spondyloarthropathies (SpAs), a group of diseases that comprise ankylosing spondylitis, reactive arthritis and enteropathic arthritis. The notion that PsA belongs to the SpA group has recently gained further support from imaging studies demonstrating widespread enthesitis in the, including PsA but not RA. More specifically, enthesitis has been postulated to be one of the earliest events occurring in the SpAs, leading to bone remodeling and ankylosis in the spine, as well as to articular synovitis when the inflamed entheses are close to peripheral joints. However, the link between enthesitis and the clinical manifestations in PsA remains largely unclear, as PsA can present with fairly heterogeneous patterns of joint involvement with variable degrees of severity. Thus, other factors must be posited to account for the multifarious features of PsA, only a few of which (such as the expression of the HLA-B27 molecule, which is strongly associated with axial disease) have been identified. As a consequence, it remains difficult to map the disease manifestations to specific pathogenic mechanisms, which means that the treatment of this condition remains largely empirical.

Family studies have suggested a genetic contribution to the development of PsA. Other chronic inflammatory forms of arthritis, such as ankylosing spondylitis and rheumatoid arthritis, are thought to have a complex genetic basis. However, the genetic component of PsA has been difficult to assess for several reasons. There is strong evidence for a genetic predisposition to psoriasis alone that may mask the genetic factors that are important for the development of PsA. Although most would accept PsA as a distinct disease entity, at times there is a phenotypic overlap with rheumatoid arthritis and ankylosing spondylitis. Also, PsA itself is not a homogeneous condition and various subgroups have been proposed.

C. Rhematoid Arthritis

The exact etiology of RA remains unknown, but the first signs of joint disease appear in the synovial lining layer, with proliferation of synovial fibroblasts and their attachment to the articular surface at the joint margin. Subsequently, macrophages, T cells and other inflammatory cells are recruited into the joint, where they produce a number of mediators, including the cytokines interleukin-1 (IL-1), which contributes to the chronic sequalae leading to bone and cartilage destruction, and tumour necrosis factor (TNF-α), which plays a role in inflammation. The concentration of IL-1 in plasma is significantly higher in patients with RA than in healthy individuals and, notably, plasma IL-1 levels correlate with RA disease activity. Moreover, synovial fluid levels of IL-1 are correlated with various radiographic and histologic features of RA.

In normal joints, the effects of these and other proinflammatory cytokines are balanced by a variety of anti-inflammatory cytokines and regulatory factors. The significance of this cytokine balance is illustrated in juvenile RA patients, who have cyclical increases in fever throughout the day. After each peak in fever, a factor that blocks the effects of IL-1 is found in serum and urine. This factor has been isolated, cloned and identified as IL-1 receptor antagonist (IL-1ra), a member of the IL-1 gene family. IL-1ra, as its name indicates, is a natural receptor antagonist that competes with IL-1 for binding to type I IL-1 receptors and, as a result, blocks the effects of IL-1. A 10- to 100-fold excess of IL-1ra may be needed to block IL-1 effectively; however, synovial cells isolated from patients with RA do not appear to produce enough IL-1ra to counteract the effects of IL-1.

D. Systemic Lupus Erythematosus

There has also been no known cause for autoimmune diseases such as systemic lupus erythematosus. Systemic lupus erythematosus (SLE) is an autoimmune rheumatic disease characterized by deposition in tissues of autoantibodies and immune complexes leading to tissue injury. In contrast to autoimmune diseases such as MS and type 1 diabetes mellitus, SLE potentially involves multiple organ systems directly, and its clinical manifestations are diverse and variable. For example, some patients may demonstrate primarily skin rash and joint pain, show spontaneous remissions, and require little medication. At the other end of the spectrum are patients who demonstrate severe and progressive kidney involvement that requires therapy with high doses of steroids and cytotoxic drugs such as cyclophosphamide.

The serological hallmark of SLE, and the primary diagnostic test available, is elevated serum levels of IgG antibodies to constituents of the cell nucleus, such as double-stranded DNA (dsDNA), single-stranded DNA (ss-DNA), and chromatin. Among these autoantibodies, IgG anti-ds-DNA antibodies play a major role in the development of lupus glomerulonephritis (GN). Glomerulonephritis is a serious condition in which the capillary walls of the kidney's blood purifying glomeruli become thickened by accretions on the epithelial side of glomerular basement membranes. The disease is often chronic and progressive and may lead to eventual renal failure. The mechanisms by which autoantibodies are induced in these autoimmune diseases remains unclear. As there has been no known cause of SLE, to which diagnosis and/or treatment could be directed, treatment has been directed to suppressing immune responses, for example with macrolide antibiotics, rather than to an underlying cause.

E. Juvenile Rheumatoid Arthritis

'Juvenile rheumatoid arthritis' (JRA), a term for the most prevalent form of arthritis in children, is applied to a family of illnesses characterized by chronic inflammation and hypertrophy of the synovial membranes. The term overlaps, but is not completely synonymous, with the family of illnesses referred to as juvenile chronic arthritis and/or juvenile idiopathic arthritis in Europe. A proposed pathogenesis of rheumatoid disease in adults and children involves complex interactions between innate and adaptive immunity. This complexity lies at the core of the difficulty of unraveling disease pathogenesis.

Both innate and adaptive immune systems use multiple cell types, a vast array of cell surface and secreted proteins, and interconnected networks of positive and negative feedback. Furthermore, while separable in thought, the innate and adaptive wings of the immune system are functionally intersected, and pathologic events occurring at these intersecting points are likely to be highly relevant to our understanding of pathogenesis of adult and childhood forms of chronic arthritis.

Polyarticular JRA is a distinct clinical subtype characterized by inflammation and synovial proliferation in multiple joints (four or more), including the small joints of the hands. This subtype of JRA may be severe, because of both its multiple joint involvement and its capacity to progress rapidly over time. Although clinically distinct, polyarticular JRA is not homogeneous, and patients vary in disease manifestations, age of onset, prognosis, and therapeutic response. These differences very likely reflect a spectrum of variation in the nature of the immune and inflammatory attack that can occur in this disease.

F. Early Arthritis

The clinical presentation of different inflammatory arthropathies is similar early in the course of disease. As a result, it is often difficult to distinguish patients who are at risk of developing the severe and persistent synovitis that leads to erosive joint damage from those whose arthritis is more self-limited. Such distinction is critical in order to target therapy appropriately, treating aggressively those with erosive disease and avoiding unnecessary toxicity in patients with more self-limited disease. Current clinical criteria for diagnosing erosive arthropathies such as rheumatoid arthritis (RA) are less effective in early disease and traditional markers of disease activity such as joint counts and acute phase response do not adequately identify patients likely to have poor outcomes. Parameters reflective of the pathologic events occurring in the synovium are most likely to be of significant prognostic value.

Recent efforts to identify predictors of poor outcome in early inflammatory arthritis have identified the presence of RA specific autoantibodies, in particular antibodies towards citrullinated peptides, to be associated with erosive and persistent disease in early inflammatory arthritis cohorts. On the basis of this, a cyclical citrullinated peptide (CCP) has been developed to assist in the identification of anti-CCP antibodies in patient sera. Using this approach, the presence of anti-CCP antibodies has been shown to be specific and sensitive for RA, can distinguish RA from other arthropathies, and can potentially predict persistent, erosive synovitis before these outcomes become clinically manifest. Importantly, anti-CCP antibodies are often detectable in sera many years prior to clinical symptoms suggesting that they may be reflective of subclinical immune events.

The clinical presentation of different inflammatory arthropathies is similar early in the course of disease. As a result, it is often difficult to distinguish patients who are at risk of developing the severe and persistent synovitis that leads to erosive joint damage from those whose arthritis is more self-limited. Such distinction is critical in order to target therapy appropriately, treating aggressively those with erosive disease and avoiding unnecessary toxicity in patients with more self-limited disease. Current clinical criteria for diagnosing erosive arthropathies such as rheumatoid arthritis (RA) are less effective in early disease and traditional markers of disease activity such as joint counts and acute phase response do not adequately identify patients likely to have poor outcomes. Parameters reflective of the pathologic events occurring in the synovium are most likely to be of significant prognostic value.

Recent efforts to identify predictors of poor outcome in early inflammatory arthritis have identified the presence of RA specific autoantibodies, in particular antibodies towards citrullinated peptides, to be associated with erosive and persistent disease in early inflammatory arthritis cohorts. On the basis of this, a cyclical citrullinated peptide (CCP) has been developed to assist in the identification of anti-CCP antibodies in patient sera. Using this approach, the presence of anti-CCP antibodies has been shown to be specific and sensitive for RA, can distinguish RA from other arthropathies, and can potentially predict persistent, erosive synovitis before these outcomes become clinically manifest. Importantly, anti-CCP antibodies are often detectable in sera many years prior to clinical symptoms suggesting that they may be reflective of subclinical immune events.

G. Osteoarthritis

Osteoarthritis (OA) also known as degenerative arthritis or degenerative joint disease, is a group of mechanical abnormalities involving degradation of joints, including articular cartilage and subchondral bone. Symptoms may include joint pain, tenderness, stiffness, locking, and sometimes an effusion. A variety of causes—hereditary, developmental, metabolic, and mechanical—may initiate processes leading to loss of cartilage. When bone surfaces become less well protected by cartilage, bone may be exposed and damaged. As a result of decreased movement secondary to pain, regional muscles may atrophy, and ligaments may become more lax.

Treatment generally involves a combination of exercise, lifestyle modification, and analgesics. If pain becomes debilitating, joint replacement surgery may be used to improve the quality of life. OA is the most common form of arthritis, and the leading cause of chronic disability in the United States. It affects about 8 million people in the United Kingdom and nearly 27 million people in the United States.

The main symptom is pain, causing loss of ability and often stiffness. "Pain" is generally described as a sharp ache, or a burning sensation in the associate muscles and tendons. OA can cause a crackling noise (called "crepitus") when the affected joint is moved or touched, and patients may experience muscle spasm and contractions in the tendons. Occasionally, the joints may also be filled with fluid. Humid and cold weather increases the pain in many patients.

OA commonly affects the hands, feet, spine, and the large weight bearing joints, such as the hips and knees, although in theory, any joint in the body can be affected. As OA progresses, the affected joints appear larger, are stiff and painful, and usually feel better with gentle use but worse with excessive or prolonged use, thus distinguishing it from rheumatoid arthritis.

In smaller joints, such as at the fingers, hard bony enlargements, called Heberden's nodes (on the distal interphalangeal joints) and/or Bouchard's nodes (on the proximal interphalangeal joints), may form, and though they are not necessarily painful, they do limit the movement of the fingers significantly. OA at the toes leads to the formation of bunions, rendering them red or swollen. Some people notice these physical changes before they experience any pain. OA is the most common cause of joint effusion, sometimes called water on the knee in lay terms, an accumulation of excess fluid in or around the knee joint.

Exercise, including running in the absence of injury, has not been found to increase one's risk of developing osteoarthritis. Cracking ones knuckles also does not appear to play a role.[8] Some investigators believe that mechanical stress on joints underlies all osteoarthritis, with many and varied sources of mechanical stress, including misalignments of bones caused by congenital or pathogenic causes; mechanical injury; overweight; loss of strength in muscles supporting joints; and impairment of peripheral nerves, leading to sudden or uncoordinated movements that overstress joints.

Primary osteoarthritis is a chronic degenerative disorder related to but not caused by aging, as there are people well into their nineties who have no clinical or functional signs of the disease. As a person ages, the water content of the cartilage decreases as a result of a reduced proteoglycan content, thus causing the cartilage to be less resilient. Without the protective effects of the proteoglycans, the collagen fibers of the cartilage can become susceptible to degradation and thus exacerbate the degeneration. Inflammation of the surrounding joint capsule can also occur, though often mild (compared to that which occurs in rheumatoid arthritis). This can happen as breakdown products from the cartilage are released into the synovial space, and the cells lining the joint attempt to remove them. New bone outgrowths, called "spurs" or osteophytes, can form on the margins of the joints, possibly in an attempt to improve the congruence of the articular cartilage surfaces. These bone changes, together with the inflammation, can be both painful and debilitating.

Both primary generalized nodal OA and erosive OA (EOA. also called inflammatory OA) are sub-sets of primary OA. EOA is a much less common, and more aggressive inflammatory form of OA which often affects the DIPs and has characteristic changes on X-Ray.

This type of OA is caused by other factors but the resulting pathology is the same as for primary OA, including congenital disorders of joints, diabetes, inflammatory diseases (such as Perthes' disease, Lyme disease, and all chronic forms of arthritis (e.g., costochondritis, gout, and rheumatoid arthritis)), gout, injury to joints as a result of an accident or orthodontic operations, septic arthritis, ligamentous deterioration or instability, Marfan syndrome, obesity, alkaptonuria, hemochromatosis and Wilson's disease.

Diagnosis is made with reasonable certainty based on history and clinical examination. X-rays may confirm the diagnosis. The typical changes seen on X-ray include: joint space narrowing, subchondral sclerosis (increased bone formation around the joint), subchondral cyst formation, and osteophytes. Plain films may not correlate with the findings on physical examination or with the degree of pain. Usually other imaging techniques are not necessary to clinically diagnose osteoarthritis.

Lifestyle modification (such as weight loss and exercise) and analgesics are the mainstay of treatment. Acetaminophen/paracetamol is used first line and NSAIDS are only recommended as add on therapy if pain relief is not sufficient. This is due to the relative greater safety of acetaminophen. Acetaminophen is the first line treatment for OA. For mild to moderate symptoms effectiveness is similar to NSAIDs, though for more severe symptoms NSAIDs may be more effective. Non-steroidal anti-inflammatory drugs (NSAID) such as ibuprofen while more effective in severe cases are associated with greater side effects such as gastrointestinal bleeding. Another class of NSAIDs, COX-2 selective inhibitors (such as celecoxib) are equally effective to NSAIDs but no safer in terms of side effects. They are however much more expensive. There are several NSAIDs available for topical use including diclofenac. They have fewer systemic side-effects and at least some therapeutic effect. While opioid analgesic such as morphine and fentanyl improve pain this benefit is outweighed by frequent adverse events and thus they should not routinely be used.

Oral steroids are not recommended in the treatment of OA because of their modest benefit and high rate of adverse effects. Injection of glucocorticoids (such as hydrocortisone) leads to short term pain relief that may last between a few weeks and a few months. Topical capsaicin and joint injections of hyaluronic acid have not been found to lead to significant improvement. Tanezumab, a monoclonal antibody that binds and inhibits nerve growth factor, appears to relieve joint pain enough to improve function in people with osteoarthritis of the knee.

H. Neuroinflammation

Neuroinflammation encapsulates the idea that microglial and astrocytic responses and actions in the central nervous system have a fundamentally inflammation-like character, and that these responses are central to the pathogenesis and progression of a wide variety of neurological disorders. This idea originated in the field of Alzheimer's disease (Griffin et al., 1989; Rogers et al., 1988), where it has revolutionized our understanding of this disease (Akiyama et al., 2000). These ideas have been extended to other neurodegenerative diseases (Eikelenboom et al., 2002; Orr et al., 2002; Ishizawa & Dickson, 2001), to ischemic/toxic diseases (Gehrmann et al., 1995; Touzani et al., 1999), to tumor biology (Graeber et al., 2002) and even to normal brain development.

Neuroinflammation incorporates a wide spectrum of complex cellular responses that include activation of microglia and astrocytes and induction of cytokines, chemokines, complement proteins, acute phase proteins, oxidative injury, and related molecular processes. These events may have detrimental effects on neuronal function, leading to neuronal injury, further glial activation, and ultimately neurodegeneration.

Neuroinflammation is a new and rapidly expanding field that has revolutionized our understanding of chronic neurological diseases. This field encompasses research ranging from population studies to signal transduction pathways, and investigators with backgrounds in fields as diverse as pathology, biochemistry, molecular biology, genetics, clinical medicine, and epidemiology. Important contributions to this field have come from work with populations, with patients, with postmortem tissues, with animal models, and with in vitro systems.

I. Cardiovascular Disease

Heart disease or cardiovascular disease are the class of diseases that involve the heart or blood vessels (arteries and veins). While the term technically refers to any disease that affects the cardiovascular system, it is usually used to refer to those related to atherosclerosis (arterial disease). These conditions usually have similar causes, mechanisms, and treatments.

Most countries face high and increasing rates of cardiovascular disease. Each year, heart disease kills more Americans than cancer. In recent years, cardiovascular risk in women has been increasing and has killed more women than breast cancer. A large histological study showed vascular injury accumulates from adolescence, making primary prevention efforts necessary from childhood. By the time that heart problems are detected, the underlying cause (atherosclerosis) is usually quite advanced, having progressed for decades. There is therefore increased emphasis on preventing atherosclerosis by modifying risk factors, such as healthy eating, exercise, and avoidance of smoking.

Population based studies show that the precursors of heart disease start in adolescence. The process of atherosclerosis evolves over decades, and begins as early as childhood. The Pathobiological Determinants of Atherosclerosis in Youth Study demonstrated that intimal lesions appear in all the aortas and more than half of the right coronary arteries of youths aged 7-9 years. However, most adolescents are more concerned about other risks such as HIV, accidents, and cancer than cardiovascular disease. This is extremely important considering that 1 in 3 people will die from complications attributable to atherosclerosis. In order to stem the tide education and awareness that cardiovascular disease poses the greatest threat and measures to prevent or reverse this disease must be taken.

Obesity and diabetes mellitus are often linked to cardiovascular disease, as are a history of chronic kidney disease and hypercholesterolaemia. In fact, cardiovascular disease is the most life threatening of the diabetic complications and diabetics are two- to four-fold more likely to die of cardiovascular-related causes than nondiabetics.

The causes, prevention, and/or treatment of all forms of cardiovascular disease remain active fields of biomedical research, with hundreds of scientific studies being published on a weekly basis. A fairly recent emphasis is on the link between low-grade inflammation that hallmarks atherosclerosis and its possible interventions. C-reactive protein (CRP) is an common inflammatory marker that has been found to be present in increased levels in patients at risk for cardiovascular disease. Also osteoprotegerin which involved with regulation of a key inflammatory transcription factor called NF-κB has been found to be a risk factor of cardiovascular disease and mortality.

Acetylsalicylic acid has historically been used at moderate to high doses to decrease pain and reduce swelling and, more recently, low dose acetylsalicylic acid has been used to treat and prevent cardiovascular disease (CVD), including conditions such as heart attack, stroke, and peripheral artery disease (poor circulation) in the legs. Many large trials have shown that acetylsalicylic acid has benefits for virtually all people who have had a heart attack, stroke, or peripheral artery disease, as well as angina, stents, or bypass surgery, and even men and women who have no signs or symptoms but have an increased risk of a first heart attack (e.g., due to diabetes or other risk factors). However, the benefits of acetylsalicylic acid must be weighed against its possible side effects. People with a higher risk of heart attack have a greater potential for benefit.

Acetylsalicylic acid inhibits the clumping of platelets (even in low doses), has pain killing effects (in medium doses), and has antiinflammatory effects (in high doses). Platelets are tiny cell fragments circulating in the blood that have a role in blood clotting. Under normal circumstances, platelets clump together and help form blood clots that stop bleeding. However, in coronary heart disease, platelets clump together in narrowed arteries, which leads to the development of a clot within the artery; the platelet "plug" itself and/or the clot that forms can block blood flow. This blockage can have significant consequences. When the arteries that supply blood to the brain are blocked, the supply of oxygen to the brain is decreased. The consequences of this depend upon the duration and the extent to which blood flow is cut off.

The benefits of acetylsalicylic acid have been studied in a wide range of patients. Several large trials, primarily among men, have shown that acetylsalicylic acid can prevent a first heart attack in people who have no signs or symptoms of cardiovascular disease (this is called primary prevention). However, these trials could not detect the effects of acetylsalicylic acid on the risk of stroke and death related to cardiovascular disease. In one trial of women, acetylsalicylic acid reduced the risk of a first stroke and also decreased the risk of a first heart attack among those age 65 and over Expert groups recommend acetylsalicylic acid to prevent heart attack or stroke for healthy men and women when the benefits outweigh the risks; this includes people with a 10-year risk of a coronary event of at least 6 to 10 percent. The 10-year risk can be calculated here for women (calculator 1) and for men (calculator 2). The recommended daily dose of acetylsalicylic acid for prevention of heart attack and stroke is between 75 and 100 mg.

IV. Pharmaceutical Delivery

One embodiment is directed to a method for delivering a pharmaceutical composition to a patient in need thereof, comprising: administering to said patient a pharmaceutical composition in unit dose form comprising acetylsalicylic acid, or pharmaceutically acceptable salt thereof, and omeprazole, or pharmaceutically acceptable salt thereof, wherein said omeprazole, or pharmaceutically acceptable salt thereof, is released from said unit dose form at a pH of from about 0 or greater to target: a mean % time at which intragastric pH remains at about 4.0 or greater for about a 24 hour period after reaching steady state of at least about 41%.

Steady state levels of acetylsalicylic acid or omeprazole are generally reached in about 4 to 5 days, about 5 to 6 days, about 6 to 7 days, about 7 to 8 days, about 8 to 9 days, or about 9 to 10 days after delivery (twice daily) of the pharmaceutical compositions in unit dose form disclosed herein. In other embodiments, steady state levels of acetylsalicylic acid or omeprazole are reached in about 4 days, about 5 days, about 6 days, about 7 days, about 8 days, about 9 days, or about 10 days.

In other embodiments, the mean % time at which intragastric pH remains at about 4.0 or greater for a 24 hour period after reaching steady state is at least about 40%, about 45%, about 50%, about 55%, about 60%, about 65%, about 70%, about 71%, about 75%, about 77%, about 80%, about 85%, about 90%, or about 95%.

V. Pharmaceutical Formulations

In an even further embodiment, the pharmaceutical composition in unit dose form is a multilayer tablet comprising at least one core and at least a first layer and a second layer, wherein said core comprises acetylsalicylic acid, or pharmaceutically acceptable salt thereof; said first layer is a coating that at least begins to release the acetylsalicylic acid, or pharmaceutically acceptable salt thereof, when the pH of the surrounding medium of about 3.5 or greater; said second layer is omeprazole, or pharmaceutically acceptable salt thereof, wherein said omeprazole, or pharmaceutically acceptable salt thereof, is released at a pH of from about 0 or greater.

In an even further embodiment, omeprazole, or pharmaceutically acceptable salt thereof, is released at a pH of from 0 or greater.

In another embodiment, omeprazole, or pharmaceutically acceptable salt thereof, is released at a pH of from about 1 or greater.

In a further embodiment, omeprazole, or pharmaceutically acceptable salt thereof, is released at a pH of from 1 or greater.

In still another embodiment, omeprazole, or pharmaceutically acceptable salt thereof, is released at a pH of from about 0 to about 2.

In yet a further embodiment, omeprazole, or pharmaceutically acceptable salt thereof, is released at a pH of from 0 to 2.

In yet still another embodiment, at least a portion of said omeprazole, or pharmaceutically acceptable salt thereof, is not coated with an enteric coating.

In even yet still another embodiment, the first layer is an enteric coating.

In an even further embodiment, the pharmaceutical composition in unit dose form is a multilayer tablet comprising a core comprising acetylsalicylic acid, or pharmaceutically acceptable salt thereof, and a first layer comprising a coating that at least begins releasing the acetylsalicylic acid when the pH of the surrounding medium is about 3.5 or greater and a second layer comprising omeprazole, or pharmaceutically acceptable salt thereof, wherein at least a portion of said omeprazole, or pharmaceutically acceptable salt thereof, is not surrounded by an enteric coating.

In another embodiment, the first layer is a coating that at least begins to release the acetylsalicylic acid when the pH of the surrounding medium is about 4.0, 4.5, 5.0 or greater. In still yet another embodiment, said first layer begins to release the acetylsalicylic acid when the pH of the surrounding medium is at about 4.0 or greater.

In a further embodiment, said first layer begins to release the acetylsalicylic acid when the pH of the surrounding medium is at about 4.5 or greater.

In yet a further embodiment, said first layer begins to release the acetylsalicylic acid when the pH of the surrounding medium is at about 5.0 or greater.

In one embodiment, at least about 95% of the omeprazole, or pharmaceutically acceptable salt thereof, is not surrounded by an enteric coating.

In another embodiment, at least about 99% of the omeprazole, or pharmaceutically acceptable salt thereof, is not surrounded by an enteric coating. In yet another embodiment, at least about 99.5% of the omeprazole, or pharmaceutically acceptable salt thereof, is not surrounded by an enteric coating.

In yet another embodiment, the multilayer tablet is substantially free of sodium bicarbonate.

In still another embodiment, the multilayer tablet is completely (i.e., 100%) free of sodium bicarbonate.

In one embodiment, the dosing regimen is twice a day.

In another embodiment, the doses can be separated by a period of at least about 10 hours.

In another embodiment, the pharmaceutical composition in unit dose form is given about 1 hour before a patient ingests a meal.

In another embodiment, the pharmaceutical compositions of the present disclosure may be administered therapeutically to patients either short term or over a longer period of time, for example chronically.

In other embodiments, long-term or chronic administration of the pharmaceutical compositions disclosed herein can result in intragastric pH being at least about 4.0 or greater a higher percentage of time per 24 hour period versus short-term administration. For example, administration of certain pharmaceutical compositions may result in a higher percentage time of intragastric pH being greater than about 4.0 on Day 3, 5 or 7 versus Day 1 of treatment.

In another embodiment, the method for delivering a pharmaceutical composition to a patient in need thereof, comprises administering to the patient a pharmaceutical composition in unit dose form comprising acetylsalicylic acid, or pharmaceutically acceptable salt thereof, and omeprazole, or pharmaceutically acceptable salt thereof, wherein intragastric pH is increased to at least about 4.0 within one hour of administration.

In another embodiment, intragastric pH is increased to at least about 4.0 or greater within 30 or 45 minutes of administration The pharmaceutical compositions disclosed herein include, but are not limited to, for example, tablets and capsules that can be made in accordance with methods that are standard in the art (see, e.g., Remington's Pharmaceutical Sciences, 16$^{th}$ ed., A. Oslo editor, Easton, Pa. (1980)).

Suitable carriers include, but are not limited to: water; salt solutions; alcohols; gum arabic; vegetable oils; benzyl alcohols; polyethylene glycols; gelatin; carbohydrates such as lactose, amylose or starch; magnesium stearate; talc; silicic acid; paraffin; perfume oil; fatty acid esters; hydroxymethylcellulose; polyvinyl pyrrolidone; etc.

The pharmaceutical compositions disclosed herein can be sterilized and, if desired, mixed with, for example, auxiliary agents, such as, for example, preservatives; stabilizers; buffers; coloring agents; and flavoring agents.

In one embodiment, at least one of the layers comprising the pharmaceutical compositions disclosed herein may be applied using standard coating techniques. The layer materials may be dissolved or dispersed in organic or aqueous solvents. The layer materials may include, but are not limited to, for example, one or more of the following materials: methacrylic acid copolymers, shellac, hydroxypropylmethcellulose phthalate, polyvinyl acetate phthalate, hydroxypropylmethyl-cellulose trimellitate, carboxymethylethyl-cellulose, cellulose acetate phthalate, and/or other suitable polymer(s). The pH at which the first layer dissolves can be controlled by the polymer or combination of polymers selected and/or ratio of pendant groups. For example, dissolution characteristics of the polymer film can be altered by the ratio of free carboxyl groups to ester groups. The layers may also contain pharmaceutically acceptable plasticizers, such as, for example, triethyl citrate, dibutyl phthalate, triacetin, polyethylene glycols, polysorbates or other plasticizers. Additives, such as, for example, dispersants, colorants, anti-adhering, and anti-foaming agents may also be used.

In one embodiment, the pharmaceutical compositions disclosed herein can be in the form of a bi- or multi-layer tablet. In a bi-layer tablet, one portion/layer of the tablet contains the omeprazole, or pharmaceutically acceptable salt thereof, in the required dose along with appropriate excipients, agents to aid dissolution, lubricants, fillers, etc.; and a second portion/layer of the tablet contains the NSAID in the required dose along with other excipients, dissolution agents, lubricants, fillers, etc.

In another embodiment, the acetylsalicylic acid portion/layer is surrounded by a polymeric coating that dissolves at a pH of at least about 3.5 or greater.

In yet another embodiment, the acetylsalicylic acid portion/layer is surrounded by a polymeric coating that dissolves at a pH of at least about 4 or greater.

The acetylsalicylic acid, or pharmaceutically acceptable salt thereof, may be granulated by methods such as slugging, low- or high-shear granulation, wet granulation, or fluidized-bed granulation. Of these processes, slugging generally produces tablets of less hardness and greater friability. Low-shear granulation, high-shear granulation, wet granulation and fluidized-bed granulation generally produce harder, less friable tablets.

VI. Examples

The invention is further defined in the following Example(s). It should be understood the Example(s) are given by way of illustration only. From the above discussion and the Example(s), one skilled in the art can ascertain the essential characteristics of the invention, and without departing from the spirit and scope thereof, can make various changes and modifications to adapt the invention to various uses and conditions. As a result, the invention is not limited by the illustrative example(s) set forth hereinbelow, but rather defined by the claims appended hereto.

Example 1—Methods

Patient Selection/Inclusion Criteria.

A subject was eligible for inclusion in this study if all of the following criteria applied:

1. Male or non-lactating, non-pregnant females aged 18-55 years, inclusive.

2. Female subjects were eligible for participation in the study if they were of
   a. non-childbearing potential (i.e., physiologically incapable of becoming pregnant); or,
   b. childbearing potential, had a negative pregnancy test (urine) at Screening, and at least one of the following applied or was agreed to by the subject:
   Female sterilization or sterilization of male partner; or,
   Hormonal contraception by oral route, implant, injection, vaginal ring; or,
   Any intrauterine device (IUD) with published data showing that the lowest expected failure rate is less than 1% per year; or,
   Double barrier method (2 physical barriers or 1 physical barrier plus spermicide); or,
   Any other method with published data showing that the lowest expected failure rate is less than 1% per year.

3. Physical status was within normal limits for age and consistent with observations at Screening.

4. Able to understand and comply with study procedures required and able and willing to provide written informed consent prior to any study procedures being performed.

Patient Selection/Exclusion Criteria.

A subject was not eligible for this study if any one or more of the following criteria applied:

1. History of hypersensitivity, allergy or intolerance to omeprazole or other proton pump inhibitors.

2. History of hypersensitivity, urticaria, allergy or intolerance to any NSAID (including ASA) and/or a history of NSAID-induced symptoms of asthma, rhinitis, and/or nasal polyps.

3. History of peptic ulcer disease or other acid-related GI symptoms.

4. Participation in any study of an investigational treatment in the 4 weeks before Screening or participation in another study at any time during the period of this study.

5. Presence of uncontrolled acute or chronic medical illness, such as cardiovascular or cerebrovascular disease, GI disorder, diabetes, hypertension, thyroid disorder, bleeding disorder, or infection that would endanger the subject if he/she participated in the study.

6. Gastrointestinal disorder or surgery leading to impaired drug absorption.

7. Any significant mental illness, such as schizophrenia, or bipolar disorder.

8. History of malignancy, treated or untreated, within the past 5 years, with the exception of successfully treated basal cell or squamous cell carcinoma of the skin.

9. Body mass index outside the range of 19-32 $kg/m^2$ at Screening.

10. Donation of a unit of blood or plasma within 4 weeks prior to the Screening or during the study.

11. History of HIV, or hepatitis B or C infection.

12. Positive test result for *H. pylori* at Screening.

13. Previous screen failure in this study.

14. History (in the past year) suggestive of alcohol or drug abuse or dependence, or excessive alcohol use (>2 units per day on average; e.g., >2 bottles of beer, >2 glasses of wine), or excessive alcohol use during the study.

15. Any abnormal Screening laboratory value that was clinically significant in the Investigator's opinion.

16. Ingestion of grapefruit or grapefruit juice within 10 days of dosing or during the study.

17. A significant medical event since the Screening Visit.

18. Use of any concomitant medication not approved by the Investigator during Screening or during the study.

19. Positive illicit drug screen.

Removal of Subjects from Therapy or Assessment.

Subjects were required to be withdrawn from the study if informed consent was withdrawn, if pregnancy occurred, or if study drug was discontinued. Subjects were also withdrawn at any time for any reason if the Principal Investigator determined that it would be in the best interest of the subject.

Subjects were considered withdrawn if they failed to return for visits or became lost to follow-up for any other reason. For subjects who were lost to follow-up (i.e., those subjects whose status was unclear because they failed to appear for study visits without stating an intention to withdraw), the Investigator was required to show due diligence by documenting in the source documents steps taken to contact the subject (i.e., dates of telephone calls, registered letters).

If early study withdrawal occurred for any reason, the Principal Investigator was to attempt to determine the primary reason for the withdrawal and record this information on the Study Summary eCRF. Reasonable efforts were to be made to perform all end-of-study procedures.

Study Design.

This was a single-center, open-label, randomized, 2-way crossover study in 26 healthy adults. The study consisted of two 7-day treatment periods. The first treatment period was followed by a washout period of at least 7 days.

Subjects were screened for inclusion up to 14 days before the first dose of study drug. Eligible subjects were then randomly assigned to receive the two treatments in a crossover fashion. This was an out-patient study; however, dosing administration took place at the Phase 1 unit. Additionally, on the evenings of Day −1 and Day 6, subjects reported to the Phase 1 unit and remained confined until completion of the 24-hour PK assessments on Day 1 and Day 7, respectively. Subjects received each of the treatments below in a randomized, 2-way crossover fashion (13 subjects planned per sequence).

Treatment.

Subjects received each of the following two treatments in a crossover fashion based on a randomization schedule with balanced treatment sequences. Study drug(s) in each treatment was taken once daily for 7 days. The two treatments were separated by a washout period of at least 7 days.

TABLE 2

Treatment Groups

| Treatment Code | Study Medication |
|---|---|
| A | One tablet of PA32540 (EC-ASA 325 mg and IR omeprazole 40 mg) administered 60 minutes prior to breakfast once daily for 7 consecutive days |
| B | One tablet of EC-ASA (Ecotin ®) 325 mg + one capsule EC omeprazole (Prilosec ®) 40 mg administered 60 minutes prior to breakfast once daily for 7 consecutive days |

PA32540 tablets are oval-shaped, blue-green tablets. Each PA32540 tablet contains EC-ASA 325 mg and IR omeprazole 40 mg. POZEN provided sufficient supplies of PA32540 (batch #3079494R) in bottles of 36 tablets each. PA32540 was manufactured and packaged by Patheon Pharmaceuticals, Inc.; the bottles were labeled by Fisher Clinical Services. Each bottle of PA32540 was labeled with the identity of the study medication, batch number, sponsor, protocol number, directions, storage instructions, child safety warning, and investigational drug statement. The PA32540 bottles contained desiccants, and study site staff were instructed not to remove the desiccants.

POZEN also provided sufficient supplies of the following commercially available FDA-approved products as reference therapies: EC-ASA 235 mg (Ecotrin®, batch #12081, exp. Dec. 31, 2011, GlaxoSmithKline) and EC omeprazole 40 mg (Prilosec®, batch # Z1061, exp. Nov. 30, 2011, AstraZeneca).

All study drug products were stored at 25° C. (77° F.), with excursions permitted to 15-30° C. (59-86° F.), in a secured area, free of environmental extremes, protected from light, with restricted access, and under the direct supervision of the Investigator or designated pharmacist or study site staff.

Method of Assigning Subjects to Treatment Groups.

At Screening, subjects who provided informed consent for the study and completed the Screening visits were assigned a consecutive screening number beginning with 0001. Once a subject's continued eligibility was confirmed, the subject was randomized and then given a 4-digit treatment number based on the next available number to be assigned from the study randomization scheme.

TABLE 3

Treatment Groups

| Sequence | Number of Subjects | Treatment Period 1 | Treatment Period 2 |
|---|---|---|---|
| I | 13 | A | B |
| II | 13 | B | A |

Treatment A: PA32540;
Treatment B: EC-ASA 325 mg + EC omeprazole 40 mg

Selection of Doses in the Study.

Each PA32540 tablet contains 325 mg of EC-ASA and 40 mg of IR omeprazole. As a comparison, Ecotrin® (EC-ASA 325 mg) was evaluated along with Prilosec® (EC omeprazole) 40 mg; both of these products are approved by the Food and Drug Administration (FDA). Acetylsalicylic acid 325 mg is a commonly used dose for the secondary prevention of cardiovascular events. Omeprazole is currently indicated for the short-term treatment of active gastric or duodenal ulcer, GERD, maintenance of healing of erosive esophagitis, and long-term treatment of pathological hypersecretory conditions. While omeprazole is not currently indicated for use in the reduction of NSAID-associated gastric or duodenal ulcers, the single isomer, esomeprazole has such an indication, and clinical data support the use of omeprazole for the prophylaxis of adverse GI effects due to NSAIDs, including ASA.

Timing of Doses for Each Subject.

All subjects were dosed each morning at the Phase 1 unit, according to their randomly assigned treatment. Dosing took place following an overnight fast that was to begin no later than midnight. Beverages were allowed as desired, except for two hours before and one hour after study drug administration. The tablets or capsule were to be swallowed whole with 240 ml water and were not to be broken, crushed, chewed, or opened. At least 60 minutes after study drug administration, subjects were served a standardized breakfast. The date and clock times for dosing and the start of breakfast intake were recorded on the eCRF:

Dosing on the morning of Day 2 occurred after the final Day 1 PK blood samples were collected.

Dosing on the morning of Day 7 occurred after the pH probe was placed.

Blinding.

This was an open-label study, however, the third party that evaluated the pH data was blinded to subject treatment assignment.

Prior and Concomitant Therapy.

All concomitant therapies taken from Screening until Final Visit assessments were recorded in the subject's medical record and transcribed to the eCRF. Subjects were instructed to refrain from using any excluded medications unless absolutely necessary. During the study, no concomitant medications were permitted, unless approved by the Principal Investigator.

The following medications were not permitted within 14 days prior to the start of dosing in Treatment Period 1 and throughout the study.

Antibiotics, Pepto Bismol

Proton pump inhibitors, or gastroprotective agents such as H2-receptor antagonists, misoprostol-containing preparations, sucralfate and antacids The following medications were not permitted within 7 days prior to the start of dosing in Treatment Period 1 and throughout the study.

Agents causing gastric injury, such as NSAIDs (except acetaminophen), including salicylic acid derivatives (e.g., ASA), bisphosphonates, steroids, anticoagulants Anticholinergic agents or MAO inhibitors Treatment Compliance.

Study drug was administered at the Phase 1 unit under supervision of site staff, who conducted a mouth check to ensure that the study drug had been swallowed whole.

Screening (Days −14 to −2).

After informed consent was obtained, subjects underwent assessments to determine eligibility for study participation. Screening assessments consisted of a review of inclusion/exclusion criteria, medical history, medication history, electrocardiogram (ECG), physical examination including vitals signs, and clinical laboratory tests (hematology, chemistry and urinalysis).

Screening also included the following tests for which the subjects had to test negative in order to participate in the study: Urine drug screen (including ethanol), *H. pylori* 13C-urea breath test, and for women, a urine pregnancy test.

Also prior to Day 1 of Treatment Period 1, all subjects underwent testing to locate their lower esophageal sphincter (LES). The position of the distance of the electrode from the nostrils was recorded on a worksheet to facilitate the 24-hour gastric pH assessments required during the study.

Subjects who continued to meet enrollment requirements were instructed to abstain from excessive alcohol consumption (>2 units alcohol on average per day; for example, >2 bottles of beer, >2 glasses of wine) during the study and to refrain from using any excluded medications unless absolutely necessary. No grapefruit or grapefruit juice was to be ingested within the 10 days prior to the first dosing in Treatment Period 1 and until after completion of Treatment Period 2. Subjects were instructed not to start any new physical training activities or increase the intensity of their usual physical training during the study.

Day −1.

Qualified subjects returned to the Phase 1 unit on the evening of Day −1. The following assessments were conducted:

Review of inclusion and exclusion criteria

Assessment of whether any serious adverse events (SAEs) had occurred

Vital signs (blood pressure, heart rate)

Urine drug screen (including ethanol)

Urine pregnancy test for all female subjects

Review of prior/concomitant medication

Subjects who continued to meet enrollment requirements, remained confined to the Phase 1 unit.

All Treatment Days (Days 1-7).

Study drug was administered in the clinic with 240 mL of water after an overnight fast that began no later than midnight. Beverages were allowed as desired except for two hours before and one hour after study drug administration on Days 1 through 7. The tablet or capsule was to be swallowed whole, and was not to be crushed, chewed, or opened. A mouth check was performed by the clinic staff to ensure that the study drug(s) had been completely swallowed. A standardized breakfast was served to each subject at least 60 minutes following study drug administration. The date and clock time of each dosing and the start time of each breakfast were recorded on the eCRF. On each treatment day, subjects were questioned about any adverse events (AEs) that may have occurred and about the use of any concomitant medications.

Day 1.

On Day 1 of Treatment Period 1 only, eligible subjects were randomized to their treatment sequence. A pre-dose blood sample was collected. Following study drug administration, sequential blood samples were obtained for PK assessments of omeprazole and salicylic acid/acetylsalicylic acid at approximately 10, 20, 30 and 45 minutes and 1, 1.5, 2, 3, 3.5, 4, 4.5, 5, 6, 7, 8, 9, 10, 11, 12, 14, 16, 20 and 24 hours post-dose. The date and clock times for each blood sampling were recorded on the eCRF.

Study drug was administered to each subject at least 60 minutes prior to being served a standardized breakfast. Subjects also received other food and beverages as appropriate during their time in the clinic.

Day 2.

In the morning of Day 2, prior to dosing, the final (24-hour post-dose) Day 1 PK blood samples were drawn. Study drug was administered to each subject at least 60 minutes prior to being served a standardized breakfast. After breakfast, subjects were discharged from the Phase 1 unit and instructed to return for dosing the next morning.

Day 3 and Day 4.

Subjects reported to the clinic in the morning of Days 3 and 4 for their assigned study treatment, which was administered in the clinic at least 60 minutes prior to a standardized breakfast. After breakfast, subjects were discharged from the Phase 1 unit and instructed to return for dosing the next morning.

Day 5.

Subjects reported to the clinic on the morning of Day 5, and remained confined through completion of the 12-hour post-dose PK blood sampling time, at which time they were discharged from the unit and instructed to return for dosing the next morning. Blood was drawn pre-dose and at approximately 10, 20, 30 and 45 minutes and 1, 1.5, 2, 3, 4, 5, 6, 7, 8, 9, 10, and 12 hours post-dose for PK assessments of omeprazole. The date and clock times for each blood sampling were recorded on the eCRF.

The subjects also underwent the following pre-dose assessments:

Vital signs (blood pressure, heart rate)
Urine drug screen (including ethanol)
Urine pregnancy test for all female subjects Subjects were administered their assigned study treatment at least 60 minutes prior to receiving a standardized breakfast. Subjects also received food and beverages as appropriate during their time in the clinic.

Day 6.

Subjects reported to the clinic on the morning of Day 6, and were administered their assigned study treatment at least 60 minutes prior to a standardized breakfast. After breakfast, subjects were discharged from the Phase 1 unit and instructed to return that same evening (Day 6), at which time they remained confined to the Phase 1 unit until completion of the PK and pH assessments on Day 8.

The subjects underwent the following assessments on the evening of Day 6:

Vital signs (blood pressure, heart rate)
Urine drug screen (including ethanol)

Day 7.

Following an overnight fast and prior to receiving the Day 7 dose of study drug, the pH probe was placed to monitor intragastric pH for a period of 24 hours. In addition, a pre-dose blood sample was collected. Following study drug administration, sequential blood samples were obtained for PK assessments of omeprazole and salicylic acid/acetyl salicylic acid at approximately 10, 20, 30 and 45 minutes and 1, 1.5, 2, 3, 3.5, 4, 4.5, 5, 6, 7, 8, 9, 10, 11, 12, 14, 16, 20 and 24 hours post-dose. The date and clock times for each blood sampling were recorded on the eCRF.

Study drug was administered to each subject at least 60 minutes prior to the standardized breakfast. Subjects also received food and beverages as appropriate during their time in the clinic. The date and start and stop clock times of each meal were recorded on the eCRF.

Day 8.

In the morning of Day 8, the final (24-hour post-dose) Day 7 PK blood samples were drawn and the pH probe carefully removed. Subjects also underwent assessments for AEs and concomitant medications. After the Day 8 study procedures were completed for Treatment Period 1, the subjects were discharged from the Phase 1 unit and reminded of the timing for the next treatment period.

For Treatment Period 2, the procedures described for Day −1 and Days 1-8 were repeated.

Washout Period.

Subjects underwent a washout period from study drug of at least 7 days between treatments. The purpose of the washout period was to dissipate all effects of the study medication prior to the beginning of the next treatment cycle. Information regarding AEs that may have occurred during this period and the use of concomitant medications were collected and documented on the eCRFs.

Final Visit.

Upon completion of the Treatment Period 2 and prior to discharge from the Phase 1 unit, the following procedures were performed: vital signs, blood draw for clinical laboratory analyses, urine collection for urinalysis, and AE and concomitant medications assessments. These procedures were also performed for any subject who discontinued early from the study.

Intragastric pH Measurement.

The pharmacodynamic assessment evaluated in this study was 24-hour intragastrci pH. The 24-hour pH assessments were performed on Day 7 using a Sandhill ZepHr pH data logger (Sandhill Scientific), which measured the difference in potential between the recording and reference electrodes in the tip of the probe, and stored this value every couple of seconds. A 2-point calibration of the electrode was made prior to the 24-hour pH assessments, using standard pH 7.00 (+/−0.05) and pH 4.00 (+/−0.05) buffers. The distance of the electrode from the nostrils was recorded on a worksheet when the LES was located during Screening, and this distance was used to accurately place the probe on Day 7 for the 24-hour pH assessments.

Following placement of the pH probe, subjects were instructed not to lie down during the day at the Phase 1 unit and to go to bed for the evening at approximately 22:00. Subjects were asked the time they went to bed to try to get to sleep and the time they got up in the morning to start their daily activities. These times were recorded on the eCRF. At the end of the pH assessments on the morning of Day 8, the pH probe was carefully removed.

Any subject who was a current smoker was asked not to deviate from their normal daily cigarette usage during the pH monitoring.

The pH data was provided to a third party who was blinded to subject treatment assignment. The third party evaluated the data to determine the validity of the pH recordings based on the following established criteria: at least 20 hours of valid pH data within a pre-specified reference range, no technical failures of the pH recording, and less than one continuous hour with pH data outside the reference range.

Evaluation of Pharmacokinetics.

Blood samples were collected for PK assessments on Days 1, 5, and 7. On Days 1 and 7, 24-hour PK sampling was performed. On Day 5, 12-hour PK sampling was performed. The date and clock times for each blood sampling were recorded on the eCRF.

Collection of Samples.

Samples for analysis of acetylsalicylic acid, salicylic acid, and omeprazole were collected as noted below. After each treatment period, all collected samples were shipped frozen overnight to the bioanalytical laboratory, PPD Development (Richmond, Va.). A detailed sample inventory sheet including subject treatment number, dates and times of collection, treatment period and scheduled time point for each sample and for each subject accompanied each shipment. A phone call (or facsimile) providing shipping information for tracking of shipments was made to the analytical laboratory just prior to shipment.

Samples for Acetylsalicylic Acid and Salicylic Acid.

On Days 1 and 7, blood samples were collected pre-dose and at approximately 10, 20, 30 and 45 minutes and 1, 1.5, 2, 3, 3.5, 4, 4.5, 5, 6, 7, 8, 9, 10, 11, 12, 14, 16, 20 and 24 hours post-dose for PK assessments of acetylsalicylic acid and salicylic acid.

The blood samples (1 sample of 2 mL each) for acetylsalicylic acid and salicylic acid analysis were collected in tubes containing sodium fluoride and potassium oxalate. Each sample-collection tube was pre-chilled (refrigerated at approximately 2° C. to 8° C. or on ice) prior to sample collection and filled completely to ensure sufficient sample volume for the required test. Immediately after the sample was drawn, the tube was gently inverted 8 to 10 times and then submerged (in an upright position) in an ice water mixture to the height of the blood in the tube. Samples were stored on ice for a maximum of 30 minutes prior to completing the processing procedure. Each sample was centrifuged at 2000 to 3000 rpm for 10 to 15 minutes at 2° C. to 8° C., then all available plasma supernatant was transferred to a polypropylene sample storage tube, capped and frozen at −70° C. or lower. Samples were kept in the frozen state (−70° C. or lower) until analysis.

Samples for Omeprazole.

On Days 1 and 7, blood samples were collected pre-dose and at approximately 10, 20, 30 and 45 minutes and 1, 1.5, 2, 3, 3.5, 4, 4.5, 5, 6, 7, 8, 9, 10, 11, 12, 14, 16, 20 and 24 hours post-dose for PK assessments of omeprazole. Also, on Day 5, blood samples were collected pre-dose and at approximately 10, 20, 30 and 45 minutes and 1, 1.5, 2, 3, 4, 5, 6, 7, 8, 9, 10, and 12 hours post-dose for PK assessment of omeprazole.

The blood sample (2 mL) for omeprazole analysis was collected in a sodium heparin tube, inverted several times and centrifuged within 30 minutes of sample draw for 15 minutes at 3000 rpm (approximately 1800×g) in a refrigerated centrifuge maintained at approximately 4° C. All available plasma supernatant was withdrawn from the precipitated blood fraction, placed in an appropriate shipment and storage tube, and frozen at −20° C. or lower within 30 minutes of centrifugation. Samples were kept in the frozen state (−20° C.) until analysis.

Analysis of Acetylsalicylic Acid and Salicylic Acid in Plasma.

Concentrations of acetylsalicylic acid and salicylic acid in human plasma were determined using a validated LC/MS/MS method developed at PPD Development, Richmond, Va. The assay method and validation results are described in the assay validation report for the plasma samples as found in Bioanalytical Report—Acetylsalicylic Acid and Salicylic Acid.

A 50-µL sample aliquot was combined with an aliquot of the internal standard solution containing the deuterated analogs of acetylsalicylic acid and salicylic acid. The analyte and the internal standard were isolated through protein precipitation using acetonitrile. No automated sample preparation procedure was used. The extracted samples were injected onto the LC/MS/MS system for chromatographic separation and detection using a Sciex API 4000 instrument. Chromatographic retention of the analytes and internal standards were obtained on a Betasil Silica 100 analytical column (3.0×100 mm, 5-µm particle size) using a gradient separation. The composition of mobile phase A was 2 mM ammonium formate (pH 5), in 90:10 acetonitrile:water (v/v) and the composition of mobile phase B was 2 mM ammonium formate (pH 5), in 40:60 acetonitrile:water (v/v). The mobile phase flow rate was 0.40 mL/minute. The analytes were detected by MS/MS with negative electrospray ionization in the mode of multiple reaction monitoring (MRM), with ions monitored for acetylsalicylic acid (m/z 179.0→93.0), salicylic acid (m/z 136.9→93.0), and the deuterated analogs 2-acetoxybenzoic-3,4,5,6-d4 acid (m/z 183.1→97.1) and 2-hydroxybenzoic-3,4,5,6-d4 acid (m/z 141.1→97.1).

Quantification was by analyte to internal standard peak area ratio. The linear range of the method was 0.02 to 10 µg/mL for acetylsalicylic acid in human plasma with a lower limit of quantitation (LLOQ) of 0.02 µg/mL, and 0.10 to 50 µg/mL for salicylic acid in human plasma with an LLOQ of 0.10 µg/mL. The assay was validated in terms of specificity, precision, accuracy, and sample stability, as shown in the assay method validation report found in Bioanalytical Report—Acetylsalicylic Acid and Salicylic Acid.

Analysis of Omeprazole in Plasma.

Concentrations of omeprazole in human plasma were determined using a validated LC/MS/MS method developed by PPD Development, Richmond, Va. The assay method and validation results are described in the assay validation report for the plasma samples found in Bioanalytical Report—Omeprazole.

A 100-µL sample aliquot was combined with an aliquot of an internal standard solution containing the deuterated analog of omeprazole. The analytes were isolated by solid phase extraction using a Phenomenex Strata-X 10 mg, 96-well SPE plate and eluted with 400 µL of 0.1% ammonium hydroxide in acetonitrile. Sample extraction steps were controlled and automated using a Tomtec Quadra 96 Model 320 Liquid Handling Workstation. The final extract was injected onto an LC/MS/MS system for chromatographic separation and detection using a Micromass Quattro Micro instrument. Chromatographic retention and separation of the analytes was obtained on a Betasil Silica-100 analytical column (3.0×100 mm, 5-µm particle size) using a gradient HPLC system. The composition of mobile phase A was acetonitrile:water:formic acid (88:12:0.1 v/v/v) and the composition of mobile phase B was 0.1% formic acid. The mobile phase flow rate was 0.5 mL/minute. The analytes were detected by MS/MS with positive electrospray ionization in the mode of multiple reaction monitoring (MRM), with ions monitored for omeprazole (m/z 346.0→198.0) and deuterated omeprazole (m/z 349.0→198.0).

Quantification was by analyte to internal standard peak area ratio. The linear range of quantitation was 1 to 1000 ng/mL in human plasma, with an LLOQ of 1 ng/mL. The assay was validated in terms of specificity, precision, accuracy, and sample stability, as shown in the assay method validation report found in Bioanalytical Report—Omeprazole.

Analysis of Acetylsalicylic Acid and Salicylic Acid in Plasma.

The bioanalytical report for the analysis of acetylsalicylic acid and salicylic acid in plasma samples obtained from this study is provided in Bioanalytical Report—Acetylsalicylic Acid and Salicylic Acid.

For acetylsalicylic acid, a set of 8 calibration standards ranging from 0.02 to 10.0 µg/mL and Quality Control (QC) samples at 5 different concentrations (0.05, 0.125, 0.450, 1.50, and 7.50 µg/mL) of acetylsalicylic acid were prepared. For salicylic acid, a set of 8 calibration standards ranging from 0.10 to 50.0 µg/mL and QC samples at 5 different concentrations (0.250, 0.625, 2.25, 7.50, and 37.50 μg/mL) of salicylic acid were prepared. Between-batch precision and accuracy for analysis of the QC samples were determined from batch analyses of clinical samples in this study.

The inter-assay coefficients of variation of the QCs for the acetylsalicylic acid runs ranged from 4.7% to 9.0%, with mean percent differences from theoretical ranging from −3.3% to 1.3%. The inter-assay coefficients of variation of the QCs for the salicylic acid runs ranged from 3.1% to 4.0%, with mean percent differences from theoretical ranging from −1.8% to −1.0%. The differences of back-calculated calibration curve values from nominal values ranged from −1.6% to 1.0% for acetylsalicylic acid and ranged from −1.0% to 0.8% for salicylic acid.

To demonstrate reproducible quantification of incurred subject samples, at least 5% of the study samples were re-assayed as incurred sample repeats. Incurred sample repeats were considered acceptable if the original and re-assay values from two-thirds of the repeated samples had a relative percent difference of ≤20%. The results of the incurred sample repeats met the acceptance criteria.

Analysis of Omeprazole in Plasma.

For omeprazole, a set of 8 calibration standards ranging from 1.00 to 1000 ng/mL and QC samples at 5 different concentrations (2.6, 8.0, 30.0, 130, and 750 ng/mL) of the analyte were prepared. Between-batch precision and accuracy for analysis of the QC samples were determined from batch analyses of clinical samples in this study.

The inter-assay coefficients of variation of the QCs for the omeprazole runs ranged from 2.5% to 10.2%, with mean percent differences from theoretical ranging from −0.1% to 1.4%. The differences of back-calculated calibration curve values from nominal values ranged from −1.0% to 1.2%. For analytical runs which contained diluted subject samples due to quantitation above the calibration range, the appropriate level quality control was diluted and analyzed in a similar manner to validate the dilution of study samples. For diluted quality control samples, the inter-assay coefficients of variation of the QCs for the omeprazole runs ranged from 0.8% to 5.6%, with mean percent differences from theoretical ranging from −1.1% to 1.0%.

To demonstrate reproducible quantitation of incurred subject samples, at least 5% of the study samples were reassayed as incurred sample repeats. Incurred sample repeats were considered acceptable if the original and reassay values from two-thirds of the repeated samples had a relative percent difference of ≤20%. The results of the incurred sample repeats met the acceptance criteria.

Medical History and Physical Examination.

A review of past and current medical conditions and a physical examination, including height and weight, were performed by the Investigator or qualified member of the study staff at Screening. Recent drug (licit and illicit) use was reviewed, as well as a life history of drug allergies and intolerances.

Vital Signs and 12-Lead Electrocardiogram.

At Screening, heart rate and systolic and diastolic blood pressure were measured and recorded after the subject had been sitting for at least 5 minutes. In both treatment periods, vital signs were measured pre-dose on Day 5 and at check-in to the Phase 1 unit on the evening of Day 6. Vital signs were also measured at Final Visit upon completion of all study procedures (or study discontinuation, if applicable). Also at Screening, a 12-lead ECG was performed.

Clinical Laboratory Tests.

At Screening and Final Visit (or study discontinuation), samples were collected for the following laboratory assessments:
Creatinine, alanine transaminase, aspartate transaminase, alkaline phosphatase, total bilirubin, blood urea nitrogen;
Complete blood count including hematocrit;
Urinalysis including microscopic blood, protein and glucose.

The Investigator was responsible for assessing the clinical significance of all abnormal laboratory values and providing comments on the eCRF. All abnormal laboratory tests that were judged to be at least possibly drug-related, or clinically relevant abnormal laboratory tests of uncertain causality, were repeated. Any abnormal values were followed at the discretion of the Investigator. In some cases, significant changes within the range-of-normal required similar judgment. Abnormal laboratory values were not listed on the adverse event eCRF unless clinical signs or symptoms were present.

A $^{13}$C-urea breath test for *H. pylori* was performed at Screening. A subject with a positive test result was not eligible for randomization into the study.

Urine drug screens for amphetamines, barbiturates, benzodiazepines, *cannabis*, cocaine, opiates, and ethanol were performed at Screening, and for each treatment period on Day −1, Day 5 (pre-dose), and in the evening of Day 6 at check-in to the clinic. A positive test result excluded the subject from (further) participation in the study.

All female subjects had a pregnancy test at Screening, and for each treatment period on Day −1 and Day 5 (pre-dose). A positive test result excluded the subject from (further) participation in the study.

Adverse Events.

An AE (or adverse experience) was defined as any untoward medical occurrence in a subject or clinical investigation subject administered a pharmaceutical product and which does not necessarily have a causal relationship with this treatment.

All AEs occurring from the start of study medication administration through the final follow-up visit were recorded on the adverse event eCRF with the following information:
the severity grade (mild, moderate, severe);
its relationship to the study medication(s) (not related, unlikely, possibly, or unrelated);
its duration (start and end dates or if continuing at final exam);
whether it constitutes a serious AE (SAE).

The occurrence of AEs was sought by non-directive questioning of the subject at each visit during the study. Adverse events were also detected when they were volunteered by the subject during or between visits or through physical examination, laboratory tests or other assessments. Medical conditions or diseases present before starting study medication were considered AEs only if they worsened after starting study medication. Abnormal laboratory values or test results constituted AEs only if they induced clinical signs or symptoms, were considered clinically significant or required therapy. Adverse event collection commenced upon a subject taking study medication.

All AEs were treated appropriately. The action taken to treat the AE was recorded on the adverse event eCRF. A detected AE was followed until its resolution or until it was judged to be permanent. Assessment was made at each visit (or more frequently, if necessary) of any changes in severity, relationship to the study medication, the interventions required to treat it, and the outcome.

Information about common side effects already known about the investigational drug were presented in the Investigator Brochure (IB) or were communicated between IB updates in the form of an Investigational New Drug Safety Letter (Investigator Notifications). This information was included in the subject informed consent and was discussed with the subject during the study as needed.

Serious Adverse Events.

An SAE was defined as an event that, in the view of either the Investigator or the sponsor, was fatal or life-threatening; resulted in persistent or significant disability or incapacity; constituted a congenital anomaly or birth defect; required inpatient hospitalization or prolongation of existing hospitalization, unless hospitalization was for:

- routine treatment or monitoring of the studied indication, not associated with any deterioration in condition;
- elective or pre-planned treatment for a pre-existing condition that was unrelated to the indication under study and had not worsened since the start of study medication;
- treatment on an emergency outpatient basis for an event not fulfilling any of the definitions of a SAE given above and not resulting in hospital admission;
- social reasons and respite care in the absence of any deterioration in the subject's general condition;
- was medically significant, i.e., defined as an event that jeopardized the subject or may have required medical or surgical intervention to prevent one of the outcomes listed above.

To ensure subject safety, every SAE, regardless of suspected causality, occurring after the subject signed informed consent and until 4 weeks after the subject had stopped study participation was reported to the study Medical Monitor within 24 hours of learning of its occurrence. If the SAE was not previously documented in the IB or Package Insert (new occurrence) and was thought to be related to the POZEN study medication, the study Medical Monitor could have urgently required further information from the Investigator for Health Authority reporting. The Investigator was responsible for promptly notifying the IRB of all SAEs, including any significant follow-up information.

Data Quality Assurance.

All clinical work conducted under this protocol was subject to GCP and International Conference on Harmonization (ICH) guidelines. The study was subject to inspection by regulatory authorities (e.g., FDA) and POZEN or its designee(s). The purpose of these efforts was to ensure that the trial was conducted and data were collected, documented, and reported in compliance with the protocol, GCP, and all applicable regulatory requirements.

After receiving training in the electronic data capture system, designated study site staff entered the data required by the protocol into the eCRFs. POZEN or its designees reviewed source documents at the study site to verify compliance with the protocol and regulatory guidelines and to assure accuracy of the data. As a result of the data review process, corrections or changes to eCRFs were required. Any such changes were made on the eCRF. A complete audit trail of all changes, the individual making the changes and reasons for the changes was maintained. The Investigator certified the completeness and accuracy of the data prior to database lock.

Laboratory data required by the protocol was electronically transferred from the central clinical laboratory to POZEN, or their designee. Concomitant medications entered into the database were coded using the World Health Organization Drug reference list, which uses the ATC code (Anatomical Therapeutic Chemical classification system). Adverse Events were coded using MedDRA (Medical Dictionary for Regulatory Activities, Version 12.1) terminology for system organ class (SOC) and preferred term.

Statistical and Analytical Plans.

Data were summarized by reporting the frequency and percentage of subjects in each category for categorical and ordinal measures, and means, standard deviations (SD) or standard errors (SE), medians, and ranges for continuous measures. Unless otherwise specified, statistical significance was tested at the 5% level. All analyses were performed using SAS Version 9.1 or higher.

Intent-To-Treat (ITT) Population.

The ITT population included all randomized subjects who had valid pH data for at least 1 treatment period. A subject was considered as having valid pH data for each treatment period if the subject received all study doses per protocol and had at least 20 hours of valid pH data determined by the clinical investigator, had no technical failures of the pH recording and did not have 1 continuous hour or more with pH data outside the reference range. The ITT population was used for the secondary analysis of pharmacodynamic endpoint.

Per-Protocol.

The per-protocol population included all ITT subjects who had valid pH data for the two treatment periods and did not violate the protocol in any major way that would have impacted the evaluation of pharmacodynamic endpoint. The per-protocol population was used for the primary analysis of pharmacodynamic endpoint.

Pharmacokinetic (PK) Population.

The PK population included all randomized subjects who received all study doses for at least one treatment period and had adequate blood sampling to assess the PK parameters of omeprazole and salicylic acid. The PK population was used in the statistical analyses of PK parameters.

Safety Population.

The safety population included any subject who received at least one dose of study medication. The summary of safety data and baseline characteristics were performed based on the safety population.

Pharmacodynamic Endpoint (Primary).

The primary pharmacodynamic endpoint (percent time intragastric pH >4.0 on Day 7) was calculated for each subject for each treatment period, and was analyzed by analysis of variance (ANOVA). The ANOVA model included sequence, period, and treatment as fixed effects, and subject within sequence as a random effect. The least squares means (LSM) for each treatment, the difference of LSM between treatments and associated 95% confidence intervals (CIs) were calculated. Mean pH data over 24-hours on Day 7 was plotted by treatment. Both the per-protocol and ITT populations were used for the pharmacodynamic analysis. The per-protocol population was used for the primary analysis. In addition, the percent time intragastric pH >3.0 and >5.0 on Day 7 was listed and summarized by treatment.

Pharmacodynamic Endpoints (Exploratory).

The exploratory endpoint (time to intragastric pH>4 on Day 7) was analyzed using the same methods as for the primary endpoint.

Analysis of Pharmacokinetics.

Plasma concentration vs. time data for each analyte (omeprazole, acetylsalicylic acid and salicylic acid) were listed and summarized by treatment and study day using descriptive statistics, which included mean, standard deviation (SD), % coefficient of variation (CV), median, minimum and maximum.

Plasma concentrations below the LLOQ (i.e., 1 ng/mL for omeprazole, 0.02 µg/mL for acetylsalicylic acid, and 0.1 µg/mL for salicylic acid) were treated as a zero value when calculating summary (or descriptive) statistics. The mean/median value at a time point with one or more concentrations below the LLOQ (i.e., below the quantitation limit [BQL] value) was reported unless the resulting mean/median values were below the LLOQ, in which case the value was assigned as BQL. A high proportion of BQL values would affect the SD estimate; thus, if more than 30% of values were imputed, SD was not displayed.

Pharmacokinetic parameter estimates for each of the three analytes were calculated with non-compartmental methods using WinNonlin Professional software version 5.2.1 (Pharsight, Inc. Mountain View, Calif.).

For PK analysis, plasma concentrations below the LLOQ in individual profiles of each analyte were handled as follows. If the value occurred in a profile during the absorptive phase, i.e., before the maximum concentration in a profile was observed, it was assigned a value of zero. Any one or two BQL values that occurred between measurable concentrations were excluded from analysis. If three values below the LLOQ occurred in succession post peak time (or during the terminal phase), the profile was determined to have terminated at the last time point with measurable analyte concentration.

Pharmacokinetic parameters were calculated for each analyte using the actual sampling times. The actual plasma sampling times were determined for each sample collected based on the elapsed time from dosing time on each PK assessment day.

The PK parameters calculated for omeprazole (on Days 1, 5, and 7) and for acetylsalicylic acid and salicylic acid (on Days 1 and 7) included the following:

Maximum plasma concentration ($C_{max}$)

Time to maximum plasma concentration ($t_{max}$)

Area under the plasma concentration-time curve from time zero (time of dosing) to the last time point with measurable drug concentration ($AUC_{0-t}$)

Area under the plasma concentration-time curve from time zero to 12 hours post-dose ($AUC_{0-12}$), for omeprazole only Area under the plasma concentration-time curve from time zero to 24 hours post-dose ($AUC_{0-24}$)

Plasma half-life ($t_{1/2}$)

In addition, area under the plasma concentration-time curve from time zero to infinite time ($AUC_{0-inf}$) and percentage of the extrapolated area under the plasma concentration-time curve (% $AUC_{ext}$) for each analyte on Day 1 were calculated.

The plasma PK parameters for each analyte were listed and summarized by treatment and study day using descriptive statistics. Descriptive statistics, including mean, SD, % CV, median, minimum and maximum, were calculated for all PK parameters by treatment and study day. In addition, geometric means and associated 95% confidence intervals (CI) were calculated for all PK parameters, except $t_{max}$ and % $AUC_{ext}$.

Statistical analysis was performed using ANOVA to compare the natural logarithmic (ln)-transformed PK parameters of AUCs and $C_{max}$ of omeprazole, salicylic acid and acetylsalicylic acid between treatments on Day 1, Day 5 (omeprazole only), and Day 7. The ANOVA model included sequence, period, and treatment as fixed effects, and subject within sequence as a random effect. The geometric LSM ratios between treatments (i.e., Treatment A vs. Treatment B) for each day and the corresponding 90% CIs were calculated for AUCs and $C_{max}$.

In addition, an ANOVA model, including day as fixed effect and subject as a random effect, was used to determine the point estimate and 90% CI of the ratios between days (i.e., Day 7 vs. Day 1, Day 5 vs. Day 1 and Day 7 vs. Day 5) for $C_{max}$, $AUC_{0-12}$ and $AUC_{0-24}$ of omeprazole within each treatment, and the Day 7 to Day 1 ratios for $C_{max}$ and $AUC_{0-24}$ of salicylic acid within each treatment. The ln-transformed $C_{max}$ and AUCs were used for these analyses.

Analysis of Safety.

Adverse events were coded into a MedDRA (Medical Dictionary for Regulatory Activities) (version 12.1) term, and summarized for each treatment by system organ class (SOC) and preferred term.

All AEs that occurred from the start of study drug administration through the Final Visit were considered AEs. The number and percent of subjects reporting an AE were tabulated by SOC, preferred term, and treatment. The incidence of AEs by maximum severity and the incidence of treatment-related AEs were summarized by SOC, preferred term, and treatment. For summaries by severity of event, the most severe occurrence for a particular preferred term was used for a given subject. A treatment-related AE was defined as an event with a "Possibly Related" or "Related" relationship to study drug.

Laboratory test results for blood chemistry, hematology, and urinalysis were listed separately by subject and summarized by study visit. Any results outside the normal reference ranges were flagged as low or high on the listings. Vital signs were listed by subject and summarized by study visit.

Determination of Sample Size.

According to a previous intragastric pH study, a sample size of 26 subjects was considered adequate to evaluate the pharmacodynamic endpoint of percent time pH >4.0 between PA32540 and EC-ASA 325 mg+EC omeprazole 40 mg after 7 consecutive once-daily doses.

Changes in the Conduct of the Study or Planned Analyses.

There was one protocol amendment, dated 23 Mar. 2011. The purpose of the amendment was to change the PK assessment blood samples for omeprazole, acetylsalicylic acid, and salicylic acid from 3 mL to 2 mL in Section 12 (Pharmacokinetics). Although acetylsalicylic acid was described in this section of the protocol, the sample collection times and PK analysis were not described. In this study, in addition to blood samples being collected on Day 1 and Day 7 for assessment of omeprazole and salicylic acid PK, an additional sample was collected for analysis of acetylsalicylic acid. This sample was collected pre-dose and at the same specified post-dose times that blood was collected for the omeprazole and salicylic acid assessments.

The amendment also added a pre-dose Day 5 requirement for urine drug screen and changed the post-dose urine pregnancy test from Day 6 to pre-dose Day 5. Additionally, the amendment clarified when meal times should be recorded and updated Laboratory Assessments to match the Visit Schedule and Assessment Table. The study was conducted as described in the protocol, however there were some changes as noted below.

The protocol mentioned a beverage restriction ("Beverages are allowed as desired except for two hours before each study drug administration until mealtime on Days 2 through 7.") in the Synopsis and in Sections 8.1 and 8.1.3.1 for treatment Days 2-7. This was a typographical error and should have been noted to refer to all treatment days (i.e., Days 1-7). At the time the study was conducted, this beverage restriction was enforced on Treatment Days 1-7.

The protocol also mentioned in error that the dosage form of Prilosec® 40 mg as used in this protocol was a tablet. Prilosec® 40 mg (AstraZeneca) is a capsule, and this is what was evaluated in the protocol.

On Day 5, the investigative site collected in error blood samples (2×2 mL samples on 13 patients, one for ASA and one for salicylic acid). These samples were analyzed, and the data were included in PK data analysis, but not summarized.

A post-hoc analysis was performed using ANOVA to compare the ln-transformed PK parameters AUCs and $C_{max}$ of acetylsalicylic acid between treatments on Day 1 and Day 7. A post-hoc analysis was also performed using ANOVA to compare the time to reach intragastric pH>4 on Day 7.

Example 2—Results

The protective effects of low-dose acetylsalicylic acid (≤325 mg/day) against serious cardiovascular and cerebrovascular events are well established (Antithrombotic Trialists' Collaboration 2002). Despite its proven vascular benefits, acetylsalicylic acid (ASA) can be associated with considerable upper gastrointestinal (UGI) damage that is not reduced with the use of either enteric-coated (EC) or buffered ASA (Kelly 1996; De Abajo 2001). The current expert consensus document by the leading cardiology and gastroenterology organizations in the United States recommends proton pump inhibitors (PPIs) as the preferred agents for the treatment and prophylaxis of ASA-associated gastrointestinal (GI) injury in patients who are at risk for GI adverse events (Bhatt 2008; Abraham 2010).

POZEN is developing a safer acetylsalicylic acid (ASA) product (PA) for the secondary prevention of cardiovascular events in patients at risk for developing ASA-associated ulcers. PA is a proprietary, multi-layered, oral combination tablet composed of an enteric-coated acetylsalicylic acid (EC-ASA) core surrounded by an immediate-release (IR) omeprazole layer. PA32540 consists of EC-ASA 325 mg and IR omeprazole 40 mg. The PA32540 tablet is designed to minimize ASA-related GI toxicity while delivering a bioequivalent dose of ASA. Placement of the IR omeprazole in the outer layer makes it available for instantaneous dissolution, thus allowing the therapeutic activity (raising intragastric pH) of omeprazole to start rapidly after ingestion and prior to the dissolution of the EC-ASA component that dissolves at pH of >5.5.

Data from three, 28-day, Phase I proof-of-concept studies (PA325-101, PA325-102, and PA325-106) demonstrated the improved UGI safety profile of POZEN's PA products using Lanza scores (Lanza 1988, Fort 2008, Gurbel 2008). A significantly lower incidence of UGI mucosal damage was associated with PA32520 (EC-ASA 325 mg and IR omeprazole 20 mg) and PA32540 (EC-ASA 325 mg and IR omeprazole 40 mg) compared to 325 mg of a commercially available EC-ASA product; a nonsignificant, numerical difference in favor of PA32520 was also observed between PA32520 and 81 mg of a commercially available EC-ASA product. There were no serious adverse events in these studies, and adverse events were mostly mild.

This study was designed to provide data on the antisecretory effect of PA32540 vs. EC-ASA (Ecotrin®) 325 mg+EC omeprazole (Prilosec®) 40 mg, as measured by percent time intragastric pH >4. In addition, the PK of omeprazole and salicylic acid following administration of PA32540 and EC-ASA 325 mg+EC omeprazole 40 mg were assessed. A previous PK study (PA32540-104) demonstrated that both PA32540 and the ASA component of PA32540 (without omeprazole) were bioequivalent to a commercially available EC-ASA 325 mg tablet (Ecotrin®), with respect to the pharmacokinetics of salicylic acid (the active moiety of ASA) (Alberts 2009).

Disposition of Subjects.

Subject enrollment and disposition data are displayed in Table 4. The study lasted 21 days and a total of 26 subjects were randomized and completed the study. Two subjects (1015 and 1023) were not included in the per-protocol population—subject 1015 due to invalid recording of pH data in Treatment Period 2 and subject 1023 due to corrupt data file with unreliable time stamping in Treatment Period 1.

TABLE 4

Subject Disposition (All Randomized Subjects)

|  | Number of Subjects (%) N = 26 |
| --- | --- |
| Subjects randomized | 26 (100) |
| Safety population | 26 (100) |
| Intent-to-treat | 26 (100) |
| Per-protocol population | 24 (92) |
| Pharmacokinetic population | 26 (100) |
| Subjects completed | 26 (100) |

Protocol Deviations.

There were no major protocol violations reported in the study. There were, however, protocol deviations relating to the urine drug screening tests, urine pregnancy tests, total volume of blood drawn on one of the PK blood sampling days, and the timing of the Final Visit clinical laboratory assessments.

On Day −1 in Treatment Period 2, no urine drug screen results were available for any subject. Likewise, there were no urine drug screen results available for subject 1013 on Day 5 of Treatment Period 1.

There were 2 protocol deviations relating to positive urine screens for ethanol. Subject 1019 had a positive urine screen for ethanol on Day −1 of Treatment Period 1 and subject 1026 had a positive urine screen for ethanol on Day 6 of Treatment Period 2. Neither subject was found to have been intoxicated by the Investigator. The Medical Officer and the Investigator reviewed the information and concluded that the positive drug screen would not affect either the pharmacodynamic or PK results of the study. Both subjects completed the study and data from these 2 subjects were included in the per-protocol, ITT, and PK analyses.

On Day 6 of Treatment Period 1, a urine pregnancy test was performed on all female study subjects. Per protocol, urine pregnancy tests were only to be performed at Screening and on Day −1 and Day 5 of each treatment period.

On Day 5 of Treatment Period 1, all subjects had 4 mL of blood drawn for PK analysis, instead of 2 mL of blood.

Due to an error at the investigative site, the final clinical laboratory tests were not collected until approximately 1 month following the final dose of study drug.

Demographic and Other Baseline Characteristics.

The demographic characteristics of the safety population at Screening are summarized in Table 5. The study population had a mean age of 29 years, and 62% of the population was female. A total of 92% of the population was Caucasian, and all subjects were non-Hispanic or non-Latino.

TABLE 5

Demographic Characteristics (Safety Population)

| | Total Subjects (N = 26) |
|---|---|
| Age (years) | |
| Mean (SD) | 29.2 (10.1) |
| Median | 26.0 |
| Range | 19-55 |
| Gender, n (%) | |
| Female | 16 (62%) |
| Male | 10 (38%) |
| Race, n (%) | |
| White | 24 (92%) |
| African American | 1 (4%) |
| Asian | 1 (4%) |
| Ethnicity, n (%) | |
| Not Hispanic or Latino | 26 (100%) |
| Height (cm) | |
| Mean (SD) | 176.73 (9.96) |
| Median | 176.53 |
| Range | 162.6-195.6 |
| Weight (kg) | |
| Mean (SD) | 77.91 (14.8) |
| Median | 76.43 |
| Range | 56.7-102.5 |
| Body Mass Index kg/m$^2$ | |
| Mean (SD) | 24.732 (2.760) |
| Median | 24.386 |
| Range | 19.77-29.82 |
| Current smoker, n (%) | 1 (4.4%) |

SD = standard deviation

Current medical conditions were present in 7 subjects (27%), the majority of which were antibiotic allergies (5 subjects). Eleven subjects (42%) had an abnormal ECG at Screening, but none of the results were considered clinically significant. A total of 4 subjects (15%) reported the use of concomitant medications, all of which were hormonal contraceptives.

Measurements of Treatment Compliance.

All study drug doses were administered under supervision by the site staff at the Phase 1 unit, and included a mouth check to ensure that study drug had been swallowed whole. The date and clock time (hours and minutes) of dosing administration were recorded in the subject eCRF. In addition, the date and clock time of the start of breakfast was recorded on the eCRF. On Day 7, the date and clock times of the start and stop of all meals was recorded on the eCFR.

Pharmacodynamic and Pharmacokinetic Evaluations/Data Sets Analyzed.

A total of 26 subjects were enrolled in the study, and all 26 completed the study. Valid intragastric pH data were available in at least one treatment period for all 26 subjects (ITT cohort), 25 subjects had valid data for Treatment A (PA32540) and 25 subjects had valid data for Treatment B (EC-ASA 325 mg+EC omeprazole 40 mg). A total of 24 subjects had valid intragastric pH data in both treatment periods, and these 24 were included in the per-protocol population, the primary pharmacodynamic analysis population. Blood samples for PK evaluation were obtained from all 26 subjects completing the study on designated study days. All 26 subjects were included in the PK population analysis set.

Pharmacodynamic Results and Tabulations of Individual Subject Data/Analysis of Intragastric pH (Primary Endpoint).

A summary of the percent time intragastric pH >4 for the per-protocol population is shown in Table 6. The mean percent time intragastric pH >4 was 50.5 for PA32540 and 57.5 for EC-ASA 325 mg+EC omeprazole 40 mg. Similar findings were observed in the ITT cohort.

TABLE 6

Summary of Percent Time Gastric pH > 4 on Day 7 (Per-protocol Population)

| | PA32540 (n = 24) | EC-ASA 325 mg + EC omeprazole 40 mg (n = 24) |
|---|---|---|
| Mean (SD) | 50.49 (18.51) | 57.49 (16.01) |
| Median | 44.95 | 55.71 |
| CV | 37 | 28 |
| Range | 27.61-99.79 | 21.05-97.18 |

The analysis of percent time intragastric pH >4 for the per-protocol and ITT populations is shown in Table 7. For the per-protocol population, treatment with PA32540 resulted in significantly less percent time intragastric pH >4 compared with EC-ASA 325 mg+EC omeprazole 40 mg (LSM difference −6.95, 95% CI (−11.46 to −2.43); P=0.004). Similar findings were observed in the ITT cohort.

TABLE 7

Analysis of Percent Time Gastric pH > 4 on Day 7

| Populations | PA32540 Least Squares Mean (SE) | EC-ASA 325 mg + EC omeprazole 40 mg | LSM Difference | 95% CI | P-value |
|---|---|---|---|---|---|
| Per-protocol (n = 24) | 50.64 (3.61) | 57.59 (3.61) | −6.95 (2.18) | −11.46, −2.43 | 0.004 |
| ITT (n = 25) | 50.59 (3.36) | 57.58 (3.36) | −6.99 (2.16) | −11.46, −2.52 | 0.004 |

The data show that intragastric pH increases more rapidly and recovers sooner with PA32540 vs. EC-ASA 325 mg+EC omeprazole 40 mg (FIG. 1).

Analysis of Intragastric pH (Exploratory Endpoint).

As shown in Table 8, treatment with PA32540 resulted in a significantly faster time to pH>4 compared with EC-ASA 325 mg+EC omeprazole 40 mg (LS mean time 0.29 hours vs. 0.60 hours, respectively; 95% CI [−0.54 to −0.08]; P=0.011).

TABLE 8

| | Time to Intragastric pH > 4 (Hour) on Day 7 | | | | |
|---|---|---|---|---|---|
| Population | PA32540 Least Squares Mean (SE) | EC-ASA 325 mg + EC omeprazole 40 mg | LSM Difference | 95% CI | P-value |
| Per-protocol) | 0.29 (0.09) | 0.60 (0.09) | −0.31 (0.11) | −0.54, −0.08 | 0.011 |
| Intent-to-treat | 0.32 (0.09) | 0.60 (0.09) | −0.29 (0.10) | −0.50, −0.07 | 0.011 |

Statistical/Analytical Issues/Adjustments for Covariates.

No adjustments for covariates were made in the analysis of these data.

Handling of Dropouts or Missing Data.

No subject discontinued from the study. Missing data were not imputed in the analyses. Only subjects with evaluable data were included in the calculation of summary statistics for parameters of interest.

Interim Analyses and Data Monitoring.

There was no interim analysis of data from this study.

Pharmacodynamic Conclusions.

PA32540 had a statistically significantly lower percent time intragastric pH >4 compared with EC-ASA 325 mg+EC omeprazole 40 mg (51% vs. 58%, respectively; P=0.004) and was consistent with the IR formulation of omeprazole:

Time to reach intragastric pH>4 was approximately 50% faster with PA32540 (17 minutes) vs. EC omeprazole 40 mg (36 minutes).

The subsequent recovery of intragastric pH was also reached sooner with PA32540.

Time to maximum intragastric pH in the first 4 hours following dosing was also achieved sooner with PA32540 (1.3 hours) compared with EC omeprazole 40 mg (1.76 hours).

Pharmacokinetics Results and Tabulations of Individual Subject Data/Plasma Drug Concentration Data/Plasma Omeprazole Concentrations.

Following administration of PA32540, omeprazole rapidly appeared in the plasma, with concentrations measurable at the first sampling time (i.e., 10 minutes post-dose) in the majority of subjects on each PK study day. Plasma omeprazole concentrations were generally measurable up to 7-8 hours after the first dose of PA32540 (Day 1), up to 8-9 hours on Day 5 and up to 9-10 hours on Day 7 following repeat daily doses of PA32540 in the majority of subjects. Except for one subject on Day 5, none of the pre-dose samples had measurable omeprazole concentrations on Day 5 or Day 7 following repeat doses of PA32540.

Following administration of EC omeprazole 40 mg (Prilosec®), plasma omeprazole concentrations were measurable starting at 20 minutes post-dose, and up to 9-10 hours after the first dose, and up to 12 hours after repeat daily doses on Day 5 and Day 7 in the majority of subjects. These observations in comparison to those observed for PA32540 (containing IR omeprazole) were expected for an EC formulation.

Mean and median plasma omeprazole concentration vs. time profiles show the differences between the IR and EC formulations of omeprazole, with the EC formulation exhibiting right-shifted curves on each PK study day.

Figure 2:
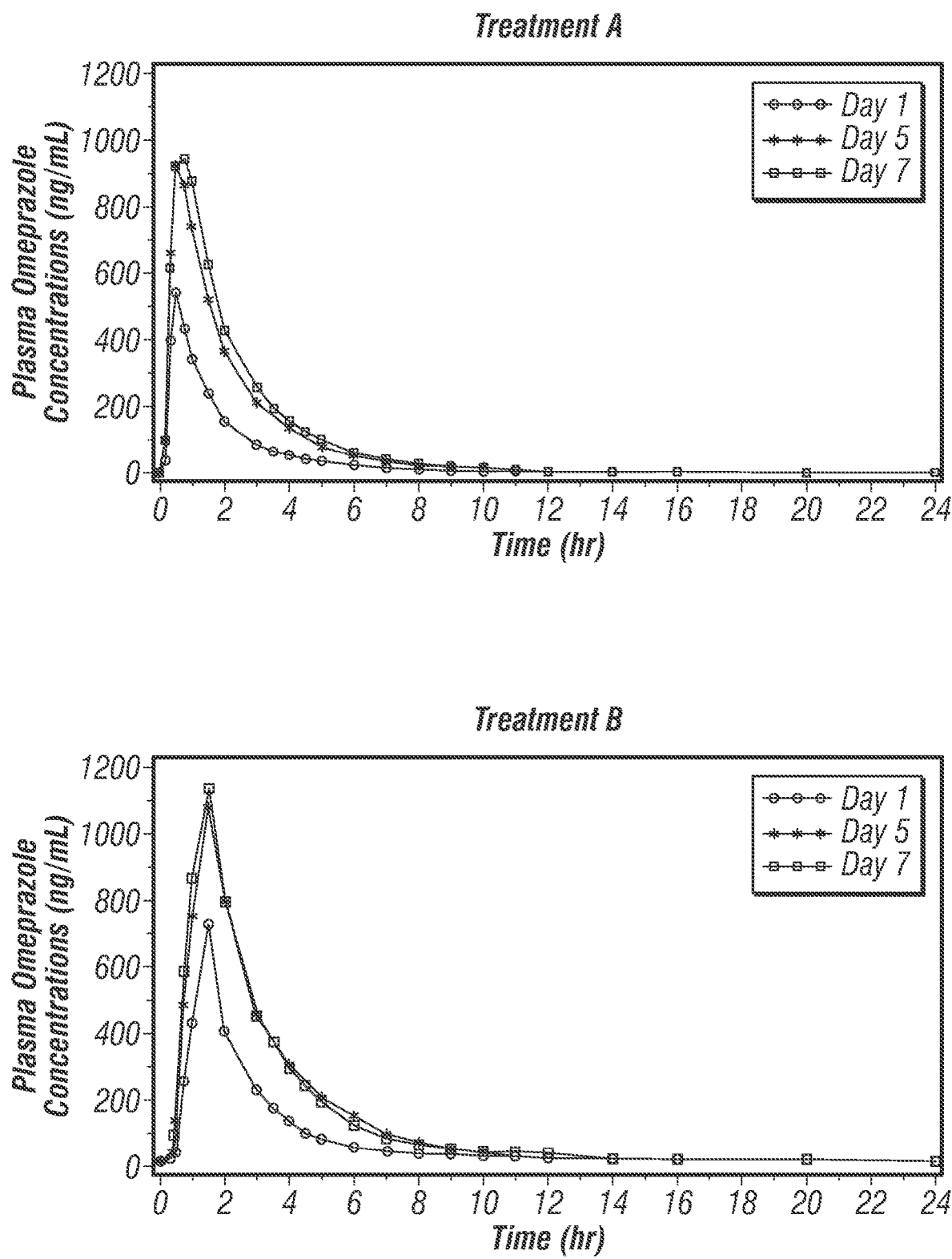
FIG. 2—Mean Plasma Omeprazole Concentration vs. Time Curves Following Single or Repeat Doses of Each Treatment.

Mean and median plasma omeprazole concentration vs. time profiles following single and repeat-dose administration for each treatment show that following repeated doses of PA32540 or EC omeprazole 40 mg, plasma omeprazole concentrations increased substantially as compared to those after a single dose. The mean plasma omeprazole concentration vs. time plots are also shown in FIG. 2.

The semi-log plots provided information on the time points used and the resultant regression line for determination of apparent half-life of omeprazole in the terminal phase. These plots exhibited generally parallel decay curves for omeprazole, indicating consistent half-life estimates between single and repeated doses and between treatments with different formulations.

Plasma Salicylic Acid Concentrations.

All available plasma salicylic acid concentration data were included in the PK data analysis. Thirteen subjects inadvertently had blood samples collected on Day 5 for measurement of salicylic acid. These data were included in PK data analysis, but not summarized. One subject (No. 1015) receiving Treatment B did not have measurable plasma concentrations of salicylic acid throughout the 24-hour sampling period on Day 7, and thus was excluded from summary statistics.

Following single or repeat doses of PA32540 or EC-ASA (Ecotrin®), plasma salicylic acid concentrations were generally measurable starting at 2-3 hours and lasting up to 16-20 hours post-dose in the majority of subjects. These observations indicated lag-time in the absorption of acetylsalicylic acid/salicylic acid, indicative of the delayed-release characteristics of both ASA formulations. One subject in each treatment had barely measurable concentrations (just above LLOQ) of salicylic acid from pre-dose to 1-1.5 hours post-dose on Day 1. Ten subjects in Treatment A (PA32540) and 11 subjects in Treatment B (EC-ASA) had measurable but low concentrations of salicylic acid from pre-dose to about 1.5-2 hours post-dose on Day 7, which were most likely residual concentrations from the previous dose.

Mean and median plasma salicylic acid concentration vs. time profiles following both treatments on each of the three PK study days show that plasma profiles of salicylic acid from the two enteric-coated ASA formulations (PA32540 and Ecotrin®) followed closely with each other and had a large overlapping portion on both Day 1 and Day 7.

Figure 3:
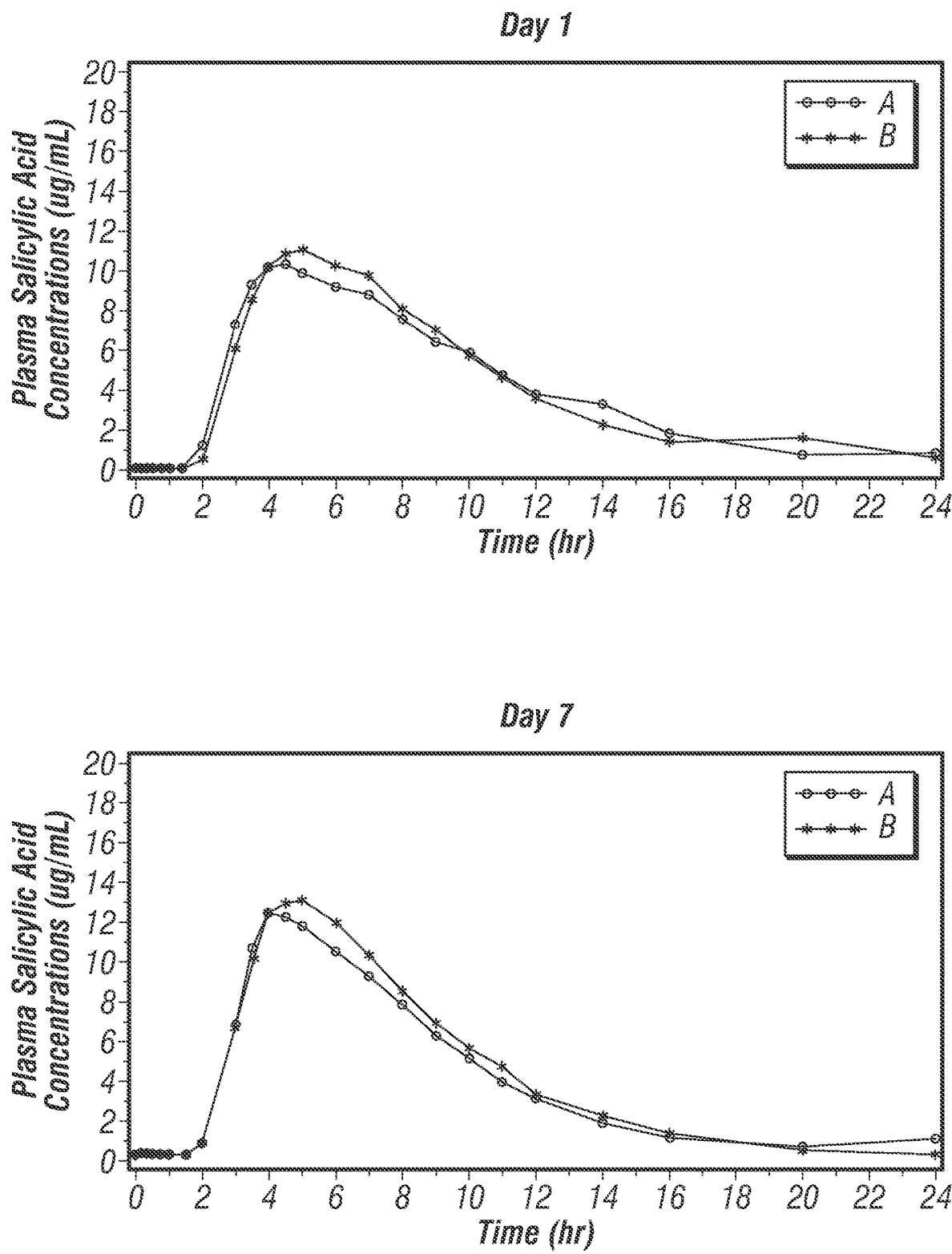
FIG. 3—Mean Plasma Salicylic Acid Concentration vs. Time Curves Following Single or Repeat Doses of Each Treatment.

Mean and median plasma salicylic acid concentration vs. time profiles following single and repeat-dose administration for each treatment show that following repeated doses of PA32540 or EC-ASA, plasma salicylic acid concentrations increased only slightly as compared to those after a single dose. The mean plasma salicylic acid concentration vs. time plots are also shown in FIG. 3.

The semi-log plots provided information on the time points used and the resultant regression line for determination of apparent half-life of salicylic acid in the terminal phase. These plots exhibited generally parallel decay curves for salicylic acid, indicating consistent half-life estimates between single and repeated doses and between treatments with different formulations.

Plasma Acetylsalicylic Acid Concentrations.

All available plasma acetylsalicylic acid concentration data were included in the PK data analysis. Thirteen subjects inadvertently had blood samples collected on Day 5 for measurement of acetylsalicylic acid. These data were included in PK data analysis, but not summarized. Two subjects receiving Treatment B did not have measurable plasma concentrations of acetylsalicylic acid throughout the 24-hour sampling period on Day 1 (No. 1024) or on Day 7 (No. 1015), and thus were excluded from summary statistics.

The semi-log plots provided information on the time points used and the resultant regression line for determination of apparent half-life of acetylsalicylic acid in the terminal phase. These plots exhibited generally parallel decay curves for acetylsalicylic acid, indicating consistent half-life estimates between single and repeated doses and between treatments with different formulations.

Omeprazole Pharmacokinetic Parameters.

Key PK parameters of omeprazole following administration of the first dose (on Day 1) and repeat daily doses of each treatment on Day 5 and Day 7 are presented in Table 9 below.

TABLE 9

Summary of Omeprazole Pharmacokinetic Parameters for Each Treatment by Study Day

| Study Day | Treatment | Statistics | $C_{max}$ (ng/mL) | $t_{max}$* (hr) | $AUC_{0-12}$ (hr*ng/mL) | $AUC_{0-24}$ (hr*ng/mL) | $AUC_{0-\infty}$ (hr*ng/mL) | $t_{1/2}$ (hr) |
|---|---|---|---|---|---|---|---|---|
| 1 | A | n | 26 | 26 | 26 | 26 | 26 | 26 |
|   |   | Mean | 617 | 0.50* | 874 | 880 | 881 | 1.00 |
|   |   | % CV | 63 |  | 107 | 109 | 109 | 40 |
|   |   | GeoMean | 466 | 0.33-1.5* | 608 | 610 | 610 | 0.939 |
| 1 | B | n | 26 | 26 | 26 | 26 | 26 | 26 |
|   |   | Mean | 869 | 1.50* | 1458 | 1549 | 1552 | 1.04 |
|   |   | % CV | 65 |  | 92 | 89 | 89 | 43 |
|   |   | GeoMean | 726 | 0.75-16* | 1106 | 1192 | 1194 | 0.958 |
| 5 | A | n | 26 | 26 | 26 | 26 |  | 26 |
|   |   | Mean | 1040 | 0.50* | 1911 | 1922 |  | 1.09 |
|   |   | % CV | 61 |  | 92 | 93 |  | 37 |
|   |   | GeoMean | 836 | 0.33-1.0* | 1278 | 1281 |  | 1.02 |
| 5 | B | n | 26 | 26 | 26 | 26 |  | 26 |
|   |   | Mean | 1288 | 1.50* | 2892 | 2929 |  | 1.26 |
|   |   | % CV | 34 |  | 53 | 55 |  | 36 |
|   |   | GeoMean | 1214 | 0.75-4.0* | 2516 | 2535 |  | 1.19 |
| 7 | A | n | 26 | 26 | 26 | 26 |  | 26 |
|   |   | Mean | 1196 | 0.50* | 2174 | 2187 |  | 1.09 |
|   |   | % CV | 71 |  | 88 | 88 |  | 35 |
|   |   | GeoMean | 903 | 0.33-1.0* | 1441 | 1446 |  | 1.03 |
| 7 | B | n | 26 | 26 | 26 | 26 |  | 26 |
|   |   | Mean | 1345 | 1.25* | 2890 | 2985 |  | 1.19 |
|   |   | % CV | 44 |  | 58 | 59 |  | 36 |
|   |   | GeoMean | 1218 | 0.75-3.5* | 2495 | 2558 |  | 1.13 |

*Values for $t_{max}$ are median and range.
GeoMean = geometric mean.
Treatment A: One tablet of PA32540 (EC-ASA 325 mg and IR omeprazole 40 mg) administered 60 minutes prior to breakfast once daily for 7 days.
Treatment B: One tablet of EC-ASA (Ecotrin ®) 325 mg + one capsule of EC omeprazole (Prilosec ®) 40 mg administered 60 minutes prior to breakfast once daily for 7 days.

Following single or repeat doses of PA32540 or EC-ASA (Ecotrin®), plasma acetylsalicylic acid concentrations were measurable starting at 2-3 hours post-dose in the majority of subjects. As expected, plasma acetylsalicylic acid concentrations were low and were only measurable over a short period, up to about 6 hours post-dose in the majority of subjects.

Mean and median plasma acetylsalicylic acid concentration vs. time profiles following both treatments on each of the three PK study days show that mean/median plasma profiles of acetylsalicylic acid from the two enteric-coated ASA formulations were almost superimposable on both Day 1 and Day 7.

Figure 4:
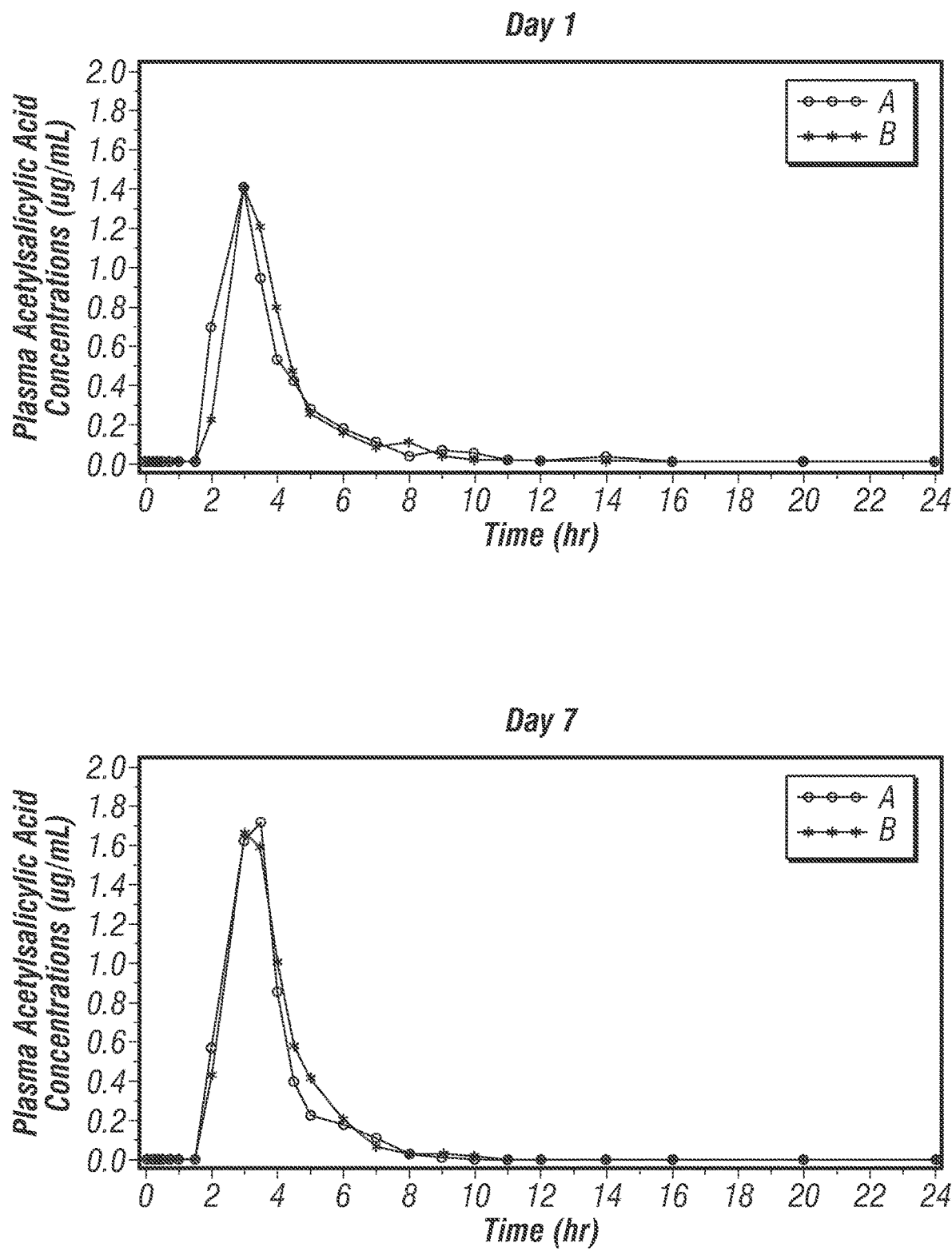
FIG. 4—Mean Plasma Acetylsalicylic Acid Concentration vs. Time Curves Following Single or Repeat Doses of Each Treatment.

Mean and median plasma acetylsalicylic acid concentration vs. time profiles following single and repeat-dose administration in each treatment show that following repeated doses of PA32540 or EC-ASA, plasma acetylsalicylic acid concentrations increased slightly as compared to those after a single dose. The mean plasma acetylsalicylic acid concentration vs. time plots are also shown in FIG. 4.

Following single or repeat daily oral administration of PA32540 (containing 40 mg immediate-release omeprazole), omeprazole was rapidly absorbed with median peak plasma concentration occurring at about 0.5 hour post-dose on each day. As expected, delayed absorption of omeprazole from Prilosec® (an EC formulation) was observed, as shown by the median $t_{max}$ occurring at 1.5 hours post dose on each day. The $t_{max}$ values in individual subjects showed a wider range following administration of the EC formulation.

Omeprazole was rapidly eliminated from plasma with a mean terminal half-life of approximately 1 hour following single or repeat-dose administration of either formulation.

Plasma exposure to omeprazole following single or repeat-dose administration of PA32540 was less than that following administration of EC omeprazole 40 mg. Results of statistical analysis of omeprazole pharmacokinetic parameters between treatments (A vs. B) are presented in Table 10 below.

TABLE 10

Summary of Statistical Analysis Results of Omeprazole Pharmacokinetic Parameters between Treatments

| Omeprazole PK Parameter | Treatment A vs. Treatment B GLSM Ratio (90% Confidence Interval) | | |
|---|---|---|---|
| | Day 1 | Day 5 | Day 7 |
| $AUC_{0-24}$ (hr*ng/mL) | 0.511 (0.422-0.620) | 0.505 (0.403-0.634) | 0.565 (0.454-0.703) |
| $AUC_{0-12}$ (hr*ng/mL) | 0.550 (0.439-0.688) | 0.508 (0.405-0.637) | 0.578 (0.462-0.722) |
| $C_{max}$ (ng/mL) | 0.642 (0.473-0.870) | 0.689 (0.564-0.842) | 0.741 (0.592-0.928) |

GLSM = geometric least-squares mean.
Treatment A: One tablet of PA32540 (EC-ASA 325 mg and IR omeprazole 40 mg) administered 60 minutes prior to breakfast once daily for 7 days;
Treatment B: One tablet of EC-ASA (Ecotrin ®) 325 mg + one capsule of EC omeprazole (Prilosec ®) 40 mg administered 60 minutes prior to breakfast once daily for 7 days The above results show that IR omeprazole in PA32540 produced overall plasma exposure (as measured by AUCs) that was only 51-57% of that produced by EC omeprazole in Prilosec® for the same dose amount of omeprazole (40 mg) in the formulations.

There was large intersubject variability in $C_{max}$ and AUC values of omeprazole following either single or repeat doses of PA32540 or EC omeprazole (Prilosec®). The intersubject variability appeared to be greater with administration of PA32540 (% CV ranging from 88-109% for $AUC_{0-24}$ and 61-71% for $C_{max}$) than EC omeprazole 40 mg (% CV ranging from 59-89% for $AUC_{0-24}$ and 34-65% for $C_{max}$). In general, the variability in AUC values was greater following first-dose administration (Day 1) as compared to that after repeat-dose administration.

Following repeat daily doses of PA32540 or EC omeprazole 40 mg, plasma exposure to omeprazole increased substantially (more than doubled), with mean $C_{max}$ and $AUC_{0-24}$ ratios, Day 7 to Day 1, of 2.90 and 3.02 for Treatment A (PA32540) and of 2.17 and 2.26 for Treatment B (EC omeprazole 40 mg), respectively. Results of statistical analysis of omeprazole PK parameters between study days are presented in Table 11.

TABLE 11

Summary of Statistical Analysis Results of Omeprazole Pharmacokinetic Parameters between Study Days

| PK Parameter | Omeprazole | | | | | |
|---|---|---|---|---|---|---|
| | Treatment A | | | Treatment B | | |
| | Day 5/Day 1 | Day 7/Day 1 | Day 7/Day 5 | Day 5/Day 1 | Day 7/Day 1 | Day 7/Day 5 |
| $AUC_{0-24}$ (hr*ng/mL) | 2.10 (1.69-2.62) | 2.37 (1.90-2.96) | 1.13 (0.91-1.41) | 2.13 (1.92-2.35) | 2.15 (1.94-2.37) | 1.01 (0.912-1.12) |
| $AUC_{0-12}$ (hr*ng/mL) | 2.10 (1.69-2.62) | 2.37 (1.90-2.96) | 1.13 (0.904-1.41) | 2.28 (1.98-2.61) | 2.26 (1.96-2.59) | 0.991 (0.863-1.14) |
| $C_{max}$ (ng/mL) | 1.80 (1.35-2.39) | 1.94 (1.46-2.58) | 1.08 (0.812-1.44) | 1.67 (1.39-2.02) | 1.68 (1.39-2.03) | 1.00 (0.831-1.21) |

Values are geometric least-squares mean and associated (90% confidence interval).
Treatment A: One tablet of PA32540 (EC-ASA 325 mg and IR omeprazole 40 mg) administered 60 minutes prior to breakfast once daily for 7 days;
Treatment B: One tablet of EC-ASA (Ecotrin ®) 325 mg + one capsule of EC omeprazole (Prilosec ®) 40 mg administered 60 minutes prior to breakfast once daily for 7 days.

The accumulation ratios for $C_{max}$ and $AUC_{0-24}$ of omeprazole were 1.94 and 2.37 following seven daily doses of PA32540, and were 1.68 and 2.15 following seven daily doses of EC omeprazole. The between-day analysis of omeprazole PK parameters indicated that plasma omeprazole achieved a steady-state condition on Day 5 following daily administration of EC omeprazole, with Day 7 to Day 5 parameter ratios having a point estimate of 1.0 and a 90% CI falling within 0.80 and 1.25. For PA32540, the Day 7 to Day 5 parameter ratios were slightly (about 10%) greater than 1.0, indicating that plasma omeprazole approaches a steady-state condition by Day 5. The comparative box plots also showed that omeprazole PK parameter estimates were comparable between Day 5 and Day 7 following daily administration of PA32540.

Salicylic Acid Pharmacokinetic Parameters.

The PK parameters of salicylic acid following administration of the first dose (on Day 1) and repeat daily doses of each treatment on Day 7 are presented in Table 12 below.

Plasma salicylic acid was eliminated with a mean half-life of 2.2 to 2.4 hours, which was similar between study days and between formulations.

Plasma exposure to salicylic acid following single or repeat-dose administration of PA32540 was comparable to that following administration of Ecotrin®, as shown by the ratios of $C_{max}$ and $AUC_{0-24}$ values, Treatment A vs. Treatment B on each study day, which were generally close to 1.0. Further results of formulation comparison in terms of plasma exposure to salicylic acid are presented in Section 11.3.2.4 below.

Overall plasma exposure to salicylic acid was similar following the first-dose and repeat-dose administration of each formulation. The daily $AUC_{0-24}$ ratio, Day 7 to Day 1, was close to 1.0 for both treatments. The salicylic acid $C_{max}$ ratio, Day 7 to Day 1, was about 1.1 for both treatments. Results of ANOVA showed that salicylic acid $C_{max}$ and $AUC_{0-24}$ ratios, Day 7 to Day 1, were not significantly different from 1.0 for each treatment, indicating no accumulation of plasma salicylic acid following repeat daily doses of the two delayed-release formulations of ASA.

TABLE 12

Summary of Salicylic Acid Pharmacokinetic Parameters for Each Treatment by Study Day

| Study Day | Treatment | Statistics | $C_{max}$ (µg/mL) | $t_{max}$* (hr) | $AUC_{0-t}$ (hr*µg/mL) | $AUC_{0-24}$ (hr*µg/mL) | $AUC_{0-\infty}$ (hr*µg/mL) | $t^{1/2}$ (hr) |
|---|---|---|---|---|---|---|---|---|
| 1 | A | n | 26 | 26 | 25 | 25 | 25 | 25 |
|   |   | Mean | 15.5 | 4.50* | 94.6 | 94.8 | 96.4 | 2.40 |
|   |   | % CV | 28 |  | 43 | 43 | 45 | 34 |
|   |   | GeoMean | 14.9 | 3.0-24* | 88.3 | 88.6 | 89.5 | 2.31 |
| 1 | B | n | 26 | 26 | 24 | 24 | 24 | 24 |
|   |   | Mean | 15.3 | 4.50* | 96.2 | 96.5 | 97.9 | 2.42 |
|   |   | % CV | 27 |  | 44 | 43 | 46 | 32 |
|   |   | GeoMean | 14.8 | 3.0-20* | 89.3 | 89.6 | 90.5 | 2.33 |
| 7 | A | n | 26 | 26 | 26 | 26 |  | 25 |
|   |   | Mean | 16.2 | 4.50* | 91.0 | 91.3 |  | 2.26 |
|   |   | % CV | 29 |  | 55 | 55 |  | 34 |
|   |   | GeoMean | 15.6 | 3.0-24* | 82.1 | 82.5 |  | 2.18 |
| 7 | B | n | 25 | 25 | 25 | 25 |  | 25 |
|   |   | Mean | 16.6 | 4.00* | 97.1 | 97.4 |  | 2.34 |
|   |   | % CV | 26 |  | 44 | 44 |  | 35 |
|   |   | GeoMean | 16.1 | 3.0-11* | 90.5 | 90.8 |  | 2.24 |

*Values for tmax are median and range.
GeoMean = geometric mean.
Treatment A: One tablet of PA32540 (EC-ASA 325 mg and IR omeprazole 40 mg) administered 60 minutes prior to breakfast once daily for 7 days;
Treatment B: One tablet of EC-ASA (Ecotrin ®) 325 mg + one capsule of EC omeprazole (Prilosec ®) 40 mg administered 60 minutes prior to breakfast once daily for 7 days.

Following oral administration of either PA32540 or EC-ASA (Ecotrin®) 325 mg, there was an apparent lag time in the absorption of acetylsalicylic acid/salicylic acid. Peak plasma salicylic acid concentrations occurred over a wide range of time, about 3-24 hours post-dose following the first dose or repeat doses of PA32540, and about 3-20 hours post-first dose of EC-ASA 325 mg. The $t_{max}$ range following repeat does of EC-ASA 325 mg appeared to reduce slightly. The median $t_{max}$ values for both formulations were similar, 4.5 hours post-first dose, and 4-4.5 hours following repeat doses.

The intersubject variability in plasma exposure to salicylic acid was similar after single and repeat-dose administration of either formulation and was similar between formulations, 26-29% for $C_{max}$ and 43-55% for $AUC_{0-24}$.

Acetylsalicylic Acid Pharmacokinetic Parameters.

The PK parameters of acetylsalicylic acid following administration of the first dose (on Day 1) and repeat daily doses of each treatment on Day 7 are presented in Table 13 below.

TABLE 13

Summary of Acetylsalicylic Acid Pharmacokinetic Parameters for Each Treatment by Study Day

| Study Day | Treatment | Statistics | $C_{max}$ (µg/mL) | $t_{max}$* (hr) | $AUC_{0-t}$ (hr*µg/mL) | $AUC_{0-24}$ (hr*µg/mL) | $AUC_{0-\infty}$ (hr*µg/mL) | $t^{1/2}$ (hr) |
|---|---|---|---|---|---|---|---|---|
| 1 | A | n | 26 | 26 | 25 | 24 | 24 | 24 |
|   |   | Mean | 2.36 | 3.0* | 3.25 | 3.36 | 3.36 | 0.450 |

TABLE 13-continued

Summary of Acetylsalicylic Acid Pharmacokinetic Parameters for Each Treatment by Study Day

| Study Day | Treatment | Statistics | $C_{max}$ (μg/mL) | $t_{max}$* (hr) | $AUC_{0-t}$ (hr*μg/mL) | $AUC_{0-24}$ (hr*μg/mL) | $AUC_{0-\infty}$ (hr*μg/mL) | $t^{1/2}$ (hr) |
|---|---|---|---|---|---|---|---|---|
| | | % CV | 56 | | 36 | 34 | 34 | 23 |
| | | GeoMean | 1.91 | 2.0-24* | 3.05 | 3.18 | 3.18 | 0.440 |
| 1 | B | n | 25 | 25 | 24 | 22 | 22 | 22 |
| | | Mean | 2.21 | 3.5* | 3.08 | 3.15 | 3.15 | 0.427 |
| | | % CV | 55 | | 44 | 43 | 43 | 21 |
| | | GeoMean | 1.72 | 2.0-20* | 2.70 | 2.78 | 2.78 | 0.418 |
| 7 | A | n | 26 | 26 | 24 | 24 | | 24 |
| | | Mean | 2.91 | 3.5* | 3.88 | 3.91 | | 0.388 |
| | | % CV | 54 | | 37 | 37 | | 14 |
| | | GeoMean | 2.16 | 2.0-24* | 3.63 | 3.66 | | 0.385 |
| 7 | B | n | 25 | 25 | 25 | 25 | | 25 |
| | | Mean | 2.87 | 3.5* | 3.78 | 3.80 | | 0.385 |
| | | % CV | 42 | | 40 | 40 | | 15 |
| | | GeoMean | 2.59 | 2.0-9.0* | 3.48 | 3.51 | | 0.381 |

*Values for tmax are median and range.
GeoMean = geometric mean.
Treatment A: One tablet of PA32540 (EC-ASA 325 mg and IR omeprazole 40 mg) administered 60 minutes prior to breakfast once daily for 7 days;
Treatment B: One tablet of EC-ASA (Ecotrin®) 325 mg + one capsule of EC omeprazole (Prilosec®) 40 mg administered 60 minutes prior to breakfast once daily for 7 days.

Following oral administration of either PA32540 or EC-ASA (Ecotrin®), peak plasma acetylsalicylic acid concentrations occurred over a wide range of time, similar to that observed above for salicylic acid. The median $t_{max}$ values for both formulations following single or repeat doses were similar, 3 to 3.5 hours post-dose, which is about 1 hour shorter than that observed for its metabolite, salicylic acid.

Plasma acetylsalicylic acid was eliminated very rapidly, with a mean half-life of 0.38 to 0.45 hour, which was similar between study days and between formulations.

The intersubject variability in plasma exposure to acetylsalicylic acid was similar after single and repeat-dose administration of either formulation and was similar between formulations, 42-56% for $C_{max}$ and 34-43% for $AUC_{0-24}$.

Unlike that for salicylic acid, plasma exposure to acetylsalicylic acid increased with repeat daily doses of PA32540 or EC-ASA 325 mg, as shown by the ratios of $C_{max}$ and $AUC_{0-24}$ values, Day 7 vs. Day 1, for both treatments. Acetylsalicylic acid $C_{max}$ and $AUC_{0-24}$ ratios, Day 7 to Day 1, were 2.20 and 1.27 for PA32540, and were 3.03 and 1.94 for EC-ASA 325 mg.

Mean plasma exposure to acetylsalicylic acid following single-dose administration of PA32540 was slightly higher than that of EC-ASA 325 mg, as shown by the $C_{max}$ and $AUC_{0-24}$ ratios, Treatment A vs. Treatment B. However, following repeat-dose administration, plasma exposure to acetylsalicylic acid was comparable between the two delayed-release formulations of ASA, with mean $C_{max}$ and $AUC_{0-24}$ ratios, Treatment A vs. Treatment B, close to 1.0.

Statistical Analysis Results of Pharmacokinetic Parameters of Salicylic Acid and Acetylsalicylic Acid.

Results of statistical analysis (ANOVA) of PK parameters of salicylic acid and acetylsalicylic acid between treatments (formulations) are summarized below in Table 14.

TABLE 14

Summary of Statistical Analysis Results of Pharmacokinetic Parameters of Salicylic Acid and Acetylsalicylic Acid between Treatments (Formulations)

| | Treatment A vs. Treatment B GLSM Ratio (90% Confidence Interval) | | | |
|---|---|---|---|---|
| PK | Salicylic Acid | | Acetylsalicylic Acid | |
| Parameter | Day 1 | Day 7 | Day 1 | Day 7 |
| $AUC_{0-24}$ (hr*μg/mL) | 0.978 (0.937-1.02) | 0.905 (0.820-0.999) | 1.12 (0.877-1.43) | 1.02 (0.887-1.17) |
| $C_{max}$ (μg/mL) | 1.01 (0.907-1.13) | 0.964 (0.867-1.07) | 1.12 (0.756-1.65) | 0.820 (0.575-1.17) |

GLSM = geometric least-squares mean.
Treatment A: One tablet of PA32540 (EC-ASA 325 mg and IR omeprazole 40 mg) administered 60 minutes prior to breakfast once daily for 7 days;
Treatment B: One tablet of EC-ASA (Ecotrin®) 325 mg + one capsule of EC omeprazole (Prilosec®) 40 mg administered 60 minutes prior to breakfast once daily for 7 days These results showed that the 90% CI for the geometric least-squares mean (GLSM) ratios (PA32540 vs. Ecotrin®) for salicylic acid $C_{max}$ and $AUC_{0-24}$ were all within the 0.80 to 1.25 limits while containing 1.0 on Day 1 and Day 7, indicating that PA32540 is bioequivalent to Ecotrin® in terms of AUC and $C_{max}$ of salicylic acid following single- or repeat-dose administration.

The 90% CI for GLSM ratios (PA32540 vs. Ecotrin®) for $AUC_{0-24}$ of acetylsalicylic acid on Day 7 was within the 0.80 to 1.25 limit, indicating that PA32540 is bioequivalent to Ecotrin® in terms of acetylsalicylic acid $AUC_{0-24}$ following repeat-dose administration. For acetylsalicylic acid $C_{max}$ ratios on Days 1 and 7 and acetylsalicylic acid $AUC_{0-24}$ ratio on Day 1, the 90% CIs contained 1.0, indicating that the two formulations were not statistically significantly different in terms of these parameters. However, the three confidence intervals were outside the 0.80 to 1.25 limit and were very wide, indicating large variability and lack of statistical power for treatment comparison.

Pharmacokinetic Conclusions.

The pharmacokinetic conclusions were as follows:

The immediate-release (IR) omeprazole was rapidly absorbed from the PA32540 tablet with a median $t_{max}$ of 0.5 hour following single or repeat-dose administration. Delayed absorption of omeprazole from Prilosec® (an enteric-coated formulation) was observed, with a median $t_{max}$ of 1.5 hours.

The relative bioavailability of omeprazole from PA32540 following single or repeat-dose administration was only 51-57% of that from an enteric-coated (EC) formulation of omeprazole 40 mg (Prilosec®).

Omeprazole was rapidly eliminated from plasma with a mean half-life of approximately 1 hour following single or repeat-dose administration of either formulation.

Plasma omeprazole concentrations increased substantially (more than doubled) following repeat-dose administration of either formulation. Steady-state conditions were achieved following 5 to 7 daily doses of either formulation.

Plasma profiles of acetylsalicylic acid and its metabolite, salicylic acid, following single or repeat-dose administration of PA32540 or Ecotrin® 325 mg exhibited delayed-release characteristics. Median $t_{max}$ occurred at 3-3.5 hours post-dose for acetylsalicylic acid, and at 4 to 4.5 hours post-dose for salicylic acid following single or repeat-dose administration of either formulation.

Plasma concentrations of acetylsalicylic acid were low and only measurable over a short period, from 2 to 6 hours post-dose of either formulation, and thus were associated with large intersubject and intrasubject variability, especially for $C_{max}$. In comparison, plasma concentrations of salicylic acid were higher and measurable in plasma for a longer period, from 2 to 20 hours post-dose of either formulation.

Mean plasma profiles of acetylsalicylic acid from single or repeat-dose administration of the two formulations, PA32540 and Ecotrin®, were almost superimposable. PA32540 is bioequivalent to Ecotrin® in terms of steady-state AUC of acetylsalicylic acid.

PA32540 is bioequivalent to Ecotrin® in terms of AUC and $C_{max}$ of salicylic acid following single or repeat-dose administration.

Safety Evaluation/Extent of Exposure.

A total of 26 subjects received all 7 doses of PA32540, and all 7 doses of EC-ASA 325 mg and all 7 doses of EC omeprazole 40 mg.

Brief Summary of Adverse Events.

An overview of adverse events is displayed in Table 15. There were no serious adverse events reported and no subject withdrew from the study due to an adverse event. The overall incidence of adverse events ranged from 15% to 19%, and all events were mild or moderate in severity.

TABLE 15

Overview of Adverse Events-Safety Population

| Treatment | PA32540<br>N = 26<br>n (%) | EC-ASA 325 mg + Prilosec<br>40 mg Concomitantly<br>N = 26<br>n (%) |
|---|---|---|
| Subjects with at least one adverse event | 4 (15) | 5 (19) |
| Subjects with at least one serious adverse event | 0 | 0 |
| Deaths | 0 | 0 |
| Withdrawals due to adverse events | 0 | 0 |

Display and Analysis of Adverse Events.

All AEs occurring in the safety population are displayed in in-text Table 16. No single AE occurred more frequently than any other AE.

TABLE 16

All Adverse Events-Safety Population

| System Organ<br>Class Adverse Event | PA32540<br>N = 26<br>n (%) | EC-ASA 325 mg +<br>Prilosec<br>40 mg Concomitantly<br>N = 26<br>n (%) |
|---|---|---|
| Gastrointestinal disorders | 2 (8) | 2 (8) |
| Frequent bowel movements | 1 (4) | 1 (4) |
| Constipation | 1 (4) | 0 |
| Flatulence | 0 | 1 (4) |
| Infections and infestations | 1 (4) | 3 (12) |
| Gastroenteritis viral | 0 | 1 (4) |
| Respiratory tract infection | 0 | 1 (4) |
| Upper respiratory tract infection | 0 | 1 (4) |
| Vulvovaginal candidiasis | 1 (4) | 0 |
| Nervous system disorders | 1 (4) | 0 |
| Migraine | 1 (4) | 0 |

The gastrointestinal disorders (frequent bowel movements, constipation, and flatulence) were all assessed as treatment-related AEs. All AEs were mild or moderate in severity.

Listing and Adverse Events by Subject.

No adverse events required any action or medications.

Deaths, Other Serious Adverse Events, and Other Significant Adverse Events.

There were no deaths or other serious adverse events. There were also no significant AEs or discontinuations due to AEs.

Clinical Laboratory Evaluation/Listing of Individual Laboratory Measurements by Subject and Each Abnormal Laboratory Value.

Results of the urine drug screen (including ethanol) are shown in Listing 16.2.6. Two subjects (subjects 1019 and 1026) had a positive urine drug screen. No subject had a positive urine pregnancy test during the study.

Evaluation of Each Laboratory Parameter/Laboratory Values Over Time.

Mean and median values for laboratory parameters were similar at the Screening and Final Visits.

Individual Subject Changes.

Final Visit laboratory assessments were conducted approximately 1 month following the final dose of study drug. There were 6 subjects whose blood chemistry values shifted from normal at Screening to abnormal at the Final visit. The majority of these involved changes in alkaline phosphatase (1 subject experienced an increase to an above normal value and 3 subjects experienced a decrease to below normal values). A decrease to a below normal value for BUN occurred in 1 subject and for total bilirubin in 1 subject. None of these changes were considered clinically significant and no abnormal test result was repeated.

There were 17 subjects whose hematology values shifted from normal at Screening to abnormal at the Final visit. A decrease to below normal values occurred in hematocrit (8 subjects), RBCs (8 subjects), hemoglobin (2 subjects), lymphocytes (3 subjects), and WBC (1 subject). An increase to above normal values occurred in neutrophils (6 subjects), eosinophils (1 subject), and lymphocytes (2 subjects). None of these changes were considered clinically significant and no abnormal test result was repeated.

Urine test results were negative for blood in 85% of subjects at Screening and 92% at Final visit. Bacteria were present in the urine in 19% of subjects at Screening and in 35% of subjects at Final visit. No subject had glucose in their urine at either Screening or Final visit. No subject had proteins in their urine at Screening; at Final Visit, proteins were present in the urine of 1 subject. None of the urinalysis changes were considered clinically significant, and no abnormal test result was repeated.

Individual Clinically Significant Abnormalities.

There were no clinically significant laboratory findings in the study.

Safety Conclusions.

All treatments in the study were well tolerated.

Example 3—Discussion

PA32540 is a multi-layered oral combination tablet of EC-ASA 325 mg and immediate-release (IR) omeprazole 40 mg in a coordinated delivery system. The rationale for the product is to reduce the known gastrotoxicity of ASA. The PA tablet is unique in that the proton pump inhibitor (PPI) is not enteric-coated or buffered, as it is in all other approved PPI products. Instead, omeprazole is contained in another layer of the PA tablet in an IR form. This IR formulation allows the therapeutic activity (raising intragastric pH) of omeprazole to start rapidly after ingestion. To further ensure the sequential delivery of the two components, the ASA core is enteric-coated to prevent dissolution of the core until the surrounding environment of the tablet reaches a pH of >5.5. As a result, intragastric pH is substantially increased by the time the offending agent, ASA, is delivered to the stomach systemically.

Omeprazole, like other proton pump inhibitors, is acid labile (Clissold 1986; Horn 2005), and the absorption characteristics of omeprazole are both formulation- and dose-dependent (Clissold 1986). Due to instability of PPI compounds at low gastric pH, most currently marketed PPIs are enteric-coated, including Prilosec® (EC omeprazole). While this prevents degradation of omeprazole in the highly acidic milieu of the stomach, it also results in delayed absorption and delayed onset of action (Howden 2005).

In this study, once-daily administration of PA32540 (with IR omeprazole) was compared with once-daily co-administration of EC-ASA (Ecotrin®) 325 mg+EC (or delayed-release) omeprazole (Prilosec®) 40 mg. The primary objective was to determine the effect of each product on intragastric pH after 7 days of therapy and the secondary objective was to evaluate the single and multiple-dose PKs of omeprazole, salicylic acid and ASA.

Plasma concentrations of omeprazole increased substantially (more than doubled) following repeat-dose administration of either formulation, most likely due to increase oral bioavailability (Clissold 1986), and exhibited time-dependent kinetics. Also, a steady-state condition was achieved after 5 to 7 days; this is much longer than that expected based on linear kinetics and plasma omeprazole half-life (about 1 hour), which was unchanged following repeat doses and was similar for both formulations. As expected (due to the instability of omeprazole at low pH in the stomach), the relative bioavailability of omeprazole from PA32540, which releases omeprazole in the stomach, was only 51-57% of that from EC omeprazole 40 mg (geometric least squares mean $AUC_{0-24}$ for omeprazole on Day 7 was 1146 hr*ng/mL for PA32540 and 2558 hr*ng/mL for EC omeprazole 40 mg).

Although on a mg to mg basis both treatments evaluated in this study contain 40 mg of omeprazole, the different pharmacokinetics of IR and EC omeprazole lead, as expected, to a different pharmacodynamic profile. Importantly, mean time to intragastric pH >4 was achieved approximately 50% faster with PA32540 compared with EC omeprazole 40 mg (17 minutes vs. 36 minutes, respectively; P=0.011). This earlier pH effect seen with PA32540 is related to median time to maximum plasma concentration ($T_{max}$), which occurred about 1 hour earlier following administration of PA32540 (at 0.5 hour post-dose) compared with EC omeprazole 40 mg (at 1.25 to 1.5 hours post-dose). In assessing the 24-hour pH effect (primary objective of the study), mean percent time intragastric pH >4 was 51% for PA32540 vs. 58% for EC omeprazole (P=0.004).

Regarding the ASA component of PA32540, oral absorption and bioavailability of acetylsalicylic acid/salicylic acid were comparable between PA32540 and a currently marketed EC-ASA formulation such as Ecotrin®. PA32540 was found to be bioequivalent to Ecotrin® in terms of AUC and $C_{max}$ of salicylic acid following single or repeat-dose administration. Due to the enteric coating, the absorption of acetylsalicylic acid/salicylic acid from either PA32540 or Ecotrin®, occurred with median $t_{max}$ at 3-3.5 hours post-dose for acetylsalicylic acid, and at 4-4.5 hours post-dose for salicylic acid following single or repeat-dose administration of either formulation.

The data presented above show that the pharmacodynamic results and the PK results support the release characteristics of the two formulations in PA32540. Peak plasma concentration of omeprazole is reached in 30 minutes with PA32540 and onset of GI effect (pH>4) at 17 minutes, thus demonstrating rapid absorption and rapid onset of GI therapeutic activity. Likewise, the data are consistent with a well-known characteristic of omeprazole, i.e. the gastric acid inhibitory effect correlates with AUC (and not $C_{max}$) (Lind 1983). There was significant lag time compared to omeprazole in the absorption of ASA from either PA32540 with median $t_{max}$ occurred at 3-3.5 hours post dose.

The finding that mean percent time intragastric pH >4 was 51% for PA32540 is similar to published data for EC omeprazole 20 mg at 49% (Kirchheiner 2009). These data support that 40 mg of IR omeprazole from PA32540 provides 24-hour pH control comparable to the pH control achieved with currently marketed 20 mg EC omeprazole. Data from a Phase 1 clinical study (PA325-106) have demonstrated a significantly lower incidence of UGI mucosal damage with PA32540 compared with 325 mg of a commercially available EC-ASA product alone. Although the percent time intragastric pH>4 with PA32540 was statistically lower than with Prilosce 40 mg the gastroprotective effects of PA32450 should be comparable to the known gastroprotective effects of Prilosec 20 mg (Omnium and Astronount studies).

Proton pump inhibitors (PPIs) as the preferred agents for the treatment and prophylaxis of ASA-associated gastrointestinal (GI) injury in patients who are at risk for GI adverse events (Bhatt 2008, Abraham 2010). Although physicians may co-prescribe PPIs with ASA, a lack of patient compliance may seriously limit the potential benefit of this strategy. Non-compliance has been recognized as a special risk in several patient populations, including the elderly, who are at increased risk of ASA-associated UGI complications (Mok 2002). PA32540 is being investigated for the secondary prevention of cardiovascular events in patients at risk for developing ASA-associated ulcers. Thus, use of a single combination tablet will ensure that patients who require daily ASA therapy will always receive a dose of PPI in conjunction with a dose of ASA in a consistent and coordinated approach that ensures compliance and enables more effective reduction of risk of UGI injury.

Overall study conclusions were as follows:
PA32540 provides 24-hour gastric pH control comparable to EC omeprazole 20 mg, with about 50% of the systemic exposure to omeprazole compared to an equivalent dose of currently marketed EC omeprazole 40 mg (Prilosec®).

Plasma concentrations of omeprazole more than doubled following repeat-dose administration of either PA32540 or EC omeprazole 40 mg, and steady-state conditions were achieved after 5 to 7 days of once-daily dosing with either formulation.

PA32540 is bioequivalent to Ecotrin® in terms of steady-state AUC of acetylsalicylic acid, and in terms of AUC and $C_{max}$ of salicylic acid following single or repeat-dose administration.

Moreover, all treatments in the study were well-tolerated.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. References

The following references, to the extent that they provide exemplary procedural or other details supplementary to those set forth herein, are specifically incorporated herein by reference.

Abraham N S, Hlatky M A, Antman E M, et al. ACCF/ACG/AHA 2010 expert consensus document on the concomitant use of proton pump inhibitors and thienopyridines: a focused update of the ACCF/ACG/AHA 2008 expert consensus document on reducing the gastrointestinal risks of antiplatelet therapy and NSAID use. *Am J Gastroenterol*. 2010; 105:2533-2549.

Alberts M J, Fort J, Orlemans E, Unal C, Plachetka J. Efficacy and safety of PA, a novel combination of enteric-coated acetylsalicylic acid and immediate-release omeprazole [abstract P507]. *Stroke*. 2009; 40:e104-276.

Antithrombotic Trialists' Collaboration. Collaborative meta-analysis of randomised trials of antiplatelet therapy for prevention of death, myocardial infarction, and stroke in high risk patients. *Br Med J*. 2002; 324:71-86.

Bhatt D L, Scheiman J, Abraham N S, et al. ACCF/ACG/AHA 2008 expert consensus document on reducing the gastrointestinal risks of antiplatelet therapy and NSAID use: a report of the American College of Cardiology Foundation Task Force on Clinical Expert Consensus Documents. *J Am Coll Cardiol*. 2008; 52:1502-1517.

Clissold S P, Campoli-Richards D M. Omeprazole. A preliminary review of its pharmacodynamic and pharmacokinetic properties, and therapeutic potential in peptic ulcer disease and Zolliger-Ellison Syndrome. *Drugs*. 1986; 32:15-47.

De Abajo F J, Rodriguez L A G. Risk of upper gastrointestinal bleeding and perforation associated with low-dose acetylsalicylic acid as plain and enteric-coated formulations. *BMC Clin Pharmacol*. 2001; 1:1.

Fort J, Orlemans, E, Unal C, Plachetka J. PA, a novel combination of delayed release (DR) acetylsalicylic acid (ASA) and immediate-release (IR) omeprazole, is associated with a decreased risk of gastroduodenal mucosal injury: pooled data from three phase 1, 4-week endoscopic studies [abstract 1246]. *Am J Gastroenterol*. 2008; 103:5487-5488.

Gurbel P A, Fort J G, Orlemans E, Plachetka J. PA32520 (single-tablet of enteric-coated acetylsalicylic acid 325 mg+immediate-release omeprazole 20 mg): acetylsalicylic acid therapy combining greater thromboxane suppression and lower upper gastrointestinal damage [abstract 4267]. *Circulation*. 2008; 118:5855.

Howden C W. Review article: immediate-release proton-pump inhibitor therapy—potential advantages. *Aliment Pharmacol Ther*. 2005; 22 Suppl 3:25-30.

Horn J R, Howden C W. Review article: Similarities and differences among delayed-release proton-pump inhibitor formulations. *Aliment Pharmacol Ther*. 2005; 22 Suppl 3:20-24.

Kelly J P, Kaufman D W, Jurgelon J M, Sheehan J, Koff R S, Shapiro S. Risk of acetylsalicylic acid-associated major upper-gastrointestinal bleeding with enteric-coated or buffered product. *Lancet*. 1996; 348:1413-1416.

Kirchheiner J, Glatt S, Fuhr U, et al. Relative potency of proton-pump inhibitors—comparison of effects on intragastric pH. *Eur J Clin Pharmacol*. 2009; 65:19-31.

Lanza F L, Aspinall R L, Swabb E A, Davis R E, Rack M F, Rubin A. Double-blind placebo-controlled endoscopic comparison of the mucosal protective effects of misoprostol versus cimetidine on tolmetin-induced mucosal injury to the stomach and duodenum. *Gastroenterology*. 1988; 95:289-294.

Lind T, Cederberg C, Ekenved G, Haglund U, Olbe L. Effect of omeprazole—a gastric proton pump inhibitor—on pentagastrin stimulated acid secretion in man. Gut. 1983; 24:270-6.

The invention claimed is:
1. A method for delivering a pharmaceutical composition to a patient in need thereof, comprising:
   administering to said patient a pharmaceutical composition in unit dose form comprising:
      about 325 mg acetylsalicylic acid, or pharmaceutically acceptable salt thereof, and
      about 40 mg omeprazole, or pharmaceutically acceptable salt thereof, wherein said omeprazole, or pharmaceutically acceptable salt thereof:
is an immediate release omeprazole, or pharmaceutically acceptable salt thereof,
is released from said unit dose form at a pH of from about 0 or greater, and
achieves a mean % time at which intragastric pH remains at about 4.0 or greater for about a 24 hour period after reaching steady state of at least about 50%, and
wherein said unit dose form achieves a pharmacokinetic (pk) profile for omeprazole comprising $C_{max}$ under 1200 ng/mL.

2. The method according to claim 1 wherein said pharmaceutical composition in unit dose form has an acetylsalicylic acid $t_{max}$ ranging from about 3 hours to about 4.5 hours.

3. The method according to claim 1 wherein said pharmaceutical composition in unit dose form has an omeprazole $t_{max}$ ranging from about 20 minutes to about 1.5 hours.

4. The method according to claim 1, wherein said unit dose form is administered for a period of at least about 7 days.

5. A method for delivering a pharmaceutical composition to a patient in need thereof, comprising:
administering to said patient a pharmaceutical composition in unit dose form comprising:
about 325 mg acetylsalicylic acid, or pharmaceutically acceptable salt thereof, and
about 40 mg omeprazole, or pharmaceutically acceptable salt thereof,
wherein said omeprazole, or pharmaceutically acceptable salt thereof:
is an immediate release omeprazole, or pharmaceutically acceptable salt thereof,
is released from said unit dose form at a pH of from about 0 or greater,
achieves a mean % time at which intragastric pH remains at about 4.0 or greater for about a 24 hour period after reaching steady state of at least about 50%, and
wherein said unit dose form achieves a pharmacokinetic (pk) profile for omeprazole comprising $AUC_{0-12}$ ranging from about 0.8 hr*µg/mL to about 2.5 hr*µg/mL.

6. The method according to claim 5 wherein said pharmaceutical composition in unit dose form has an acetylsalicylic acid $t_{max}$ ranging from about 3 hours to about 4.5 hours.

7. The method according to claim 5, wherein said pharmaceutical composition in unit dose form has an omeprazole $t_{max}$ ranging from about 20 minutes to about 1.5 hours.

8. The method according to claim 5, wherein said unit dose form is administered for a period of at least about 7 days.

9. The method according to claim 5, wherein said patient in need thereof is being treated for cardiovascular disease, osteoarthritis, rheumatoid arthritis, ankylosing spondylitis, or a combination thereof.

10. A pharmaceutical composition in unit dose form comprising:
a core comprising about 325 mg acetylsalicylic acid, or pharmaceutically acceptable salt thereof;
an enteric coating over said core that at least begins to dissolve when the pH of the surrounding medium is about 3.5 or greater; and
a second layer comprising about 40 mg immediate release omeprazole, or pharmaceutically acceptable salt thereof, wherein said omeprazole, or pharmaceutically acceptable salt thereof is released at a pH of from about 0 or greater;
wherein said unit dose form is administered and achieves a pharmacokinetic (pk) profile for omeprazole comprising a $C_{max}$ under 1200 ng/mL, and
wherein said pharmaceutical composition in unit dose form has an acetylsalicylic acid $t_{max}$ ranging from about 3 hours to about 4.5 hours.

11. The pharmaceutical composition in unit dose form according to claim 10, wherein said pharmaceutical composition in unit dose form has an omeprazole, or pharmaceutically acceptable salt thereof, $t_{max}$ ranging from about 20 minutes to about 1.5 hours.

12. A method for delivering a pharmaceutical composition to a patient in need thereof, comprising:
administering to said patient a pharmaceutical composition in unit dose form comprising:
about 81 mg acetylsalicylic acid, or pharmaceutically acceptable salt thereof, and
about 40 mg omeprazole, or pharmaceutically acceptable salt thereof,
wherein said omeprazole, or pharmaceutically acceptable salt thereof:
is an immediate release omeprazole, or pharmaceutically acceptable salt thereof,
is released from said unit dose form at a pH of from about 0 or greater, and
achieves a mean % time at which intragastric pH remains at about 4.0 or greater for about a 24 hour period after reaching steady state of at least about 50%, and
wherein said unit dose form achieves a pharmacokinetic (pk) profile for omeprazole comprising $C_{max}$ under 1200 ng/mL.

13. The method according to claim 12 wherein said pharmaceutical composition in unit dose form has an acetylsalicylic acid $t_{max}$ ranging from about 3 hours to about 4.5 hours.

14. The method according to claim 12 wherein said pharmaceutical composition in unit dose form has an acetylsalicylic acid $t_{max}$ ranging from about 3 hours to about 3.5 hours.

15. The method according to claim 12 wherein said pharmaceutical composition in unit dose form has an omeprazole $t_{max}$ ranging from about 20 minutes to about 1.5 hours.

16. The method according to claim 12, wherein said unit dose form is administered for a period of at least about 7 days.

17. A method for delivering a pharmaceutical composition to a patient in need thereof, comprising:
administering to said patient a pharmaceutical composition in unit dose form comprising:
about 81 mg acetylsalicylic acid, or pharmaceutically acceptable salt thereof, and
about 40 mg omeprazole, or pharmaceutically acceptable salt thereof,
wherein said omeprazole, or pharmaceutically acceptable salt thereof:
is an immediate release omeprazole, or pharmaceutically acceptable salt thereof,
is released from said unit dose form at a pH of from about 0 or greater, achieves a mean % time at which intragastric pH remains at about 4.0 or greater for about a 24 hour period after reaching steady state of at least about 50%, and wherein said unit dose form achieves a pharmacokinetic (pk) profile for omeprazole comprising $AUC_{0-12}$ ranging from about 0.8 hr*µg/mL to about 2.5 hr*µg/m L.

18. The method according to claim 17 wherein said pharmaceutical composition in unit dose form has an acetylsalicylic acid $t_{max}$ ranging from about 3 hours to about 4.5 hours.

19. The method according to claim 17 wherein said pharmaceutical composition in unit dose form has an acetylsalicylic acid $t_{max}$ ranging from about 3 hours to about 3.5 hours.

20. The method according to claim 17 wherein said pharmaceutical composition in unit dose form has an omeprazole $t_{max}$ ranging from about 20 minutes to about 1.5 hours.

21. The method according to claim 17, wherein said unit dose form is administered for a period of at least about 7 days.

22. A pharmaceutical composition in unit dose form comprising:
- a core comprising about 81 mg acetylsalicylic acid, or pharmaceutically acceptable salt thereof;
- an enteric coating over said core that at least begins to dissolve when the pH of the surrounding medium is about 3.5 or greater; and
- a second layer comprising about 40 mg immediate release omeprazole, or pharmaceutically acceptable salt thereof, wherein said omeprazole, or pharmaceutically acceptable salt thereof is released at a pH of from about 0 or greater;

wherein said unit dose form is administered and achieves a pharmacokinetic (pk) profile for omeprazole comprising a $C_{max}$ under 1200 ng/mL, and wherein said pharmaceutical composition in unit dose form has an acetylsalicylic acid $t_{max}$ ranging from about 3 hours to about 4.5 hours.

23. The pharmaceutical composition according to claim 22 wherein said pharmaceutical composition in unit dose form has an acetylsalicylic acid $t_{max}$ ranging from about 3 hours to about 3.5 hours.

24. The pharmaceutical composition according to claim 22 wherein said pharmaceutical composition in unit dose form has an omeprazole $t_{max}$ ranging from about 20 minutes to about 1.5 hours.

25. The method according to claim 1 wherein said pharmaceutical composition in unit dose form has an acetylsalicylic acid $t_{max}$ ranging from about 3 hours to about 3.5 hours.

26. The method according to claim 5 wherein said pharmaceutical composition in unit dose form has an acetylsalicylic acid $t_{max}$ ranging from about 3 hours to about 3.5 hours.

27. The pharmaceutical composition according to claim 10 wherein said pharmaceutical composition in unit dose form has an acetylsalicylic acid $t_{max}$ ranging from about 3 hours to about 3.5 hours.

* * * * *